(12) United States Patent
Matsuura et al.

(10) Patent No.: US 8,410,251 B2
(45) Date of Patent: Apr. 2, 2013

(54) ANTIBODY AGAINST CALCIFIED GLOBULE AND USE OF THE SAME

(75) Inventors: Eiji Matsuura, Okayama (JP); Hiromi Kumon, Okayama (JP); Kazuo Kojima, Aichi (JP)

(73) Assignees: National University Corporation Okayama University (JP); Medical and Biological Laboratories Co., Ltd. (JP)

( * ) Notice: Subject to any disclaimer, the term of this patent is extended or adjusted under 35 U.S.C. 154(b) by 0 days.

(21) Appl. No.: 13/000,325

(22) PCT Filed: Mar. 9, 2009

(86) PCT No.: PCT/JP2009/054475
§ 371 (c)(1),
(2), (4) Date: Apr. 7, 2011

(87) PCT Pub. No.: WO2009/154026
PCT Pub. Date: Dec. 23, 2009

(65) Prior Publication Data
US 2011/0182817 A1    Jul. 28, 2011

(30) Foreign Application Priority Data

Jun. 20, 2008  (JP) ................................ 2008-162566
Dec. 2, 2008   (JP) ................................ 2008-308016

(51) Int. Cl.
*C07K 16/00* (2006.01)
*C12P 21/08* (2006.01)
*A61K 49/00* (2006.01)

(52) U.S. Cl. ..................... 530/387.1; 530/387.3; 424/9.1

(58) Field of Classification Search ........................ None
See application file for complete search history.

(56) References Cited

U.S. PATENT DOCUMENTS 5,585,089 A * 12/1996 Queen et al. ............... 424/133.1
2003/0185827 A1 * 10/2003 Rodriguez et al. ......... 424/146.1
2011/0182816 A1    7/2011 Matsuura et al.

FOREIGN PATENT DOCUMENTS

| EP | 0334076 A2 | 9/1989 |
| JP | 2818658 B2 | 10/1998 |
| JP | 2004-121152 A | 4/2004 |
| WO | WO-2009-154283 A1 | 12/2009 |

OTHER PUBLICATIONS

Tsimikas, 2002. Am J Cardiol. 90:22-27.*
Mizutani et al, 1995. 38(10): 1382-1388.*
Kraemer et al, 2006. The FASEB Journal. 20: A577.*
Preminger, 2007. "Stones in the Urinary Tract" in the Merck Manual, available at www.merckmanuals.com, 4 pages as printed.*
Lam, 2008. "Atherosclerosis" in the Merck Manual, available at www.merckmanuals.com, 7 pages as printed.*
Matsuura, E., et al., "Establishing the Innovative Diagnostic Imaging Method for Arterioscierosis", Report of the Results of 2007 MHLW Research Grant Program—Discovery of Nanobio-targeted Theraphy and Other Innovative Therapies and Researches onthe Underlying Technologies, (w/ English Translation), (Mar. 2008), 19-28.
Matsuura, E., "Establishing the Innovative Diagnostic Imaging Method for Arteriosclerosis", 2007 MHLW Science and Technology Promotion Program for the Prefectures Where Special Electric Generation Plants are Located—Discovery of Nanobio-targeted Therapy and Other Innovative Therapies and Researches on the Underlying Technologies, (w/ English Translation), (2008), 12 pgs.
Matsuura, E., "Establishing the Innovative Diagnostic Imaging Method for Arteriosclerosis", 2007 MHLW Science and Technology Promotion Program for the Prefectures Where Special Electric Generation Plants are Located—Discovery of Nanobio-targeted Therapy and Other Innovative Therapies and Researches on the Underlying Technologies, (w/ English Translation), (2008), 10 pgs.
"Creation of the Interdisciplinary Center for the Discovery of Nanobio-targeted Therapy", (w/ English Translation), Okadai hatsu Igaku Iryo no Saizensen, vol. 29, (Apr. 20, 2009), 6 pgs.
"Creation of the Interdisciplinary Center for the Discovery of Nanobio-targeted Therapy", (w/ English Translation), Okadai hatsu Igaku Iryo no Saizensen, vol. 29, Okayama Daigaku Kenkyu Suishin Sangakukan Renkei Kiko Website. [online]. [Apr. 24, 2009]. Retrieved from the Internet: <URL: http://ww.okayama-u.net/medic/icont/materials/results/0904vol29.pdf>, (Apr. 20, 2009), 4 pgs.
"Creation of the Interdisciplinary Center for the Discovery of Nanobio-targeted Therapy", (w/ English Translation), Okadai hatsu Igaku Iryo no Saizensen, Vol. 30, (May 25, 2009), 7 pgs.
"Creation of the Interdisciplinary Center for the Discovery of Nanobio-targeted Therapy", (w/English Translation), Okadai hatsu Igaku Iryo no Saizensen, vol. 30, Okayama Daigaku Kenkyu Suishin Sangakukan Renkei Kiko Website. [online]. [May 27, 2009]. Retrieved from the Internet: <URL:http://ww.okayama-u.net/medic/icont/materials/ results/0905vol30.pdf>, (May 25, 2009), 5 pgs.
"International Application Serial No. PCT/JP2009/054475, International Preliminary Report on Patentability dated Feb. 8, 2011", (w/English Translation), 14 pgs.
"International Application Serial No. PCT/JP2009/054475, International Search Report mailed Apr. 14, 2009", (w/ English Translation), 4 pgs.
"International Application Serial No. PCT/JP2009/054475, Written Opinion mailed Apr. 14 2009", (w/ English Translation), 12 pgs.
"Machine Translation of JP 2004-121152A, published Apr. 22, 2004", 17 pgs.
"Machine Translation of WO 2009-154283A1, pubiished Dec. 23, 2009", 58 pgs.

(Continued)

*Primary Examiner* — Zachary Howard
(74) *Attorney, Agent, or Firm* — Schwegman Lundberg & Woessner, P.A.

(57) ABSTRACT

The present inventors carried out immunization using renal/urinary calculus-derived calcified globules or carotid artery-derived arteriosclerotic plaques, and then obtained antibodies specific to calcified globules (NLO) via screening with NLO. The present inventors demonstrated that the antibodies reacted specifically to arteriosclerotic lesions (calcified lesions) and visualized arteriosclerotic plaques (in particular, calcified lesions) by using fluorescently labeled antibodies. Accordingly, the present inventors completed the present invention.

16 Claims, 25 Drawing Sheets

OTHER PUBLICATIONS

"Mysterious Microogranism Obtained form Calculi", (w/ English Translation), Okadai hatsu Igaku Iryo no Saizensen, vol. 27, (Feb. 23, 2009), 6 pgs.

"Mysterious Microorganism Obtained from Calculi", (w/ English Translation), Okadai hatsu Igaku Iryo no Saizensen, Vol. 27, Okayama Daigaku Kenkyu Suishin Sangakukan Renkei Kiko Website. [online]. [Feb. 25, 2009]. Retrieved from the Internet: <URL:http:www.okayama-u.net/medic/icont.materials/results/0902vol27.pdf>, (Feb. 23, 2009), 4 pgs.

"What is the mysterious microorganism?", (w/ English Translation), Okadai hatsu Igaku Iryo no Saizensen vol. 28, (Mar. 23, 2009), 7 pgs.

"What is the mysterious microorganism?", (w/ English Translation), Okadai hatsu Igaku Iryo no Saizensen vol. 28, Okayama Daigaku Kenkyu Suishin Sangakukan Renkei Kiko Website. [online]. [Mar. 27, 2009]. Retrieved from the Internet: http://www.okayama-u.net/medic/icont/materials/results/0903vol28.pdf>, (Mar. 23, 2009), 5 pgs.

Kajander, E. O., et al., "Nanobacteria: An alternative mechanism for pathogenic intra- and extracellular calcification and stone formation", Proc. Natl. Acad. Sci. USA, 95(14), (Jul. 1998), 8274-8279.

Koide, T., et al., "Jin—Nyoro Kesseki no Shotai wa", Journal of Practical Pharmacy, 38(1), (1987), 7-12.

Matsuura, E., et al., A Conference to Report Research Outcomes—Abstracts, 2008 Research Grant Program for Science and Technology Promotion for the Prefectures Where Special Electrictruc Generation Plants are Located, "Discovery of Nanobio-targeted Therapy and Other Innovative Therapies and Researches on the Underlying Technologies" (w/ English Translation), (Mar. 10, 2009), 19 pgs.

Matsuura, E., et al., "Establishing the Comprehensive Diagnostic Imaging Method Toward the 21st Century Therapies", (w/ English Translation), Discovery of Nanobio-targeted Therapy and Other Innovative Therapies and Researches on the Underlying Technologies—Report of Research Results, (Mar. 2009), 30 pgs.

Matsuura, E., et al., "Establshing the Comprehensive Diagnostic Imaging Method toward the 21st Century Therapies", (w/ English Translation), Medical Techno Okayama HP [online]. [Mar. 25, 2009]. Retrieved from the Internet: <URL: http://www.optic.or.jp/medical/itaku/ dengen/matsuura.pdf>, (2009), 2 pgs.

Matsuura, E., et al., "Establishing the Innovative Diagnostic Imaging Method for Arteriosclerosis" ["Kakkiteki na Domyaku Koka no Gaza Shindanho no Kakuritsu"], 2007 MHLW Science and Technology Promotion Program for the Prefectures Where Special Electric Generation Plants are Located, Discovery of Nanobio-targeted Therapy and Other Innovative Therapies and Researches on the Underlying Technologies—A Conference to Report Research Outcomes (w/ English Translation), (Mar. 11, 2008), 12 pgs.

Suzuki, T., et al., "Analysis of pancreatic stone protein gene of hereditary pancreatis", ["Kazokusei Suien ni Okeru Suiseki Tanpaku Idenshi no Kaiseki"], (w/ English Abstract), Nihon Shokakibyo Gakkai Zasshi, 89(3), (1992), 633-638.

* cited by examiner

HEAVY CHAIN VARIABLE REGION

|  | FRAMEWORK 1 | CDR1 | FRAMEWORK 2 | CDR2 |
|---|---|---|---|---|
| (SEQ ID NO: 4) CL15-203 | QVQLKESGPGLVAPSQSLSITCTVSGFSLT | DYGVS | WIRQPPGKGLEWLG | VIWGGGSTYYNSALKS |
| (SEQ ID NO: 14) CL19-107 | EVQLQQSGPELVKPGASVKISCKTSGYTFT | EYTMH | WVKQSHGKSLEWIG | GINPNNGGTSYNQKFKG |
| (SEQ ID NO: 24) CL21-35 | QVQLQQPGAELVRPGASVKLSCKASGYSFT | SYWMN | WVKQRPGQGLEWIG | MIHPSDSETRLNQKFKD |
| (SEQ ID NO: 34) CL48-139 | EGQLQQSGAEVVKPGASVKLSCTASGFNIK | DTYIH | WVKQRPEQGLEWIG | RIDPTNGNTKYDPEFQG |
| (SEQ ID NO: 44) CL56-369 | QVQLQQPGAELVKPGASVKLSCKASGYTFT | SYWMH | WVKQRPGQGLEWIG | EIDPSDSYTNYNQKFKG |

|  | FRAMEWORK 3 | CDR3 | FRAMEWORK 4 |
|---|---|---|---|
| CL15-203 | RLSISKDNSKSQVFLKMNSLQTDDTAMYYCAK | HGRMGRKNYFDY | WGQGTTLTVSS |
| CL19-107 | KATLTVDKSSSTAYMELRSLTSEDSAVYYCAR | SGDYGTGAWFAY | WGQGTLVTVSA |
| CL21-35 | KATLTVDKSSSTAYMQLSSPTSEDSAVYYCAR | RGYYGSTRKNYYAMDY | WGQGTSVTVSS |
| CL48-139 | KATITADTSSNTAYLHLSGLTSEDTAVYYCAK | GTLFAY | WGQGTLVTVSA |
| CL56-369 | KATLTVDKSSSTAYMQLSSLTSEDSAVYYCAR | GDMDAMDY | WGQGTSVTVSS |

LIGHT CHAIN VARIABLE REGION

|  | FRAMEWORK 1 | CDR1 | FRAMEWORK 2 | CDR2 |
|---|---|---|---|---|
| (SEQ ID NO: 9) CL15-203 | DVQITQSPSYLAASPGETITINC | RASKSISKYLA | WYQEKPGKTNKLLIY | SGSTLQS |
| (SEQ ID NO: 19) CL19-107 | DIVMSQSPSSLAVSAGEKVTMSC | KSSQSLLNSRTRKNYLA | WYQQKPGQSPKLLIY | WASTRES |
| (SEQ ID NO: 29) CL21-35 | DIQMTQSPASLSVSVGETVTITC | RASENIYSNLA | WYQQKQGKSPQLLVY | AATNLAD |
| (SEQ ID NO: 39) CL48-139 | DIKMTQSPSSMYASLGERVTFTC | KASQDINNYLT | WVQQKPGKSPKTLIY | RANRLVD |
| (SEQ ID NO: 49) CL56-369 | ETTVTQSPASLSMAIGEKVTMC | ITSTDIDDDMN | WYQQKPGEPPKLLIS | EGNTLRP |

|  | FRAMEWORK 3 | CDR3 | FRAMEWORK 4 |
|---|---|---|---|
| CL15-203 | GIPSRFSGSGSGTDFTLTISSLEPEDFAMYYC | QQHNEYPYT | FGGGTKLEIK |
| CL19-107 | GVPDRFTGSGSGTDFTLTISSVQAEDLAVYYC | KQSYNLFT | FGSGTKLEIK |
| CL21-35 | GVPSRFSGSGSGTQYSLKINSLQSEDFGSYYC | QHFWGTLT | FGSGTKLEIK |
| CL48-139 | GVPSRFSGSGSGQDYSLTISSLEYEDMGIYYC | LQYDEFPPT | FGGGTKLEIK |
| CL56-369 | GVPSRFSSSGYGTDFVFTIENMLSEDVADYYC | LQSDNLPLT | FGAGTKLELK |

FIG. 7

(A) SYSTEMIC IMAGE
(C) HEART AND THORACIC AORTA VISIBLE IMAGE
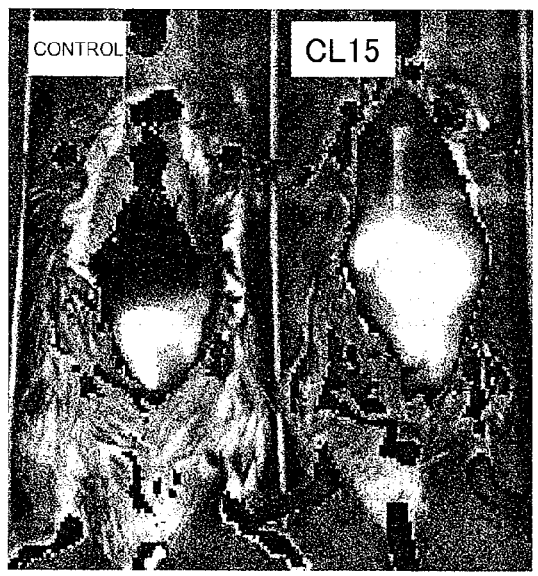
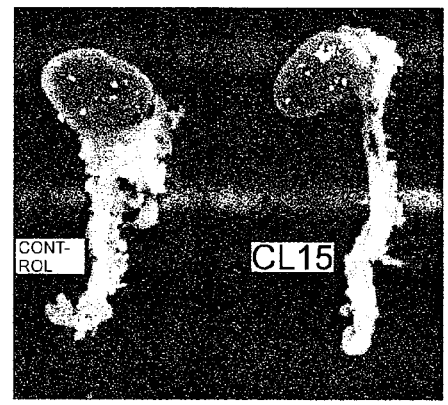
FLUORESCENCE IMAGE
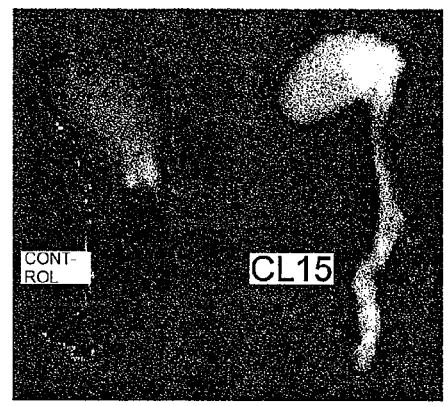
(B) CHEST IMAGE
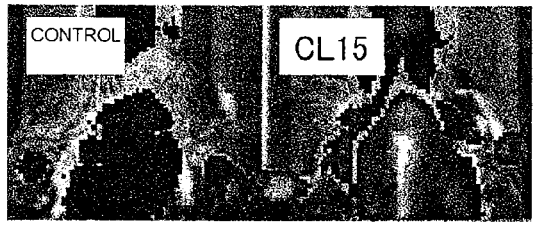
FIG. 9

EXPERIMENT 1
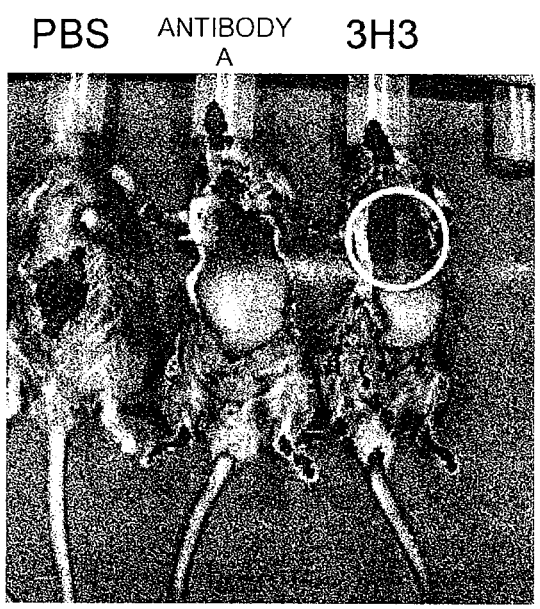
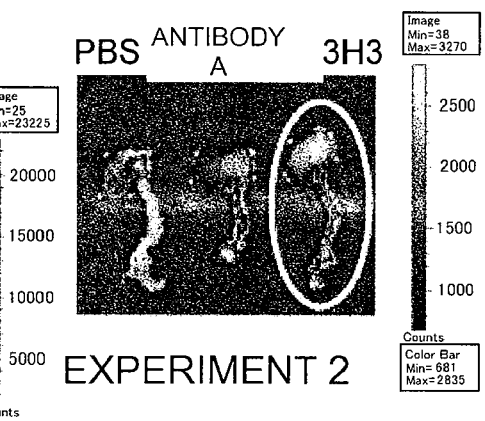
EXPERIMENT 2
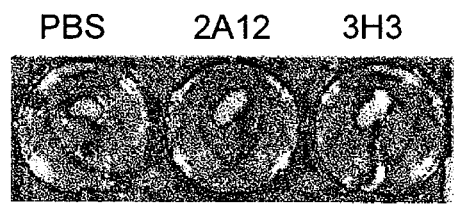
FIG. 21

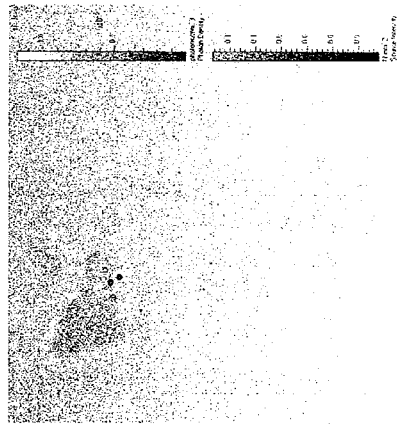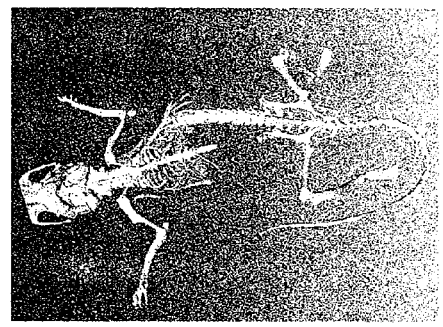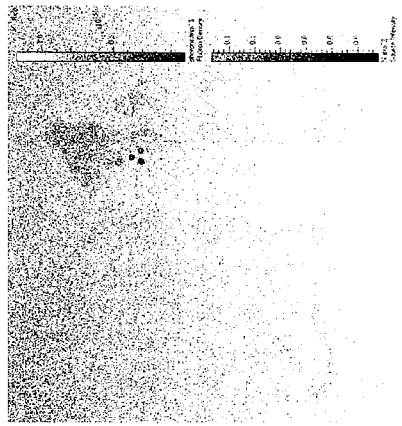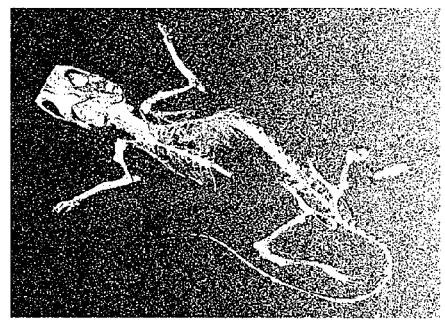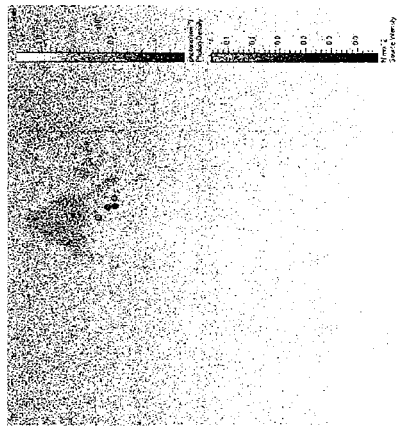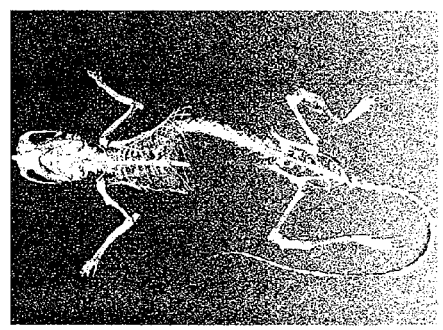
(A) (B)
FIG. 23

HEAVY CHAIN (SEQ ID NO: 53)

```
         10         20         30         40         50         60
EVQLVESGGG LVKPGGSLKL SCAASGFTFS SYAMSWARQT PEKRLEWVAT ISSGGSYTYY
                                      CDR1                  CDR2
         70         80         90        100        110
PDSVRGRFTI SRDNAKNTLY LQMCSLRSED TAMYYCARFD GYYAMDYWGQ GTSVTVSS
                                           CDR3
```

LIGHT CHAIN (SEQ ID NO: 58)

```
         10         20         30         40         50         60
DIVMTQSHKF MSTSVGDRVS ITCKASQDVG SAVAWYQQKP GQSPKLLIYW ASTRHTGVPD
                          CDR1                             CDR2
         70         80         90        100        110
RFTGSGSGTD FTLTISSLQS EDLADYFCQQ YSSYPLTFGS GTKLEIK
                                    CDR3
```

FIG. 25

SEQUENCE LISTING

<160> NUMBER OF SEQ ID NOS: 88

<210> SEQ ID NO 1
<211> LENGTH: 5
<212> TYPE: PRT
<213> ORGANISM: Mus musculus

<400> SEQUENCE: 1

Asp Tyr Gly Val Ser
1               5

<210> SEQ ID NO 2
<211> LENGTH: 16
<212> TYPE: PRT
<213> ORGANISM: Mus musculus

<400> SEQUENCE: 2

Val Ile Trp Gly Gly Gly Ser Thr Tyr Tyr Asn Ser Ala Leu Lys Ser
1               5                   10                  15

<210> SEQ ID NO 3
<211> LENGTH: 12
<212> TYPE: PRT
<213> ORGANISM: Mus musculus

<400> SEQUENCE: 3

His Gly Arg Met Gly Arg Lys Asn Tyr Phe Asp Tyr
1               5                   10

<210> SEQ ID NO 4
<211> LENGTH: 120
<212> TYPE: PRT
<213> ORGANISM: Mus musculus

<400> SEQUENCE: 4

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp Tyr
                20                  25                  30

Gly Val Ser Trp Ile Arg Gln Pro Pro Gly Lys Gly Leu Glu Trp Leu
            35                  40                  45

Gly Val Ile Trp Gly Gly Gly Ser Thr Tyr Tyr Asn Ser Ala Leu Lys
        50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Lys His Gly Arg Met Gly Arg Lys Asn Tyr Phe Asp Tyr Trp Gly Gln
            100                 105                 110

Gly Thr Thr Leu Thr Val Ser Ser
        115                 120

<210> SEQ ID NO 5
<211> LENGTH: 360
<212> TYPE: DNA
<213> ORGANISM: Mus musculus

<400> SEQUENCE: 5
caggtgcagc tgaaggagtc aggacctggc ctggtggcgc cctcacagag cctgtccatc      60
acatgcactg tctcagggtt ctcattaacc gactatggtg taagctggat tcgccagcct     120

```
ccaggaaagg gtctggagtg gctgggagta atatggggtg gtggaagcac atactataat    180
tcagctctca atccagact gagcatcagc aaggacaact ccaagagcca agttttctta    240
aaaatgaaca gtctgcaaac tgatgacaca gccatgtact actgtgccaa acatggaagg    300
atgggacgta agaactactt tgactactgg ggccaaggca ccactctcac agtctcctca    360
```

<210> SEQ ID NO 6
<211> LENGTH: 11
<212> TYPE: PRT
<213> ORGANISM: Mus musculus

<400> SEQUENCE: 6

Arg Ala Ser Lys Ser Ile Ser Lys Tyr Leu Ala
1               5                   10

<210> SEQ ID NO 7
<211> LENGTH: 7
<212> TYPE: PRT
<213> ORGANISM: Mus musculus

<400> SEQUENCE: 7

Ser Gly Ser Thr Leu Gln Ser
1               5

<210> SEQ ID NO 8
<211> LENGTH: 9
<212> TYPE: PRT
<213> ORGANISM: Mus musculus

<400> SEQUENCE: 8

Gln Gln His Asn Glu Tyr Pro Tyr Thr
1               5

<210> SEQ ID NO 9
<211> LENGTH: 107
<212> TYPE: PRT
<213> ORGANISM: Mus musculus

<400> SEQUENCE: 9

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Tyr
                85                  90                  95

Thr Phe Gly Gly Gly Thr Lys Leu Glu Ile Lys
            100                 105

<210> SEQ ID NO 10
<211> LENGTH: 321
<212> TYPE: DNA
<213> ORGANISM: Mus musculus

<400> SEQUENCE: 10

```
gatgtccaga taacccagtc tccatcttat cttgctgcat ctcctggaga aaccattact    60
```

```
attaattgca gggcaagtaa gagcattagc aaatatttag cctggtatca agagaaacct    120
gggaaaacta ataagcttct tatctactct ggatccactt tgcaatctgg aattccatca    180
aggttcagtg gcagtggatc tggtacagat ttcactctca ccatcagtag cctggagcct    240
gaagattttg caatgtatta ctgtcaacag cataatgaat acccgtacac gttcggaggg    300
gggaccaagc tggaaataaa a    321
```

<210> SEQ ID NO 11
<211> LENGTH: 5
<212> TYPE: PRT
<213> ORGANISM: Mus musculus

<400> SEQUENCE: 11

Glu Tyr Thr Met His
1               5

<210> SEQ ID NO 12
<211> LENGTH: 17
<212> TYPE: PRT
<213> ORGANISM: Mus musculus

<400> SEQUENCE: 12

Gly Ile Asn Pro Asn Asn Gly Gly Thr Ser Tyr Asn Gln Lys Phe Lys
1               5                   10                  15

Gly

<210> SEQ ID NO 13
<211> LENGTH: 12
<212> TYPE: PRT
<213> ORGANISM: Mus musculus

<400> SEQUENCE: 13

Ser Gly Asp Tyr Gly Thr Gly Ala Trp Phe Ala Tyr
1               5                   10

<210> SEQ ID NO 14
<211> LENGTH: 121
<212> TYPE: PRT
<213> ORGANISM: Mus musculus

<400> SEQUENCE: 14

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Gly Ile Asn Pro Asn Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Ser Gly Asp Tyr Gly Thr Gly Ala Trp Phe Ala Tyr Trp Gly
            100                 105                 110

Gln Gly Thr Leu Val Thr Val Ser Ala
        115                 120

<210> SEQ ID NO 15

```
<211> LENGTH: 363
<212> TYPE: DNA
<213> ORGANISM: Mus musculus

<400> SEQUENCE: 15
gaggtccagc tgcaacagtc tggacctgag ctggtgaagc ctggggcttc agtgaagata      60
tcctgcaaga cttctggata cacattcact gaatacacca tgcactgggt gaagcagagc     120
catggaaaga gccttgagtg gattggaggt attaatccta acaatggtgg tactagctac     180
aaccagaagt tcaagggcaa ggccacattg actgtagaca gtcctccag  cacagcctac     240 atggagctcc gcagcctgac atctgaggat tctgcagtct attactgtgc aagatctgga     300
gattacggga caggggcctg gtttgcttac tggggccaag ggactctggt cactgtctct     360
gca                                                                   363

<210> SEQ ID NO 16
<211> LENGTH: 17
<212> TYPE: PRT
<213> ORGANISM: Mus musculus

<400> SEQUENCE: 16

Lys Ser Ser Gln Ser Leu Leu Asn Ser Arg Thr Arg Lys Asn Tyr Leu
1               5                   10                  15

Ala

<210> SEQ ID NO 17
<211> LENGTH: 7
<212> TYPE: PRT
<213> ORGANISM: Mus musculus

<400> SEQUENCE: 17

Trp Ala Ser Thr Arg Glu Ser
1               5

<210> SEQ ID NO 18
<211> LENGTH: 8
<212> TYPE: PRT
<213> ORGANISM: Mus musculus

<400> SEQUENCE: 18

Lys Gln Ser Tyr Asn Leu Phe Thr
1               5

<210> SEQ ID NO 19
<211> LENGTH: 112
<212> TYPE: PRT
<213> ORGANISM: Mus musculus

<400> SEQUENCE: 19

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
                20                  25                  30

Arg Thr Arg Lys Asn Tyr Leu Ala Trp Tyr Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95
```

Ser Tyr Asn Leu Phe Thr Phe Gly Ser Gly Thr Lys Leu Glu Ile Lys
            100                 105                 110

<210> SEQ ID NO 20
<211> LENGTH: 336
<212> TYPE: DNA
<213> ORGANISM: Mus musculus

<400> SEQUENCE: 20
gacattgtga tgtcacagtc tccatcctcc ctggctgtgt cagcaggaga gaaggtcact    60
atgagctgca atccagtca gagtctgctc aacagtagaa cccgaaagaa ctacttggct    120
tggtaccagc agaaaccagg gcagtctcct aaactgctga tctactgggc atccactagg    180
gaatctgggg tccctgatcg cttcacaggc agtggatctg ggacagattt cactctcacc    240
atcagcagtg tgcaggctga agacctggca gtttattact gcaagcaatc ttataatcta    300
ttcacgttcg gctcggggac aaagttggaa ataaaa                             336

<210> SEQ ID NO 21
<211> LENGTH: 5
<212> TYPE: PRT
<213> ORGANISM: Mus musculus

<400> SEQUENCE: 21

Ser Tyr Trp Met Asn
1               5

<210> SEQ ID NO 22
<211> LENGTH: 17
<212> TYPE: PRT
<213> ORGANISM: Mus musculus

<400> SEQUENCE: 22

Met Ile His Pro Ser Asp Ser Glu Thr Arg Leu Asn Gln Lys Phe Lys
1               5                   10                  15

Asp

<210> SEQ ID NO 23
<211> LENGTH: 16
<212> TYPE: PRT
<213> ORGANISM: Mus musculus

<400> SEQUENCE: 23

Arg Gly Tyr Tyr Gly Ser Thr Arg Lys Asn Tyr Ala Met Asp Tyr
1               5                   10                  15

<210> SEQ ID NO 24
<211> LENGTH: 125
<212> TYPE: PRT
<213> ORGANISM: Mus musculus

<400> SEQUENCE: 24

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Ser Phe Thr Ser Tyr
            20                  25                  30

Trp Met Asn Trp Val Lys Gln Arg Pro Gly Gln Gly Leu Glu Trp Ile
        35                  40                  45

Gly Met Ile His Pro Ser Asp Ser Glu Thr Arg Leu Asn Gln Lys Phe
    50                  55                  60

Lys Asp Lys Ala Thr Leu Thr Val Asp Lys Ser Ser Ser Thr Ala Tyr

```
                65                  70                  75                  80
Met Gln Leu Ser Ser Pro Thr Ser Glu Asp Ser Ala Val Tyr Tyr Cys
                    85                  90                  95

Ala Arg Arg Gly Tyr Tyr Gly Ser Thr Arg Lys Asn Tyr Tyr Ala Met
                100                 105                 110

Asp Tyr Trp Gly Gln Gly Thr Ser Val Thr Val Ser Ser
        115                 120                 125

<210> SEQ ID NO 25
<211> LENGTH: 375
<212> TYPE: DNA
<213> ORGANISM: Mus musculus

<400> SEQUENCE: 25
caggtccaac tgcagcagcc tggggctgag ctggtgaggc ctggagcttc agtgaagctg        60
tcctgcaagg cttctggcta ctccttcacc agctactgga tgaactgggt gaagcagagg       120
cctggacaag gccttgagtg gattggcatg attcatcctt ccgatagtga aactaggtta       180
aatcagaagt tcaaggacaa ggccacattg actgtagaca atcctccag cacagcctac        240 atgcaactca gcagcccgac atctgaggac tctgcggtct attactgtgc aagaagaggg       300
tactacggat caacccgaaa aaattactat gctatggact actggggtca aggaaccta        360 gtcaccgtct cctca                                                         375

<210> SEQ ID NO 26
<211> LENGTH: 11
<212> TYPE: PRT
<213> ORGANISM: Mus musculus

<400> SEQUENCE: 26

Arg Ala Ser Glu Asn Ile Tyr Ser Asn Leu Ala
1               5                   10

<210> SEQ ID NO 27
<211> LENGTH: 7
<212> TYPE: PRT
<213> ORGANISM: Mus musculus

<400> SEQUENCE: 27

Ala Ala Thr Asn Leu Ala Asp
1               5

<210> SEQ ID NO 28
<211> LENGTH: 8
<212> TYPE: PRT
<213> ORGANISM: Mus musculus

<400> SEQUENCE: 28

Gln His Phe Trp Gly Thr Leu Thr
1               5

<210> SEQ ID NO 29
<211> LENGTH: 106
<212> TYPE: PRT
<213> ORGANISM: Mus musculus

<400> SEQUENCE: 29

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30
```

```
Leu Ala Trp Tyr Gln Gln Lys Gln Gly Lys Ser Pro Gln Leu Leu Val
             35                  40                  45

Tyr Ala Ala Thr Asn Leu Ala Asp Gly Val Pro Ser Arg Phe Ser Gly
         50                  55                  60

Ser Gly Ser Gly Thr Gln Tyr Ser Leu Lys Ile Asn Ser Leu Gln Ser
 65                  70                  75                  80

Glu Asp Phe Gly Ser Tyr Tyr Cys Gln His Phe Trp Gly Thr Leu Thr
                 85                  90                  95

Phe Gly Ser Gly Thr Lys Leu Glu Ile Lys
            100                 105

<210> SEQ ID NO 30
<211> LENGTH: 318
<212> TYPE: DNA
<213> ORGANISM: Mus musculus

<400> SEQUENCE: 30
gacatccaga tgactcagtc tccagcctcc ctatctgtat ctgtgggaga aactgtcacc      60
atcacatgtc gagcaagtga gaatatttac agtaatttag catggtatca gcagaaacag     120
ggaaaatctc ctcagctcct ggtctatgct gcaacaaact tagcagatgg tgtgccatca     180
aggttcagtg gcagtggatc aggcacacag tattccctca agatcaacag cctgcagtct     240
gaagattttg ggagttatta ctgtcaacat ttttggggta ctctcacgtt cggctcgggg     300
acaaagttgg aaataaaa                                                   318

<210> SEQ ID NO 31
<211> LENGTH: 5
<212> TYPE: PRT
<213> ORGANISM: Mus musculus

<400> SEQUENCE: 31

Asp Thr Tyr Ile His
1               5

<210> SEQ ID NO 32
<211> LENGTH: 17
<212> TYPE: PRT
<213> ORGANISM: Mus musculus

<400> SEQUENCE: 32

Arg Ile Asp Pro Thr Asn Gly Asn Thr Lys Tyr Asp Pro Glu Phe Gln
1               5                   10                  15

Gly

<210> SEQ ID NO 33
<211> LENGTH: 6
<212> TYPE: PRT
<213> ORGANISM: Mus musculus

<400> SEQUENCE: 33

Gly Thr Leu Phe Ala Tyr
1               5

<210> SEQ ID NO 34
<211> LENGTH: 115
<212> TYPE: PRT
<213> ORGANISM: Mus musculus

<400> SEQUENCE: 34

Glu Gly Gln Leu Gln Gln Ser Gly Ala Glu Val Val Lys Pro Gly Ala
1               5                   10                  15
```

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Thr Asn Gly Asn Thr Lys Tyr Asp Pro Glu Phe
    50                  55                  60

Gln Gly Lys Ala Thr Ile Thr Ala Asp Thr Ser Ser Asn Thr Ala Tyr
65                  70                  75                  80

Leu His Leu Ser Gly Leu Thr Ser Glu Asp Thr Ala Val Tyr Tyr Cys
                85                  90                  95

Ala Lys Gly Thr Leu Phe Ala Tyr Trp Gly Gln Gly Thr Leu Val Thr
            100                 105                 110

Val Ser Ala
        115

<210> SEQ ID NO 35
<211> LENGTH: 345
<212> TYPE: DNA
<213> ORGANISM: Mus musculus

<400> SEQUENCE: 35
gagggtcagc tgcagcaatc tggggcagag gttgtgaagc caggggcctc agtcaagttg     60
tcctgcacag cttctggctt caacattaaa gacacctata tactgggt gaaacagagg      120 cctgaacagg gcctggagtg gattggaagg attgatccta cgaatggtaa tactaaatat    180
gacccggaat tccagggcaa ggccactata actgcagaca catcctccaa cacagcctac    240
ctccacctca gcggcctgac atctgaggac actgccgtct attactgtgc taaggggacc    300
ctgtttgctt actggggcca aggactctg gtcactgtct ctgca                     345

<210> SEQ ID NO 36
<211> LENGTH: 11
<212> TYPE: PRT
<213> ORGANISM: Mus musculus

<400> SEQUENCE: 36

Lys Ala Ser Gln Asp Ile Asn Asn Tyr Leu Thr
1               5                   10

<210> SEQ ID NO 37
<211> LENGTH: 7
<212> TYPE: PRT
<213> ORGANISM: Mus musculus

<400> SEQUENCE: 37

Arg Ala Asn Arg Leu Val Asp
1               5

<210> SEQ ID NO 38
<211> LENGTH: 9
<212> TYPE: PRT
<213> ORGANISM: Mus musculus

<400> SEQUENCE: 38

Leu Gln Tyr Asp Glu Phe Pro Pro Thr
1               5

<210> SEQ ID NO 39
<211> LENGTH: 107
<212> TYPE: PRT
<213> ORGANISM: Mus musculus

<400> SEQUENCE: 39

Asp Ile Lys Met Thr Gln Ser Pro Ser Ser Met Tyr Ala Ser Leu Gly
1               5                   10                  15

Glu Arg Val Thr Phe Thr Cys Lys Ala Ser Gln Asp Ile Asn Asn Tyr
            20                  25                  30

Leu Thr Trp Val Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Pro
                85                  90                  95

Thr Phe Gly Gly Gly Thr Lys Leu Glu Ile Lys
            100                 105

<210> SEQ ID NO 40
<211> LENGTH: 321
<212> TYPE: DNA
<213> ORGANISM: Mus musculus

<400> SEQUENCE: 40
gacatcaaga tgacccagtc tccatcttcc atgtatgcat ctctaggaga gagagtcact      60
ttcacttgca aggcgagtca ggacattaat aactatttaa cctgggtcca gcagaaacca     120
gggaaatctc ctaagaccct gatctatcgt gcaaatagat tggtagatgg ggtcccatca     180
aggttcagtg gcagtggatc tgggcaagat tattctctca ccatcagcag cctggagtat     240
gaagatatgg gaatttatta ttgtctacag tatgatgagt tcctcccac gttcggaggg      300
gggaccaagc tggaaataaa a                                               321

<210> SEQ ID NO 41
<211> LENGTH: 5
<212> TYPE: PRT
<213> ORGANISM: Mus musculus

<400> SEQUENCE: 41

Ser Tyr Trp Met His
1               5

<210> SEQ ID NO 42
<211> LENGTH: 17
<212> TYPE: PRT
<213> ORGANISM: Mus musculus

<400> SEQUENCE: 42

Glu Ile Asp Pro Ser Asp Ser Tyr Thr Asn Tyr Asn Gln Lys Phe Lys
1               5                   10                  15

Gly

<210> SEQ ID NO 43
<211> LENGTH: 8
<212> TYPE: PRT
<213> ORGANISM: Mus musculus

<400> SEQUENCE: 43

Gly Asp Met Asp Ala Met Asp Tyr
1               5

<210> SEQ ID NO 44
<211> LENGTH: 117
<212> TYPE: PRT
<213> ORGANISM: Mus musculus

<400> SEQUENCE: 44

Gln Val Gln Leu Gln Gln Pro Gly Ala Glu Leu Val Lys Pro Gly Ala
1               5                   10                  15
Ser Val Lys Leu Ser Cys Lys Ala Ser Gly Tyr Thr Phe Thr Ser Tyr
            20                  25                  30
Trp Met His Trp Val Lys Gln Arg Pro Gly Gln Gly Leu Glu Trp Ile
        35                  40                  45
Gly Glu Ile Asp Pro Ser Asp Ser Tyr Thr Asn Tyr Asn Gln Lys Phe
    50                  55                  60
Lys Gly Lys Ala Thr Leu Thr Val Asp Lys Ser Ser Ser Thr Ala Tyr
65                  70                  75                  80
Met Gln Leu Ser Ser Leu Thr Ser Glu Asp Ser Ala Val Tyr Tyr Cys
                85                  90                  95
Ala Arg Gly Asp Met Asp Ala Met Asp Tyr Trp Gly Gln Gly Thr Ser
            100                 105                 110
Val Thr Val Ser Ser
        115

<210> SEQ ID NO 45
<211> LENGTH: 351
<212> TYPE: DNA
<213> ORGANISM: Mus musculus

<400> SEQUENCE: 45
caggtccaac tgcagcagcc tggggctgag cttgtgaagc ctggggcttc agtgaagctg      60
tcctgcaagg cttctggcta caccttcacc agctactgga tgcactgggt gaagcagagg     120
cctggacaag gccttgagtg gatcggagag attgatcctt ctgatagtta tactaactac     180
aatcaaaagt tcaagggcaa ggccacattg actgtagaca atcctccag cacagcctac      240
atgcagctca gcagcctgac atctgaggac tctgcggtct attactgtgc aagaggagat     300
atggatgcta tggactactg gggtcaagga acctcagtca ccgtctcctc a              351

<210> SEQ ID NO 46
<211> LENGTH: 11
<212> TYPE: PRT
<213> ORGANISM: Mus musculus

<400> SEQUENCE: 46

Ile Thr Ser Thr Asp Ile Asp Asp Asp Met Asn
1               5                   10

<210> SEQ ID NO 47
<211> LENGTH: 7
<212> TYPE: PRT
<213> ORGANISM: Mus musculus

<400> SEQUENCE: 47

Glu Gly Asn Thr Leu Arg Pro
1               5

<210> SEQ ID NO 48
<211> LENGTH: 9
<212> TYPE: PRT
<213> ORGANISM: Mus musculus

<400> SEQUENCE: 48

```
Leu Gln Ser Asp Asn Leu Pro Leu Thr
1               5

<210> SEQ ID NO 49
<211> LENGTH: 107
<212> TYPE: PRT
<213> ORGANISM: Mus musculus

<400> SEQUENCE: 49

Glu Thr Thr Val Thr Gln Ser Pro Ala Ser Leu Ser Met Ala Ile Gly
1               5                   10                  15

Glu Lys Val Thr Ile Arg Cys Ile Thr Ser Thr Asp Ile Asp Asp Asp
                20                  25                  30

Met Asn Trp Tyr Gln Gln Lys Pro Gly Glu Pro Pro Lys Leu Leu Ile
            35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asn Leu Pro Leu
                85                  90                  95

Thr Phe Gly Ala Gly Thr Lys Leu Glu Leu Lys
            100                 105

<210> SEQ ID NO 50
<211> LENGTH: 321
<212> TYPE: DNA
<213> ORGANISM: Mus musculus

<400> SEQUENCE: 50
gaaacaactg tgacccagtc tccagcatcc ctgtccatgg ctataggaga aaaagtcacc      60
atcagatgca taaccagcac tgatattgat gatgatatga actggtacca gcagaagcca     120
ggggaacctc ctaagctcct tatttcagaa ggcaatactc ttcgtcctgg agtcccatcc     180
cgattctcca gcagtggcta tggtacagat tttgttttta caattgaaaa catgctctca     240
gaagatgttg cagattacta ctgtttgcaa agtgataact tgccgctcac gttcggtgct     300
gggaccaagc tggagctgaa a                                               321

<210> SEQ ID NO 51
<211> LENGTH: 28
<212> TYPE: DNA
<213> ORGANISM: Artificial
<220> FEATURE:
<223> OTHER INFORMATION: An artificially synthesized primer sequence

<400> SEQUENCE: 51
tcaatagcag gtgccgcctg tgtcagac                                         28

<210> SEQ ID NO 52
<211> LENGTH: 38
<212> TYPE: DNA
<213> ORGANISM: Artificial
<220> FEATURE:
<223> OTHER INFORMATION: An artificially synthesized primer sequence

<400> SEQUENCE: 52
tcaacactca ttcctgttga agctcttgac aatgggtg                              38

<210> SEQ ID NO 53
<211> LENGTH: 118
```

```
<212> TYPE: PRT
<213> ORGANISM: Mus musculus

<400> SEQUENCE: 53

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Ala Arg Gln Thr Pro Glu Lys Arg Leu Glu Trp Val
        35                  40                  45

Ala Thr Ile Ser Ser Gly Gly Ser Tyr Thr Tyr Tyr Pro Asp Ser Val
    50                  55                  60

Arg Gly Arg Phe Thr Ile Ser Arg Asp Asn Ala Lys Asn Thr Leu Tyr
65                  70                  75                  80

Leu Gln Met Cys Ser Leu Arg Ser Glu Asp Thr Ala Met Tyr Tyr Cys
                85                  90                  95

Ala Arg Phe Asp Gly Tyr Tyr Ala Met Asp Tyr Trp Gly Gln Gly Thr
            100                 105                 110

Ser Val Thr Val Ser Ser
        115

<210> SEQ ID NO 54
<211> LENGTH: 5
<212> TYPE: PRT
<213> ORGANISM: Mus musculus

<400> SEQUENCE: 54

Ser Tyr Ala Met Ser
1               5

<210> SEQ ID NO 55
<211> LENGTH: 17
<212> TYPE: PRT
<213> ORGANISM: Mus musculus

<400> SEQUENCE: 55

Thr Ile Ser Ser Gly Gly Ser Tyr Thr Tyr Tyr Pro Asp Ser Val Arg
1               5                   10                  15

Gly

<210> SEQ ID NO 56
<211> LENGTH: 9
<212> TYPE: PRT
<213> ORGANISM: Mus musculus

<400> SEQUENCE: 56

Phe Asp Gly Tyr Tyr Ala Met Asp Tyr
1               5

<210> SEQ ID NO 57
<211> LENGTH: 354
<212> TYPE: DNA
<213> ORGANISM: Mus musculus

<400> SEQUENCE: 57
gaagtgcagt tggtggagtc tgggggaggc ttagtgaagc ctggagggtc cctgaaactc      60
tcctgtgcag cctctggatt cactttcagt agctatgcca tgtcttgggc tcgccagact     120
ccggagaaga ggctggagtg gtcgcaacc attagtagtg gtggtagtta cacctactat      180
ccagacagtg tgaggggtcg attcaccatc tccagagaca atgccaagaa cacectgtac     240
```

```
ctgcaaatgt gcagtctgag gtctgaggac acggccatgt attactgtgc aaggtttgat    300
ggttactatg ctatggacta ctggggtcaa ggaacctcag tcaccgtctc ctca          354
```

<210> SEQ ID NO 58
<211> LENGTH: 107
<212> TYPE: PRT
<213> ORGANISM: Mus musculus

<400> SEQUENCE: 58

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Ser Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Ser Leu Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ser Gly Thr Lys Leu Glu Ile Lys
            100                 105

<210> SEQ ID NO 59
<211> LENGTH: 11
<212> TYPE: PRT
<213> ORGANISM: Mus musculus

<400> SEQUENCE: 59

Lys Ala Ser Gln Asp Val Gly Ser Ala Val Ala
1               5                   10

<210> SEQ ID NO 60
<211> LENGTH: 7
<212> TYPE: PRT
<213> ORGANISM: Mus musculus

<400> SEQUENCE: 60

Trp Ala Ser Thr Arg His Thr
1               5

<210> SEQ ID NO 61
<211> LENGTH: 9
<212> TYPE: PRT
<213> ORGANISM: Mus musculus

<400> SEQUENCE: 61

Gln Gln Tyr Ser Ser Tyr Pro Leu Thr
1               5

<210> SEQ ID NO 62
<211> LENGTH: 321
<212> TYPE: DNA
<213> ORGANISM: Mus musculus

<400> SEQUENCE: 62

```
gacattgtga tgacccagtc tcacaaattc atgtccacat cagtcggaga cagggtcagc    60
atcacctgca aggccagtca ggatgtgggt tctgctgtag cctggtatca acagaaacca   120
gggcaatctc ctaaactact gatttactgg gcatccaccc ggcacactgg agtccctgat   180
```

```
cgcttcacag gcagtggatc tgggacagat ttcactctca ccattagcag tttgcagtct      240
gaagacttgg cagattattt ctgtcagcaa tatagcagct atcctctcac gttcggctcg      300
gggacaaagt tggaaataaa a                                                321
```

<210> SEQ ID NO 63
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 63

```
atgaagttgc ctgttaggct gttggtgctg                                       30
```

<210> SEQ ID NO 64
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 64

```
atggagwcag acacactcct gytatgggtg                                       30
```

<210> SEQ ID NO 65
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 65

```
atgagtgtgc tcactcaggt cctggsgttg                                       30
```

<210> SEQ ID NO 66
<211> LENGTH: 33
<212> TYPE: DNA
<213> ORGANISM: Artificial
<220> FEATURE:
<223> OTHER INFORMATION: An artificially synthesized primer sequence

<400> SEQUENCE: 66

```
atgaggrccc ctgctcagwt tyttggmwtc ttg                                   33
```

<210> SEQ ID NO 67
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 67

```
atggatttwc aggtgcagat twtcagcttc                                       30
```

<210> SEQ ID NO 68
<211> LENGTH: 27
<212> TYPE: DNA
<213> ORGANISM: Artificial
<220> FEATURE:
<223> OTHER INFORMATION: An artificially synthesized primer sequence

<400> SEQUENCE: 68

```
atgaggtkcy ytgytsagyt yctgrgg                                          27
```

<210> SEQ ID NO 69

```
<211> LENGTH: 31
<212> TYPE: DNA
<213> ORGANISM: Artificial
<220> FEATURE:
<223> OTHER INFORMATION: An artificially synthesized primer sequence

<400> SEQUENCE: 69
atgggcwtca agatggagtc acakwyycwg g                                      31

<210> SEQ ID NO 70
<211> LENGTH: 31
<212> TYPE: DNA
<213> ORGANISM: Artificial
<220> FEATURE:
<223> OTHER INFORMATION: An artificially synthesized primer sequence

<400> SEQUENCE: 70 atgtgggay ctktttycmm tttttcaatt g                                       31

<210> SEQ ID NO 71
<211> LENGTH: 25
<212> TYPE: DNA
<213> ORGANISM: Artificial
<220> FEATURE:
<223> OTHER INFORMATION: An artificially synthesized primer sequence

<400> SEQUENCE: 71
atggtrtccw casctcagtt ccttg                                             25

<210> SEQ ID NO 72
<211> LENGTH: 27
<212> TYPE: DNA
<213> ORGANISM: Artificial
<220> FEATURE:
<223> OTHER INFORMATION: An artificially synthesized primer sequence

<400> SEQUENCE: 72
atgtatatat gtttgttgtc tatttct                                           27

<210> SEQ ID NO 73
<211> LENGTH: 28
<212> TYPE: DNA
<213> ORGANISM: Artificial
<220> FEATURE:
<223> OTHER INFORMATION: An artificially synthesized primer sequence

<400> SEQUENCE: 73
atggaagccc cagctcagct tctcttcc                                          28

<210> SEQ ID NO 74
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 74
actggatggt gggaagatgg                                                   20

<210> SEQ ID NO 75
<211> LENGTH: 27
<212> TYPE: DNA
<213> ORGANISM: Artificial
<220> FEATURE:
<223> OTHER INFORMATION: An artificially synthesized primer sequence

<400> SEQUENCE: 75
```

```
atgaaatgca gctggggcat sttcttc                                          27

<210> SEQ ID NO 76
<211> LENGTH: 26
<212> TYPE: DNA
<213> ORGANISM: Artificial
<220> FEATURE:
<223> OTHER INFORMATION: An artificially synthesized primer sequence

<400> SEQUENCE: 76
atgggatgga gctrtatcat sytctt                                           26

<210> SEQ ID NO 77
<211> LENGTH: 27
<212> TYPE: DNA
<213> ORGANISM: Artificial
<220> FEATURE:
<223> OTHER INFORMATION: An artificially synthesized primer sequence

<400> SEQUENCE: 77
atgaagwtgt ggttaaactg ggttttt                                          27

<210> SEQ ID NO 78
<211> LENGTH: 25
<212> TYPE: DNA
<213> ORGANISM: Artificial
<220> FEATURE:
<223> OTHER INFORMATION: An artificially synthesized primer sequence

<400> SEQUENCE: 78
atgractttg ggytcagctt grttt                                            25

<210> SEQ ID NO 79
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 79
atggactcca ggctcaattt agttttcctt                                       30

<210> SEQ ID NO 80
<211> LENGTH: 27
<212> TYPE: DNA
<213> ORGANISM: Artificial
<220> FEATURE:
<223> OTHER INFORMATION: An artificially synthesized primer sequence

<400> SEQUENCE: 80
atggctgtcy trgsgctrct cttctgc                                          27

<210> SEQ ID NO 81
<211> LENGTH: 26
<212> TYPE: DNA
<213> ORGANISM: Artificial
<220> FEATURE:
<223> OTHER INFORMATION: An artificially synthesized primer sequence

<400> SEQUENCE: 81
atggratgga gckggrtctt tmtctt                                           26

<210> SEQ ID NO 82
<211> LENGTH: 23
<212> TYPE: DNA
<213> ORGANISM: Artificial
<220> FEATURE:
```

<223> OTHER INFORMATION: An artificially synthesized primer sequence

<400> SEQUENCE: 82
atgagagtgc tgattctttt gtg     23

<210> SEQ ID NO 83
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 83
atggmttggg tgtggamctt gctattcctg     30

<210> SEQ ID NO 84
<211> LENGTH: 27
<212> TYPE: DNA
<213> ORGANISM: Artificial
<220> FEATURE:
<223> OTHER INFORMATION: An artificially synthesized primer sequence

<400> SEQUENCE: 84
atgggcagac ttacattctc attcctg     27

<210> SEQ ID NO 85
<211> LENGTH: 28
<212> TYPE: DNA
<213> ORGANISM: Artificial
<220> FEATURE:
<223> OTHER INFORMATION: An artificially synthesized primer sequence

<400> SEQUENCE: 85
atggattttg ggctgatttt ttttattg     28

<210> SEQ ID NO 86
<211> LENGTH: 27
<212> TYPE: DNA
<213> ORGANISM: Artificial
<220> FEATURE:
<223> OTHER INFORMATION: An artificially synthesized primer sequence

<400> SEQUENCE: 86
atgatggtgt taagtcttct gtacctg     27

<210> SEQ ID NO 87
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 87
cagtggatag actgatgggg g     21

<210> SEQ ID NO 88
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 88
cagtggatag acagatgggg g     21

ANTIBODY AGAINST CALCIFIED GLOBULE AND USE OF THE SAME

RELATED APPLICATION

This application is a nationalization under 35 U.S.C. 371 of PCT/JP2009/054475, filed Mar. 9, 2009 and published as WO 2009/154026 A1 on Dec. 23, 2009, which claimed priority under 35 U.S.C. 119 to Japanese Patent Application No. 2008-162566, filed Jun. 20, 2008; and which claimed priority under 35 U.S.C. 119 to Japanese Patent Application No. 2008-308016, filed Dec. 2, 2008; which applications and publication are incorporated herein by reference in their entirety.

TECHNICAL FIELD

The present invention relates to antibodies against calcified globules; agents comprising the antibodies for inhibiting calcification progression and therapeutic agents for arteriosclerosis; and non-invasive diagnostic methods for arteriosclerosis using the antibodies, such as methods for identifying calcified lesions and methods for monitoring the therapeutic effects.

BACKGROUND ART

Diagnostic methods for assessing the condition of arteriosclerosis, which have already been put to practical use, include, for example, the four methods described below.

"Ankle-brachial pressure index": When blood pressure is measured at the arm and ankle levels in the supine position, the ankle blood pressure is normally slightly higher. However, the narrowing of a blood vessel reduces the downstream blood pressure, which results in a decrease in the ratio of ankle blood pressure to brachial blood pressure (ABI). A decrease in ABI not only indicates arteriosclerosis in the artery of the lower limb but also suggests systemic arteriosclerosis.

"Pulse wave velocity test": A method for estimating the progression of arteriosclerosis by assessing arterial stiffness. In healthy individuals, blood vessels are elastic and thus vascular walls absorb vibration, resulting in a reduction in pulse wave velocity. As arteriosclerosis advances, the wave velocity increases. Thus, the progression of arteriosclerosis can be estimated using the velocity as an indicator.

"Carotid ultrasound examination": A method for estimating the progression of systemic arteriosclerosis by observing carotid arteries which run very close to the surface of skin and have an interior condition that is easy to observe by ultrasound.

"MR angiography (MRA)" and "CT angiography (CTA)": Angiography was used as a major diagnostic imaging method for vascular diseases, but image information that is almost comparable to angiography but obtained in a less invasive manner has become available. The advantages of CTA include: (1) high spatial resolution; (2) simple examination; and (3) superiority in detecting calcified lesions.

The above-described "ankle-brachial pressure index" and "pulse wave velocity test" can neither identify the site of atherosclerosis nor diagnose the progression at each site. Thus, these methods only provide indirect scores to assess arteriosclerosis.

Unlike pulse wave velocity test or such, "carotid ultrasound examination" is superior in that it enables direct graphical observation of the inside of blood vessels. However, the condition of vascular wall is assessed based on the contrasting density and shape in ultrasonic images, and thus clinicians and laboratory technicians who conduct the test are required to have skills. Furthermore, the test cannot identify the site of atherosclerosis or diagnose the progression at individual sites in blood vessels other than the carotid artery.

Back in 1998, Kajander and Ciftcioglu reported that they isolated a class of bacteria, designated "nanobacteria", from human renal calculi (Nanobacteria: an alternative mechanism for pathogenic intra- and extracellular calcification and stone formation. Proc. Natl. Acad. Sci. USA, 1998, Jul. 7; 95(14): 8274-9).

Some research groups, including an NIH group in the U.S., disagreed on the "bacteria". Thus, little is understood about the mechanism that underlies the formation of nanobacteria-like organism (NLO)-derived calcified globules and renal/urinary calculi.

Prior art documents related to the present invention include:
Patent Document 1: Japanese Patent No. 2818658
Patent Document 2: Japanese Patent Application Kokai Publication No. (JP-A) 2004-121152 (unexamined, published Japanese patent application)
Non-patent Document 1: Nanobacteria: an alternative mechanism for pathogenic intra- and extracellular calcification and stone formation. Proc. Natl. Acad. Sci. USA, 1998, Jul. 7; 95(14): 8274-9

DISCLOSURE OF THE INVENTION

Problems to be Solved by the Invention

An objective of the present invention is to provide antibodies against calcified globules; agents comprising the antibodies for inhibiting calcification progression and therapeutic agents for arteriosclerosis; and non-invasive diagnostic methods for arteriosclerosis using the antibodies, such as methods for identifying calcified arteriosclerotic lesions and methods for monitoring the therapeutic effects.

Means for Solving the Problems

Chronic nephritis patients with arteriosclerosis in microvessels at local sites of the kidney are often positive for oxidized LDL/$\beta_2$GPI complex. Meanwhile, urinary calculi are in many cases considered a "renal pathological condition generated in association with lifestyle-related diseases". The formation of "stone" (in particular, apatite formation) is in general explained by endocrine metabolic disorders associated with phosphorus and calcium.

However, based on the idea that the oxidative stress (lipid peroxidation), which is a cause of lifestyle-related disease, is responsible for both "arterial calcification in association with atherosclerosis" and "formation of urinary calculus", the present inventors started component analysis of the calculi and arterial calcified lesions. Furthermore, antibodies that specifically bind to calcified globule were prepared by immunization with renal calculus-derived calcified globules or carotid artery-derived arteriosclerotic plaques, followed by screening with calcified globules. Then, the antibodies were revealed to be slightly different in reactivity to various lipids (phosphatidylserine, cardiolipin, and 7-ketocholesteryl-9-carboxynonanoate (also referred to as 9-oxo-9-(7-ketoch-oest-5-en-3β-yloxy) nonanoic acid)), and oxidized LDL.

Specifically, calcified globules derived from human renal calculi were incubated in DMEM supplemented with 10% FCS, and the resulting calcified globules were collected by centrifugation. With the calcified globules (nanobacteria-like organism (NLO)), BALB/c mice were subcutaneously immunized several times using Freund's adjuvant. By the polyethylene glycol method, the resulting spleen cells were fused with cells of the myeloma line P3U1 to produce monoclonal antibodies. The prepared monoclonal antibodies were tested and assessed for their binding to calcified atherosclerotic lesions. The result showed that the antibodies exhibited binding activity.

In addition, with homogenate of arteriosclerotic plaques derived from human abdominal aorta, BALB/c mice were subcutaneously immunized several times using Freund's adjuvant in the same manner. By the polyethylene glycol method, the resulting spleen cells were fused with cells of the myeloma line P3U1 to produce monoclonal antibodies. Clones were analyzed by ELISA to identify clones reactive to the oxidative stress (i.e., lipid peroxides) which is a cause of lifestyle-related diseases. Antibodies reactive in ELISA were tested to assess whether they bind to arteriosclerotic lesions. The result showed that the antibodies exhibited binding activity.

Then, monoclonal antibodies established from mice immunized with calcified globules were assessed for their effect on the formation of lamella (lipid membrane-like structure). The monoclonal antibodies were found to inhibit lamellar formation.

Specifically, the antibodies of the present invention are reactive to calcified globules and have the activity of binding to arteriosclerotic plaques (in particular, calcified arteriosclerotic lesions).

Based on the idea that oxidative stress (lipid peroxidation), which is a cause of lifestyle-related disease, is responsible for both "arterial calcification in association with atherosclerosis" and "formation of urinary calculus", the present inventors further assessed the antibodies in this context. The antibodies were found to include those having the activity to bind to at least one selected from the group consisting of oxidized LDL, phosphatidylserine, cardiolipin, and 7-ketocholesteryl-9-carboxynonanoate. As specifically described in the Examples herein, clones CL15 and C19 isolated in the present invention bind to arteriosclerotic lesions and also have the activity of binding to oxidized LDL, phosphatidylserine, cardiolipin, and 7-ketocholesteryl-9-carboxynonanoate.

On the other hand, CL21 was demonstrated to bind to arteriosclerotic lesions and have the activity of binding to cardiolipin and 7-ketocholesteryl-9-carboxynonanoate. CL48 and CL56 bound to arteriosclerotic lesions, but did not bind to any of oxidized LDL, phosphatidylserine, cardiolipin, and 7-ketocholesteryl-9-carboxynonanoate.

Furthermore, the present inventors demonstrated that the antibodies specifically react to arteriosclerotic lesions (calcified lesions), and achieved visualization of calcified arteriosclerotic lesions using the fluorescently labeled antibodies.

Moreover, double-staining experiments were carried out using antibodies of the present invention and antibodies against oxidized LDL/$\beta_2$GPI complex. When pathological tissue sections were contacted with both antibody 3H3 and an antibody of the present invention that recognizes calcified globules, their fluorescent labels each recognized a different tissue site in the sections. Thus, it was demonstrated that the antibodies could be used to identify different types of lesions on tissue sections.

Specifically, the present invention provides:

[1] an antibody which is reactive to a calcified globule (NLO) and has the activity of binding to an atherosclerotic plaque;

[2] the antibody of [1], which additionally has the activity of binding to at least any one selected from the group consisting of LDL oxidatively modified by copper sulfate (oxidized LDL), phosphatidylserine, cardiolipin, and 7-ketocholesteryl-9-carboxynonanoate (9-oxo-9-(7-ketochoest-5-en-3β-yloxy) nonanoic acid);

[3] the antibody of [2], which additionally has the activity of binding to oxidized LDL, phosphatidylserine, cardiolipin, and 7-ketocholesteryl-9-carboxynonanoate;

[4] the antibody of [2], which additionally has the activity of binding to cardiolipin and 7-ketocholesteryl-9-carboxynonanoate;

[5] the antibody of [1], which is reactive to a calcified globule in ELISA but is not reactive to at least one selected from the group consisting of LDL oxidatively modified by copper sulfate (oxidized LDL), phosphatidylserine, cardiolipin, and 7-ketocholesteryl-9-carboxynonanoate;

[6] the antibody of [1] or [2], which is the antibody of any one of:

(a) an antibody comprising a heavy chain that comprises CDR1 having the amino acid sequence of SEQ ID NO: 1, CDR2 having the amino acid sequence of SEQ ID NO: 2, and CDR3 having the amino acid sequence of SEQ ID NO: 3;

(b) an antibody comprising a heavy chain that comprises a heavy-chain variable region having the amino acid sequence of SEQ ID NO: 4;

(c) an antibody comprising a light chain that comprises CDR1 having the amino acid sequence of SEQ ID NO: 6, CDR2 having the amino acid sequence of SEQ ID NO: 7, and CDR3 having the amino acid sequence of SEQ ID NO: 8;

(d) an antibody comprising a light chain that comprises a light-chain variable region having the amino acid sequence of SEQ ID NO: 9;

(e) an antibody that comprises a pair of the heavy chain of (a) or (b) above and the light chain of (c) or (d) above;

(f) an antibody comprising a heavy chain that comprises CDR1 having the amino acid sequence of SEQ ID NO: 11, CDR2 having the amino acid sequence of SEQ ID NO: 12, and CDR3 having the amino acid sequence of SEQ ID NO: 13;

(g) an antibody comprising a heavy chain that comprises a heavy-chain variable region having the amino acid sequence of SEQ ID NO: 14;

(h) an antibody comprising a light chain that comprises CDR1 having the amino acid sequence of SEQ ID NO: 16, CDR2 having the amino acid sequence of SEQ ID NO: 17, and CDR3 having the amino acid sequence of SEQ ID NO: 18;

(i) an antibody comprising a light chain that comprises a light-chain variable region having the amino acid sequence of SEQ ID NO: 19; and (j) an antibody that comprises a pair of the heavy chain of (f) or (g) above and the light chain of (h) or (i) above;

[7] the antibody of [1] or [3], which is the antibody of any one of:

(a) an antibody comprising a heavy chain that comprises CDR1 having the amino acid sequence of SEQ ID NO: 21, CDR2 having the amino acid sequence of SEQ ID NO: 22, and CDR3 having the amino acid sequence of SEQ ID NO: 23;

(b) an antibody comprising a heavy chain that comprises a heavy-chain variable region having the amino acid sequence of SEQ ID NO: 24;

(c) an antibody comprising a light chain that comprises CDR1 having the amino acid sequence of SEQ ID NO: 26, CDR2 having the amino acid sequence of SEQ ID NO: 27, and CDR3 having the amino acid sequence of SEQ ID NO: 28;

(d) an antibody comprising a light chain that comprises a light-chain variable region having the amino acid sequence of SEQ ID NO: 29; and (e) an antibody that comprises a pair of the heavy chain of (a) or (b) above and the light chain of (c) or (d) above;

[8] the antibody of [1], which is the antibody of any one of:

(a) an antibody comprising a heavy chain that comprises CDR1 having the amino acid sequence of SEQ ID NO: 31, CDR2 having the amino acid sequence of SEQ ID NO: 32, and CDR3 having the amino acid sequence of SEQ ID NO: 33;

(b) an antibody comprising a heavy chain that comprises a heavy-chain variable region having the amino acid sequence of SEQ ID NO: 34;

(c) an antibody comprising a light chain that comprises CDR1 having the amino acid sequence of SEQ ID NO: 36, CDR2 having the amino acid sequence of SEQ ID NO: 37, and CDR3 having the amino acid sequence of SEQ ID NO: 38;

(d) an antibody comprising a light chain that comprises a light-chain variable region having the amino acid sequence of SEQ ID NO: 39;

(e) an antibody that comprises a pair of the heavy chain of (a) or (b) above and the light chain of (c) or (d) above;

(f) an antibody comprising a heavy chain that comprises CDR1 having the amino acid sequence of SEQ ID NO: 41, CDR2 having the amino acid sequence of SEQ ID NO: 42, and CDR3 having the amino acid sequence of SEQ ID NO: 43;

(g) an antibody comprising a heavy chain that comprises heavy-chain variable region having the amino acid sequence of SEQ ID NO: 44;

(h) an antibody comprising a light chain that comprises CDR1 having the amino acid sequence of SEQ ID NO: 46, CDR2 having the amino acid sequence of SEQ ID NO: 47, and CDR3 having the amino acid sequence of SEQ ID NO: 48;

(i) an antibody comprising a light chain that comprises a light-chain variable region having the amino acid sequence of SEQ ID NO: 49; and (j) an antibody that comprises a pair of the heavy chain of (f) or (g) above and the light chain of (h) or (i) above;

[9] an antibody that binds to the same epitope as the antibody of any one of [1] to [8];

[10] the antibody of any one of [1] to [9], which is a humanized or chimeric antibody;

[11] an imaging agent for visualizing a calcified arteriosclerotic site, which comprises the antibody of any one of [1] to [10];

[12] an imaging kit for visualizing a calcified arteriosclerotic site, which comprises the antibody of any one of [1] to [10];

[13] a method for producing the antibody of any one of [1] to [10], which comprises the steps of:

(a) immunizing a nonhuman animal with a calcified globule or atherosclerotic plaque; and (b) isolating an antibody from the nonhuman animal;

[14] an antibody-producing method, which additionally comprises after the step of (b) in [13], the step of: (c) selecting and isolating an antibody that binds specifically to a calcified globule via screening with a calcified globule;

[15] an antibody-producing method, which additionally comprises after the step of (c) in [14], the steps of: (d) continuing culture after adding the antibody to a culture medium of a calcified globule; and (e) selecting and isolating an antibody that inhibits the growth of a calcified globule as compared to that of a control;

[16] an agent for inhibiting the growth of a calcified globule, which comprises an antibody produced by the method of [13] or [14];

[17] an agent for inhibiting the growth of a calcified globule, which comprises an antibody that comprise:

a heavy chain of either an antibody comprising a heavy chain that comprises CDR1 having the amino acid sequence of SEQ ID NO: 21, CDR2 having the amino acid sequence of SEQ ID NO: 22, and CDR3 having the amino acid sequence of SEQ ID NO: 23; or an antibody comprising a heavy-chain variable region having the amino acid sequence of SEQ ID NO: 24; and a light chain of either an antibody comprising a light chain that comprises CDR1 having the amino acid sequence of SEQ ID NO: 26, CDR2 having the amino acid sequence of SEQ ID NO: 27, and CDR3 having the amino acid sequence of SEQ ID NO: 28; or an antibody comprising a light chain that comprises a light-chain variable region having the amino acid sequence of SEQ ID NO: 29;

[18] a method for inhibiting the growth of a calcified globule, which uses an antibody produced by the production method of [13] or [14];

[19] use of an antibody produced by the production method of [13] or [14] in manufacturing an agent for inhibiting the growth of a calcified globule;

[20] an antibody produced by the production method of [13] or [14], which is to be used in a method for inhibiting the growth of a calcified globule;

[21] a method of screening for a candidate compound for a therapeutic agent for arteriosclerosis, which comprises the steps of:

(a) administering a candidate compound to an arteriosclerosis model nonhuman animal administered with the antibody of any one of [1] to [10];

(b) carrying out imaging of an arteriosclerotic plaque in an arteriosclerosis model nonhuman animal administered with the candidate compound and in an arteriosclerosis model nonhuman animal not administered with the candidate compound;

(c) comparing the size or location of an arteriosclerotic plaque between the arteriosclerosis model nonhuman animal administered with the candidate compound and the arteriosclerosis model nonhuman animal not administered with the candidate compound; and (d) selecting a candidate compound that reduces or eliminates an arteriosclerotic plaque in the arteriosclerosis model nonhuman animal administered with the candidate compound as compared to the arteriosclerosis model nonhuman animal not administered with the candidate compound;

[22] a kit for immunologically detecting a calcification site and an arteriosclerosis site in an atherosclerotic plaque, which comprises the antibody of any one of [1] to [10] and an antibody that binds to a complex of oxidized LDL and $\beta_2$-glycoprotein I (oxidized LDL/$\beta_2$GPI complex);

[23] an immunological method, which comprises the steps of:

(a) contacting an isolated arteriosclerotic plaque with the antibody of any one of [1] to [10] and an antibody that binds to an oxidized LDL/$\beta_2$GPI complex; and (b) detecting a calcification site and an arteriosclerosis site in the arteriosclerotic plaque;

[24] an imaging method for visualizing an arteriosclerotic calcification site, which comprises the antibody of any one of [1] to [10];

[25] use of the antibody of any one of [1] to [10] in manufacturing an imaging agent for visualizing a calcified arteriosclerotic site;

[26] the antibody of any one of [1] to [10], which is to be used in an imaging method for visualizing a calcified arteriosclerotic site; and

[27] a method for detecting a pathological condition due to arteriosclerosis, which comprises the steps of:

(a) contacting an arteriosclerotic plaque with the antibody of any one of [1] to [10] and an antibody that binds to an oxidized LDL/$\beta_2$GPI complex;

(b) detecting a calcification site and an atheroma of arteriosclerosis, or early lesion thereof in the arteriosclerotic plaque; and (c) assessing whether an arteriosclerotic plaque is detected by the antibody of any one of [1] to [10] or an antibody that binds to an oxidized LDL/$\beta_2$GPI complex.

BRIEF DESCRIPTION OF THE DRAWINGS

FIG. 7 is a diagram showing the amino acid sequences of antibodies. The diagrams show the CDR amino acid sequences of respective anti-calcified globule antibodies with high legibility. There is almost no homologous region in the sequences.

FIGS. 9A, B and C are photographs showing in vivo images obtained using Cy5.5-labeled antibody (IgM: anti-calcified globule antibody).

(A) An illustration that indicates the procedure for preparing cryosections of mouse aortic valve.

(B) Hematoxylin-eosin staining of mouse aortic valve.

(C) Oil red straining of mouse aortic valve.

(D) to (H) fluorescent immunostaining of mouse aortic valve.

(D) Staining was carried out using the following primary antibodies: rat anti-mouse monocyte/macrophage antibody MOMA-2 (BMA BIOMEDICALS; 1 µg/ml) and rabbit anti-α smooth muscle actin antibody (Abcam; 6 µg/ml). An image obtained using U-MNIBA2 filter for FITC fluorescence was superimposed with an image obtained using U-MWIG2 filter for Rhodamine fluorescence.

(E) Staining was carried out using DAPI and Cy5.5-labeled antibody CL15 (100 µg/ml). An image obtained using U-MNU2 filter for DAPI was superimposed with an image obtained using U-MWIG2 filter for Rhodamine.

(F) Staining was carried out using DAPI and Alexa Fluor488-labeled antibody 3H3 (25 μg/ml). An image obtained using U-MNU2 filter was superimposed with an image obtained using U-MNIBA2 filter for FITC.

(G) Staining was carried out using Cy5.5-labeled antibody CL15 (100 μg/ml) and Alexa Fluor488-labeled antibody 3H3 (25 μg/ml). An image obtained using U-MNIBA2 filter for FITC was superimposed with an image obtained using U-MWIG2 filter for Rhodamine. Overlapping areas become colored yellow.

(H) Staining was carried out using, in combination with DAPI, a rabbit anti-osteocalcin antibody (Santa Cruz; 4 μg/ml) as the primary antibody and a Rhodamine-labeled donkey anti-rabbit IgG antibody (Santa Cruz; 4 μg/ml) as the secondary antibody. An image obtained using U-MNU2 filter for DAPI was superimposed with an image obtained using U-MWIG2 filter for Rhodamine.

Figure 17:
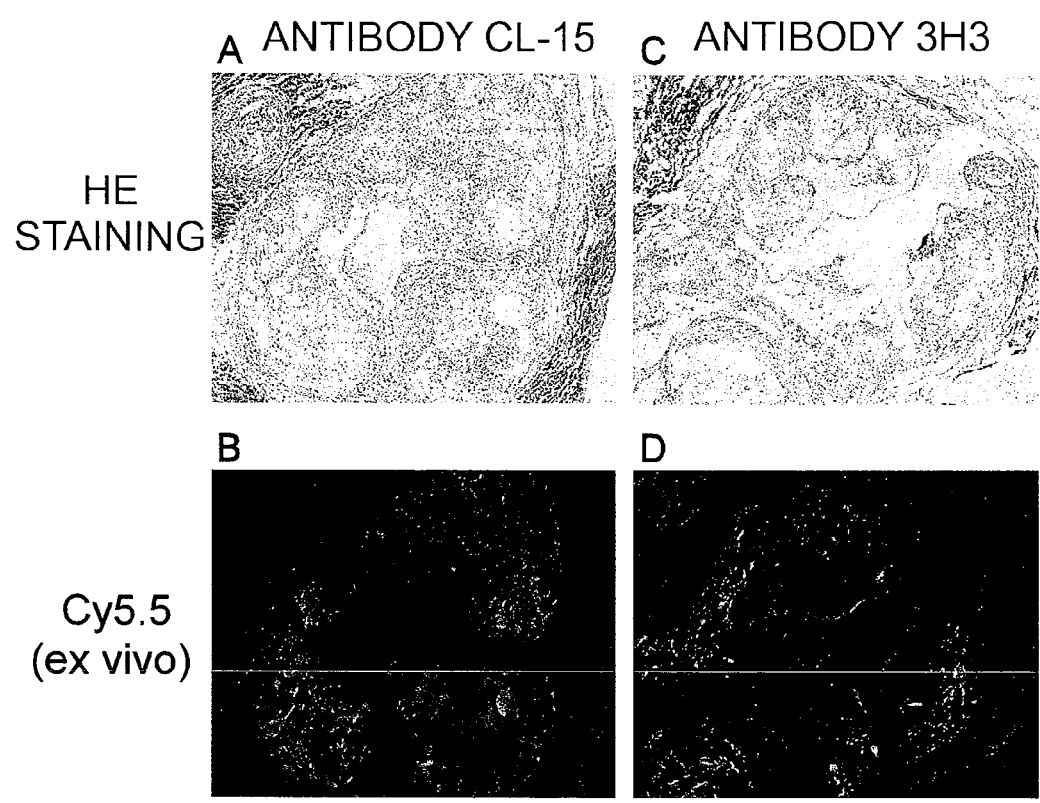

FIG. 17 is photographs showing the aortic valves of apoE$^{-/-}$ mice administered with a Cy5.5-labeled antibody at the caudal vein. Cy5.5 fluorescence from the Cy5.5-labeled antibodies (B, florescence of Cy5.5-labeled antibody CL-15; D, florescence of Cy5.5-labeled antibody 3H3) was observed and photographed. The identical sections were also stained with hematoxylin/eosin (A and B).

Figure 18:
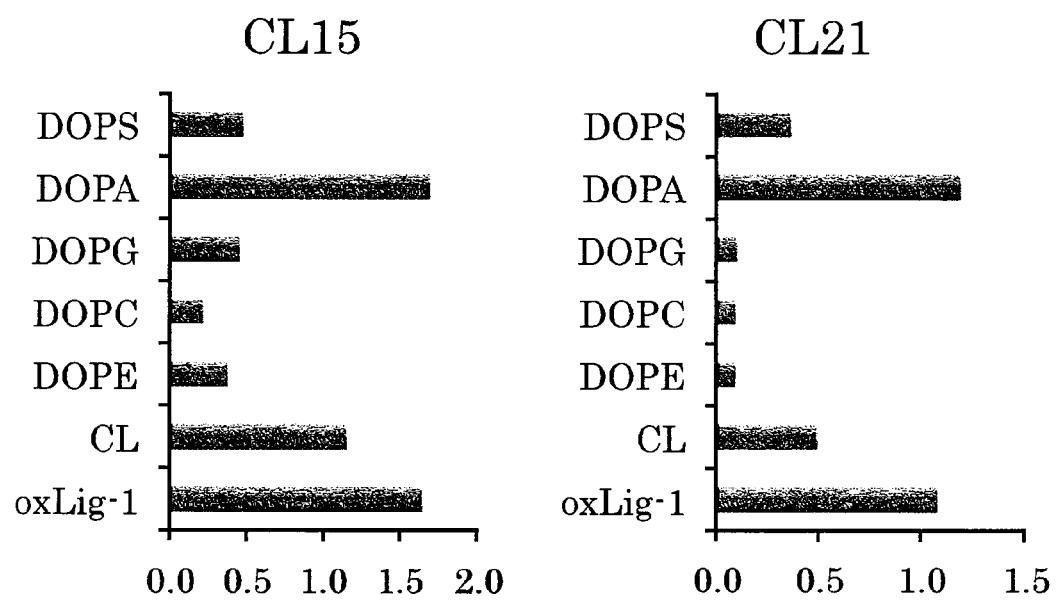

FIG. 18 is a diagram showing the reactivity of antibody CL 15 to various lipids in ELISA.

FIG. 19A to G are photographs showing the reactivity of antibody CL15 to various lipids in TLC-Ligand blotting.

Figure 20:
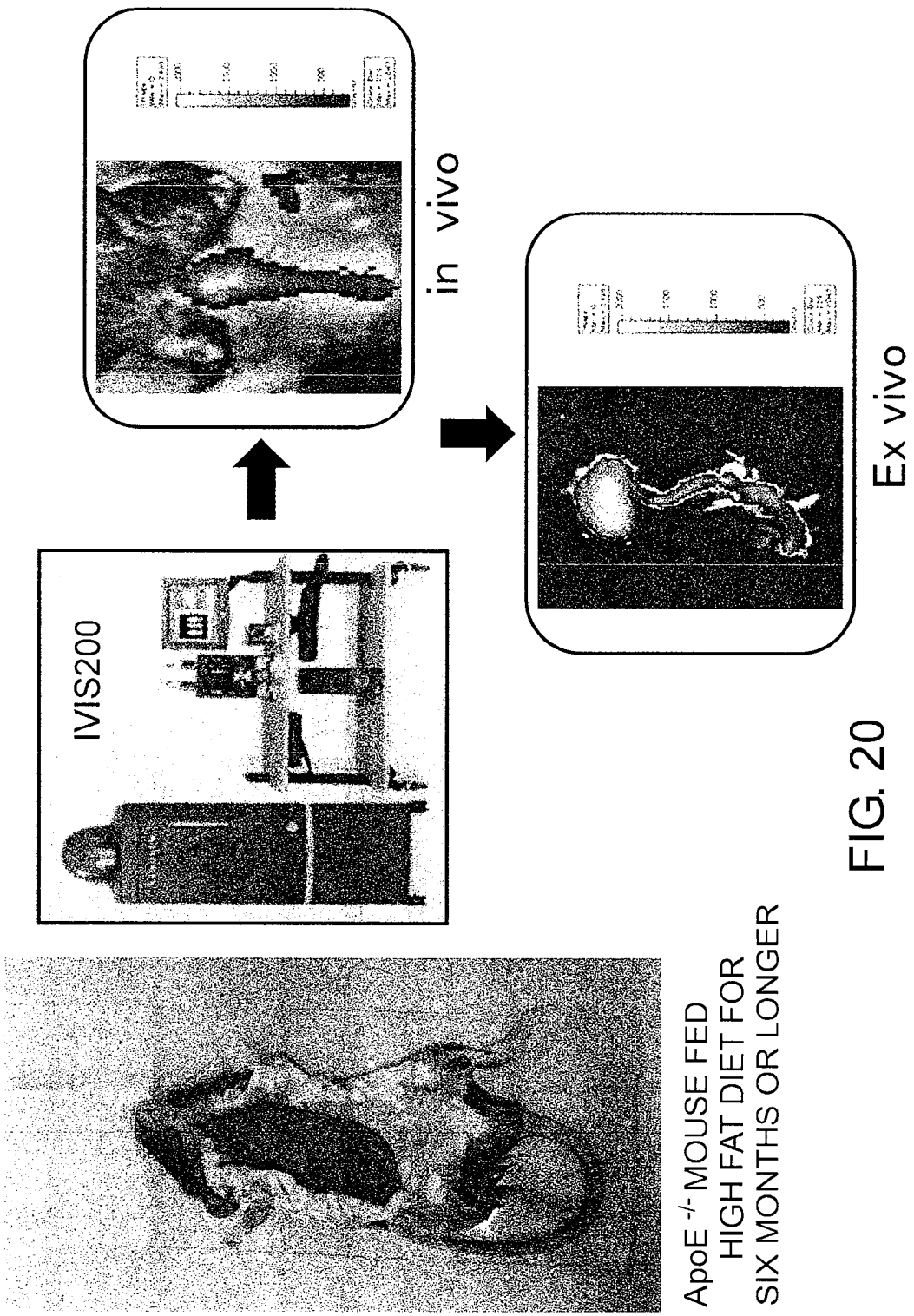

FIG. 20 is photographs showing IVIS 200 fluorescence imaging using specific antibody (reflection fluorescence microscopy). In vivo: ApoE$^{-/-}$ mice were fed a high fat diet for six months or more. Imaging agents were administered to the mice at the caudal vein. After two to 24 hours, in vivo fluorescence was observed and photographed under inhalation anesthesia using IVIS 200. The ApoE$^{-/-}$ mice were observed after shaving, because their black hair absorbs fluorescence. Ex vivo: Mice euthanized were thoracotomized. The heart and aorta were exposed, and a small incision was made in the right auricular appendage. Then, a needle was inserted into the left ventricle and the heart was perfused with 10 ml of cold PBS. The heart and aorta were excised and their reflection fluorescence microscopic images were recorded using IVIS 200.

FIG. 21 is photographs showing IVIS 200 fluorescence imaging (excitation, 640 nm; emission, 720 nm). Experiment 1: physiological saline (PBS; control), Cy5.5-labeled antibody A, or Cy5.5-labeled antibody 3H3 was administered at the caudal vein to apoE$^{-/-}$ mice fed a high fat diet. Twenty four hours after administration, the mice were photographed alive for the full-body image after removing their thoracic skin. Then, the heart intact with thoracic aorta was excised and photographed. Experiment 2: Hearts and aortae excised from mice administered with PBS, Cy5.5-labeled antibody 2A12, or y5.5-labeled antibody 3H3. Administered 3H3 intensely stained the aortic root. Antibody A also stained to some extent; however, the fluorescence intensity is weaker as compared to 3H3. There was no stain in the case of 2A12.

Figure 22:
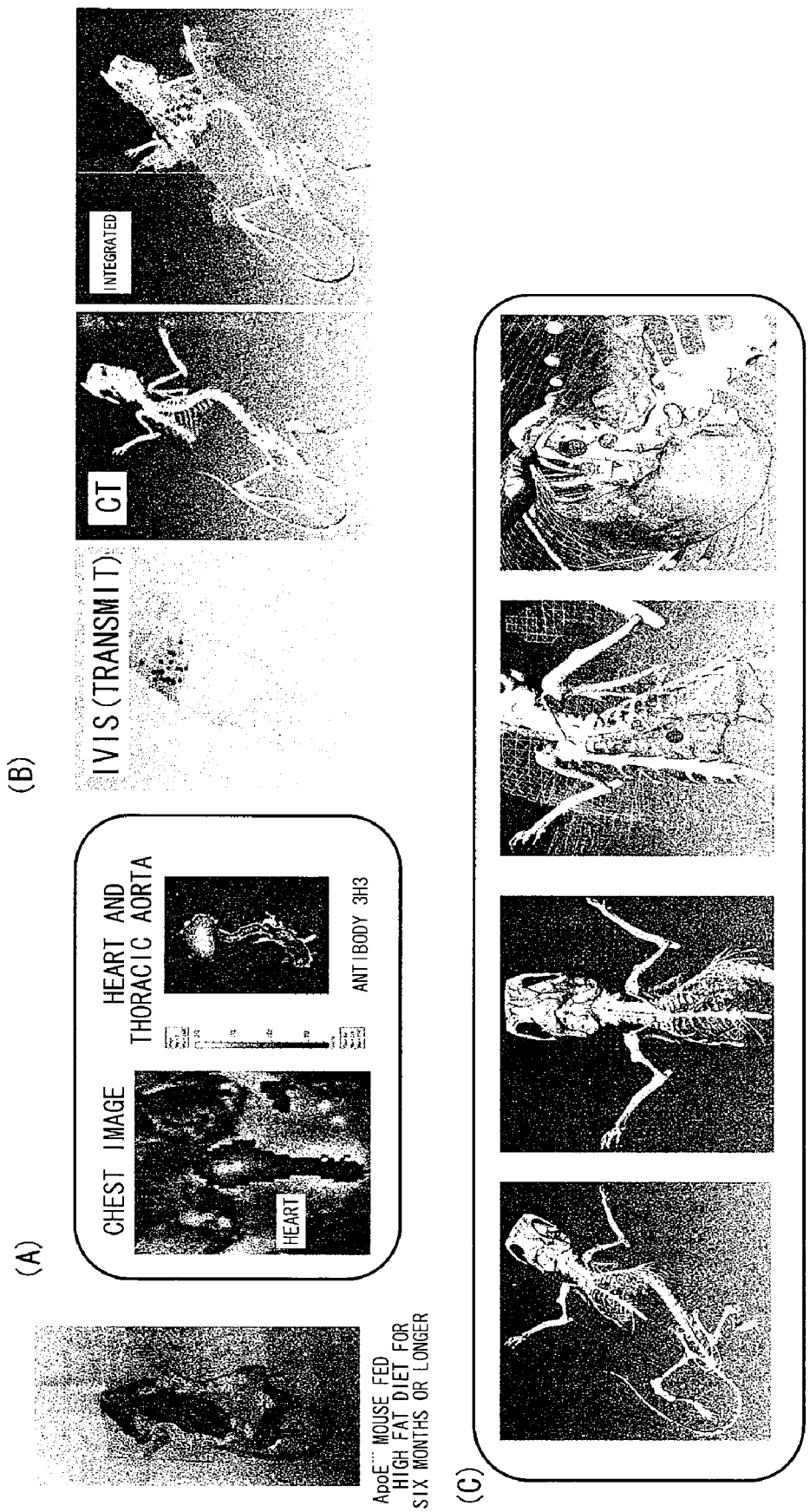

FIG. 22 is photographs showing three-dimensional imaging of arteriosclerosis using the specific antibody. (A), IVIS 200 fluorescence imaging using the specific antibody (reflection fluorescence microscopy); (B), IVIS 200 3D image obtained using transmitted light (left panel), CT 3D image before superimposing (middle panel), and the superimposed 3D image (right panel); (C) superimposed 3D images generated from IVIS fluorescence signal and 3D CT.

FIG. 23 is photographs showing IVIS 200 fluorescence three-dimensional images before superimposing (upper panels, A) and superimposed images generated from IVIS 200 fluorescence signal and 3D CT (bottom panels, B).

Figure 24:
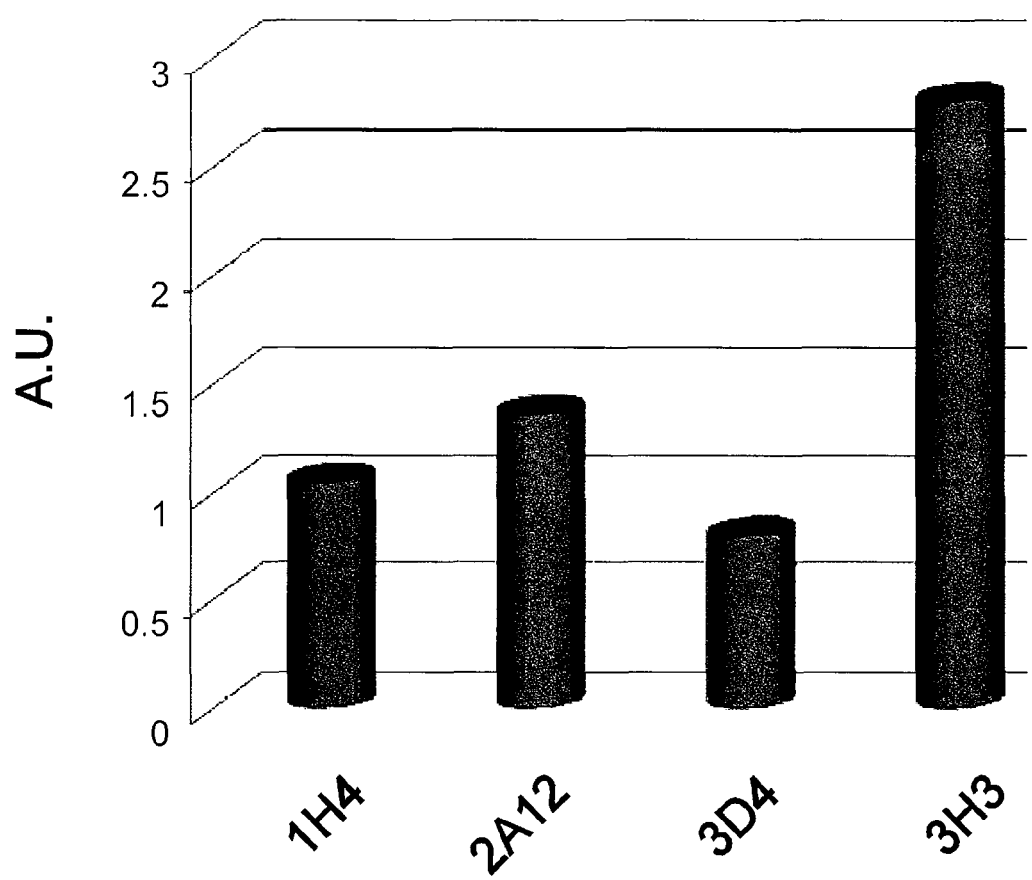

FIG. 24 is a diagram showing fluorescence intensity of Cy5.5 around the aortic root observed using IVIS 200. The fluorescence intensity was determined per unit area of the aortic root. The fluorescence of PBS-administered control mouse was taken as 1.0. When 3H3 was administered, fluorescence was three times stronger than the control. When other antibodies were administered, there was no significant change in the fluorescence intensity.

FIG. 25 is a diagram showing the amino acid sequence of antibody 3H3. Each CDR is underlined.

MODE FOR CARRYING OUT THE INVENTION

The present invention provides antibodies that are reactive to calcified globules and have the activity of binding to arteriosclerotic plaques (in particular, calcified arteriosclerotic lesions). Arteriosclerotic plaques include calcified arteriosclerotic lesions, arteriosclerotic atheroma, and their early lesions. Thus, the present invention includes antibodies that bind to calcified globules and calcified arteriosclerotic lesions. The present invention also includes antibodies that bind to calcified globules and arteriosclerotic atheroma. The phrase "antibody is reactive to calcified globules" is interchangeable with "antibody binds to calcified globules".

Calcified globules (NLO) are prepared as follows. Renal/urinary calculi were isolated by surgical excision. After crushing, the calculi were dissolved with acid. Following neutralization, the solution was filtered through a filter for sterilization, and incubated in a medium (Dulbecco's modified MEM) containing 10% FCS (or FBS; preferably gamma-irradiated) under 5% $CO_2$ at 37° C. as in cell culture. It is preferable to disperse the precipitate in the medium by sonication before this "culturing". This culturing treatment can amplify calcified globules. For example, according to the document "Nanobacteria: an alternative mechanism for pathogenic intra- and extracellular calcification and stone formation. Proc. Natl. Acad. Sci. USA 1998, Jul. 7; 95(14): 8274-9", the Nanobacterium (NNb) line (gift from Dr. Neva Ciftcioglu (NASA, USA)) is incubated under 5% $CO_2$ at 37° C. in DMEM containing 10% FBS irradiated with γ-ray, and can be continuously subcultured while being monitored under a phase contrast microscope. However, calcified globules can also be prepared from urinary calculi, renal calculi, and the like, derived from various patients. Thus, the method for preparing calcified globules is not limited to the above example.

The growth of calcified globules can be assessed based on an increase in turbidity at 650 nm, or an increase in the particle size of membrane-like (lamella) structure and/or an increase in the number of lamellae under a phase contrast microscope. Calcified globules can be isolated and collected as a precipitate from culture medium by low-speed centrifugation at 20° C. (for example, centrifugation at 3,000 to 10,000 rpm for 30 to 60 minutes).

Arteriosclerotic plaques and calcified arteriosclerotic lesions can be obtained by surgical resection from patients with arteriosclerosis confirmed in the thoracic and abdominal aorta, or carotid artery. Alternatively, arteriosclerotic plaques and calcified arteriosclerotic lesions can be prepared experimentally by excising aortic valve (aortic root), or thoracic and abdominal aorta from apoE-deficient (apoE$^{-/-}$) or LDL receptor-deficient (LDLR$^{-/-}$) mice (hyperlipidemia model mice) fed a high fat diet.

The calcified lesion refers to vascular wall deposit resulting from chelating of blood calcium into a form of calcium phosphate. In arteriosclerosis, atheroma sometimes leads to calcified lesion, resulting in aging and hardening of vascular walls due to loss of elasticity.

Antibodies of the present invention can be obtained by immunizing nonhuman animals with calcified globules (NLO) or arteriosclerotic plaques. When calcified globules are used as an immunogen, the animal species is not particularly limited, as long as the calcified globules are derived from renal calculi. The preferred animal species includes human. Alternatively, when homogenate of arteriosclerotic plaques is used as an immunogen, the site and animal species are not particularly limited, and arteriosclerotic plaques from human abdominal aorta or the like can be used. It is preferable that antibody clones are selected using as an indicator the reactivity to calcified globules regardless of the type of immunogen used. Antibodies prepared by such a method may be non-reactive to lipid peroxides such as oxidized LDL, phosphatidylserine, cardiolipin, and 7-ketocholesteryl-9-carboxynonanoate (also referred to as 9-oxo-9-(7-ketochoest-5-en-3β-yloxy) nonanoic acid), or reactive to lipid peroxides, as long as they have the activity to bind to calcified arteriosclerotic lesions.

Thus, the present invention includes antibodies that have the activity to bind to at least one selected from the group consisting of LDL oxidatively modified by copper sulfate (oxidized LDL), phosphatidylserine, cardiolipin, and 7-ketocholesteryl-9-carboxynonanoate (also referred to as 9-oxo-9-(7-ketochoest-5-en-3β-yloxy) nonanoic acid); antibodies that have the activity to bind to oxidized LDL, phosphatidylserine, cardiolipin, and 7-ketocholesteryl-9-carboxynonanoate; and antibodies that have the activity to bind to cardiolipin and 7-ketocholesteryl-9-carboxynonanoate.

Furthermore, the antibodies of the present invention include antibodies that are detected by ELISA to have reactivity towards calcified globules, but not to have reactivity towards at least one selected from the group consisting of LDL oxidatively modified by copper sulfate (oxidized LDL), phosphatidylserine, cardiolipin, and 7-ketocholesteryl-9-carboxynonanoate. "Detected by ELISA to have reactivity towards calcified globules" means that ELISA is used to determine that an antibody binds to calcified globules. Specifically, "binds" means that an antibody is judged to bind to calcified globules as compared to a negative control antibody.

In ELISA, 96-well micro test plates are immobilized with calcified globules (NLO) isolated or amplified from human renal/urinary calculi in the manner described above; plasma LDL oxidatively modified by copper sulfate; or 7-ketocholesteryl-9-carboxynonanoate, which is synthesized from 7-ketocholesterol and azelaic acid, or purified from, for example, phosphatidylserine derived from bovine brain, or cardiolipin or oxidized LDL derived from bovine heart. Antibodies reactive to the immobilized antigen can be detected using an anti-immunoglobulin antibody labeled with an enzyme such as HRP.

The antibodies of the present invention can be used in drug delivery systems (DDS), or in targeted therapy based on their own neutralizing activity. Such antibodies include, for example, antibodies of the present invention linked to drug-encapsulating liposomes. Inflammation and immune reaction at local sites of arteries, which are potential causes of arteriosclerosis, can be suppressed by administering antibodies of the present invention linked to drug-encapsulating liposomes in vivo. Such drugs include, for example, statin (HMG-CoA reductase inhibitor) and immunosuppressants (rapamycin, paclitaxel, etc).

Specifically, the antibodies of the present invention include those described below, but are not limited thereto:

(a) an antibody comprising a heavy chain that comprises CDR1 having the amino acid sequence of SEQ ID NO: 1, CDR2 having the amino acid sequence of SEQ ID NO: 2, and CDR3 having the amino acid sequence of SEQ ID NO: 3;

(b) an antibody comprising a heavy chain that comprises a heavy-chain variable region having the amino acid sequence of SEQ ID NO: 4;

(c) an antibody comprising a light chain that comprises CDR1 having the amino acid sequence of SEQ ID NO: 6, CDR2 having the amino acid sequence of SEQ ID NO: 7, and CDR3 having the amino acid sequence of SEQ ID NO: 8;

(d) an antibody comprising a light chain that comprises a light-chain variable region having the amino acid sequence of SEQ ID NO: 9;

(e) an antibody comprising a pair of the heavy chain of (a) or (b) above and the light chain (c) or (d) above;

(f) an antibody comprising a heavy chain that comprises CDR1 having the amino acid sequence of SEQ ID NO: 11, CDR2 having the amino acid sequence of SEQ ID NO: 12, and CDR3 having the amino acid sequence of SEQ ID NO: 13;

(g) an antibody comprising a heavy chain that comprises a heavy-chain variable region having the amino acid sequence of SEQ ID NO: 14;

(h) an antibody comprising a light chain that comprises CDR1 having the amino acid sequence of SEQ ID NO: 16, CDR2 having the amino acid sequence of SEQ ID NO: 17, and CDR3 having the amino acid sequence of SEQ ID NO: 18;

(i) an antibody comprising a light chain that comprises a light-chain variable region having the amino acid sequence of SEQ ID NO: 19;

(j) an antibody comprising a pair of the heavy chain of (f) or (g) above and the light chain (h) or (i) above;

(k) an antibody comprising a heavy chain that comprises CDR1 having the amino acid sequence of SEQ ID NO: 21, CDR2 having the amino acid sequence of SEQ ID NO: 22, and CDR3 having the amino acid sequence of SEQ ID NO: 23;

(l) an antibody comprising a heavy chain that comprises a heavy-chain variable region having the amino acid sequence of SEQ ID NO: 24;

(m) an antibody comprising a light chain that comprises CDR1 having the amino acid sequence of SEQ ID NO: 26, CDR2 having the amino acid sequence of SEQ ID NO: 27, and CDR3 having the amino acid sequence of SEQ ID NO: 28;

(n) an antibody comprising a light chain that comprises a light-chain variable region having the amino acid sequence of SEQ ID NO: 29;

(o) an antibody comprising a pair of the heavy chain of (k) or (l) above and the light chain (m) or (n) above;

(p) an antibody comprising a heavy chain that comprises CDR1 having the amino acid sequence of SEQ ID NO: 31, CDR2 having the amino acid sequence of SEQ ID NO: 32, and CDR3 having the amino acid sequence of SEQ ID NO: 33;

(q) an antibody comprising a heavy chain that comprises a heavy-chain variable region having the amino acid sequence of SEQ ID NO: 34;

(r) an antibody comprising a light chain that comprises CDR1 having the amino acid sequence of SEQ ID NO: 36, CDR2 having the amino acid sequence of SEQ ID NO: 37, and CDR3 having the amino acid sequence of SEQ ID NO: 38;

(s) an antibody comprising a light chain that comprises a light-chain variable region having the amino acid sequence of SEQ ID NO: 39;

(t) an antibody comprising a pair of the heavy chain of (p) or (q) above and the light chain of (r) or (s) above;

(u) an antibody comprising a heavy chain that comprises CDR1 having the amino acid sequence of SEQ ID NO: 41, CDR2 having the amino acid sequence of SEQ ID NO: 42, and CDR3 having the amino acid sequence of SEQ ID NO: 43;

(v) an antibody comprising a heavy chain that comprises a heavy-chain variable region having the amino acid sequence of SEQ ID NO: 44;

(w) an antibody comprising a light chain that comprises CDR1 having the amino acid sequence of SEQ ID NO: 46, CDR2 having the amino acid sequence of SEQ ID NO: 47, and CDR3 having the amino acid sequence of SEQ ID NO: 48;

(x) an antibody comprising a light chain that comprises a light-chain variable region having the amino acid sequence of SEQ ID NO: 49; and (y) an antibody comprising a pair of the heavy chain of (u) or (v) above and the light chain of (w) or (x) above.

Furthermore, the present invention provides antibodies that bind to the same epitope as an antibody of the present invention that binds to calcified globules and calcified arteriosclerotic lesions.

Whether an antibody recognizes the same epitope as another antibody can be confirmed, for example, by their competition for the epitope, although the test method is not limited thereto. The competition between antibodies can be assessed by competitive binding assays. The method includes ELISA, fluorescence resonance energy transfer (FRET), and fluorometric microvolume assay technology (FMAT™). The amount of a particular antibody bound to antigen is indirectly correlated with the binding activity of a competitor antibody candidate (test antibody), which competes for the binding to the same epitope. Specifically, as the amount or affinity of a test antibody for the same epitope increases, the amount of an antibody bound to the antigen decreases, and the amount of test antibody bound to the antigen increases. More specifically, an appropriately labeled antibody is added to the antigen together with a test antibody, and then the bound antibody is detected using the label. The amount of an antibody bound to the antigen can be readily determined by labeling the antibody in advance. Such labels are not particularly limited; however, appropriate labeling methods are selected depending on the technique. Such labeling methods include, for example, fluorescent labeling, radiolabeling, and enzyme labeling.

Herein, "antibody that recognizes the same epitope" refers to an antibody that can reduce the amount of labeled antibody bound by at least 50%, when a test antibody is used at a concentration typically 100 times higher, preferably 80 times higher, more preferably 50 times higher, even preferably 30 times higher, and still preferably 10 times higher than the $IC_{50}$ of the non-labeled antibody, where $IC_{50}$ is defined as a concentration of a non-labeled antibody at which the amount of the labeled antibody bound is decreased by 50% due to the binding of the non-labeled antibody.

The antibodies of the present invention include both polyclonal and monoclonal antibodies. Methods for preparing and purifying monoclonal and polyclonal antibodies are known in the field, and described, for example, in "Harlow and Lane, Antibodies: A Laboratory Manual (New York: Cold Spring Harbor Laboratory Press, 1988)".

The antibodies of the present invention also include recombinant antibodies such as humanized antibodies and chimeric antibodies. "Humanized antibody" refers to an antibody whose structure is similar to that of a human antibody. Such humanized antibodies and chimeric antibodies include human-type chimeric antibodies (for example, antibodies in which some portions have been humanized, antibodies whose CH2 region has been humanized, antibodies whose Fc domain has been humanized, antibodies whose constant region has been humanized), CDR-grafted humanized antibodies whose constant and variable regions have been humanized except their complementarity determining regions (CDRs) (P. T. Johons et al., Nature 321, 522 (1986)), and completely humanized antibodies. Improvement methods for enhancing the antigen binding activity of a CDR-grafted human-type antibody have been developed, which include: methods for selecting human antibody FRs that are highly homologous to the mouse antibody, methods for producing highly homologous humanized antibodies, and methods for substituting amino acids in FR after grafting mouse CDRs to human antibodies (see U.S. Pat. Nos. 5,585,089, 5,693,761, 5,693,762, and 6,180,370; EP Nos. 451216 and 682040; Japanese Patent No. 2828340). Such methods can be used to prepare CDR-grafted human-type antibodies of the present invention.

Human-type chimeric antibodies can be produced, for example, by substituting a human anybody constant region for the constant region of an above-described antibody having the structure of an H-chain variable region and/or the structure of an L-chain variable region described above. Such human antibody constant regions include known human antibody constant regions. A method for producing human-type chimeric antibodies is described below as an example.

First, mRNA is extracted from hybridomas producing a mouse antibody against a particular target antigen. cDNA is synthesized from the mRNA by a conventional method. The synthesized cDNA is inserted into a vector to construct a cDNA library. A vector carrying H-chain and L-chain genes is selected from the cDNA library using H-chain gene and L-chain gene fragments as a probe. The sequences of the H-chain variable region and L-chain variable region genes are determined by sequencing the insert in the selected vector. DNA encoding the H-chain variable region is constructed based on the sequence data obtained as described above by chemical synthesis, biochemical cleavage/ligation, or the like. The resulting DNA that encodes the H-chain variable region is ligated with a DNA encoding human H-chain constant region, and then inserted into an expression vector to construct an expression vector for H chain. Such expression vectors include, for example, SV40 virus-based vectors, EB virus-based vectors, and papilloma virus (BPV)-based vectors, but are not limited thereto. Furthermore, expression vectors for L chain are constructed by the same method. Host cells are co-transformed with the H-chain expression vectors and L-chain expression vectors. Preferred host cells include CHO cells (Chinese hamster ovary) (A. Wright & S. L. Morrison, J. Immunol. 160, 3393-3402 (1998)) and SP2/0 cells (mouse myeloma) (K. Motmans et al., Eur. J. Cancer Prev. 5, 512-519 (1996); R. P. Junghans et al., Cancer Res. 50, 1495-1502 (1990)). Transformation can be preferably carried out by using electroporation, a lipofectin method (R. W. Malone et al., Proc. Natl. Acad. Sci. USA 86, 6077 (1989); P. L. Felgner et al., Proc. Natl. Acad. Sci. USA 84, 7413 (1987)), calcium phosphate method (F. L. Graham & A. J. van der Eb, Virology 52, 456-467 (1973)), DEAE-Dextran method, and the like.

The transformants are cultured, and then human-type chimeric antibodies are isolated from the transformants or culture media. Antibodies can be isolated or purified by an appropriate combination of methods such as centrifugation, ammonium sulfate fractionation, salting out, ultrafiltration, affinity chromatography, ion exchange chromatography, and gel filtration chromatography.

Meanwhile, human-type CDR-grafted antibodies can be produced, for example, by the following method. First, the amino acid sequences of H-chain and L-chain variable regions of an antibody against a particular antigen, and nucleotide sequences encoding them are determined by the methods for producing chimeric antibodies as described above. The amino acid and nucleotide sequences of each CDR are determined as well.

Next, framework regions (FRs) which sandwich CDRs are selected. Three methods are available for selecting FRs. The first method uses human antibody frames with known three dimensional structures, such as NEWM and REI (Riechmann L. et al., Nature 332, 323-3Z7 (1988); Tempst, P R. et al., Protein Engineering 7, 1501-1507 (1994); Ellis J H. et al., J. Immunol 155, 925-937 (1995)). The second method uses FRs of a human antibody variable region that is most homologous to a mouse antibody variable region of interest, in which the human antibody variable region is selected from databases (Queen C. et al., Proc Natl Acad Sci USA 86, 10029-10033 (1989); Rozak M J. et al., J Biol Chem 271, 22611-22618 (1996); Shearman C W. et al., J. Immunol. 147, 4366-4373 (1991)). In the third method, amino acids most commonly shared by human antibody FRs are selected (Sato K. et al., Mol Immunol 31, 371-381 (1994); Kobinger F. et al., Protein Engineering 6, 971-980 (1993); Kettleborough C A. et al., Protein Engineering 4, 773-783 (1991)). All of these methods can be used in the present invention.

Furthermore, FR amino acid sequences to be used also include amino acid sequences resulting from modification of the amino acid sequence of a selected human FR, as long as the human-type CDR-grafted antibody produced from it has the activity of specifically binding to the target antigen. In particular, when a portion of the amino acid sequence of a selected human FR is replaced with the amino acid sequence of an FR of the antibody from which CDR is derived, the resulting antibody is very likely to retain the antibody properties. The number of amino acids to be modified is preferably 30% or less in a whole FR, more preferably 20% or less in a whole FR, and still more preferably 10% or less in a whole FR.

Next, DNAs encoding H-chain and L-chain variable regions are designed by combining the above-described CDRs with FRs selected by any one of the methods described above. Based on this design, DNAs encoding H-chain variable regions and DNAs encoding L-chain variable regions are prepared by chemical synthesis, biochemical cleavage/ligation, or the like. Then, an H-chain expression vector is constructed by inserting into an expression vector the H-chain variable region-encoding DNA, along with a DNA encoding an H-chain constant region of human immunoglobulin. Likewise, an L-chain expression vector is constructed by inserting into an expression vector the L-chain variable region-encoding DNA, along with a DNA encoding an L-chain constant region of human immunoglobulin. Expression vectors include, for example, SV40 virus-based vectors, EB virus-based vectors, and papilloma virus (BPV)-based vectors, but are not limited thereto.

Host cells are co-transformed with the H-chain expression vectors and L-chain expression vectors prepared by the method described above. Such preferred host cells include CHO cells (Chinese hamster ovary) (A. Wright & S. L. Morrison, J. Immunol. 160, 3393-3402 (1998)) and SP2/0 cells (mouse myeloma) (K. Motmans et al., Eur. J. Cancer Prev. 5, 512-519 (1996); R. P. Junghans et al., Cancer Res. 50, 1495-1502 (1990)). Transformation can be preferably carried out by using electroporation, a lipofectin method (R. W. Malone et al., Proc. Natl. Acad. Sci. USA 86, 6077 (1989); P. L. Felgner et al., Proc. Natl. Acad. Sci. USA 84, 7413 (1987)), calcium phosphate method (F. L. Graham & A. J. van der Eb, Virology 52, 456-467 (1973)), DEAE-Dextran method, and the like.

The transformants are cultured, and then human-type CDR-grafted antibodies are isolated from the transformants or culture media. Antibodies can be isolated or purified by an appropriate combination of methods such as centrifugation, ammonium sulfate fractionation, salting out, ultrafiltration, affinity chromatography, ion exchange chromatography, and gel filtration chromatography.

Methods for preparing human antibodies are also known. For example, desired human antibodies with antigen-binding activity can be obtained by sensitizing human lymphocytes in vitro with an antigen of interest or cells expressing an antigen of interest; and fusing the sensitized lymphocytes with human myeloma cells such as U266 (see Japanese Patent Application Kokoku Publication No. (JP-B) H01-59878 (examined, approved Japanese patent application published for opposition)). Alternatively, desired human antibodies can also be obtained by using an antigen of interest to immunize transgenic animals that have the entire repertoire of human antibody genes (see International Patent Application WO 93/12227, WO 92/03918, WO 94/02602, WO 94/25585, WO 96/34096, and WO 96/33735).

In an alternative embodiment, antibodies and antibody fragments can be isolated from an antibody phage library produced by using the technique described by McCafferty et al. (Nature, 348: 552-554 (1990)). Clackson et al. (Nature, 352: 624-628 (1991)) and Marks et al. (J. Mol. Biol., 222: 581-597 (1991)) reported isolation of mouse and human antibodies using phage libraries. Subsequently published documents describe generation of high-affinity (nM range) human antibodies by chain shuffling (Marks et al., Bio/Technology, 10: 779-783 (1992)); and combinatorial infection and in vivo recombination as a strategy for constructing very large phage libraries (Waterhouse et al., Nuc. Acids. Res., 21: 2265-2266 (1993)). These techniques can serve as an alternative method for isolating monoclonal antibodies, which are used instead of the conventional hybridoma method for preparing monoclonal antibodies.

In this context, the bacteriophage (phage) display is one of the well-known techniques that enable one to search a large oligopeptide library and identify library members having the ability to specifically bind to a target polypeptide. The phage display is a technique that displays various polypeptides as a fusion protein with the coat protein on the surface of bacteriophage particles (Scott, J. K. and Smith G P. Science 249: 386 (1990)). An advantage of phage display is that it enables rapid and effective categorization of a large library of selectively randomized protein mutants (or random cDNA clones) for the sequences that bind with high affinity to a target molecule. The phage display of peptide library (Cwirla, S. E. et al., Proc. Natl. Acad. Sci. USA, 87: 6378 (1990)) or protein library (Lowman, H. B. et al., Biochemistry, 30: 10832 (1991); Clackson, T. et al., Nature, 352:624 (1991); Marks, J. D. et al., J. Mol. Biol., 222: 581 (1991); Kang, A. S. et al., Proc. Natl. Acad. Sci. USA, 88:8363 (1991)) has been used to screen a vast number of oligopeptides or polypeptides for those that have a specific binding property (Smith, G P. Current Opin. Biotechnol., 2:668 (1991)). Categorization in a phage library of random mutants requires a method for constructing and propagating a vast number of mutants; an affinity purification method using a target receptor; and a method for assessing the enhanced binding (see U.S. Pat. Nos. 5,223, 409, 5,403,484, 5,571,689, and 5663143).

Most phage display methods use filamentous phages; however, known phage display methods also include λ phage display system (WO 95/34683; U.S. Pat. No. 5,627,024), T4 phage display system (Ren J. et al., Gene 215: 439 (1998); Zhu et al., Cancer Research, 58 (15):3209-3214 (1998); Jiang et al., Infection & Immunity, 65(11): 4770-4777 (1997); Ren et al., Gene, 195(2): 303-311 (1997); Ren, Protein Sci. 5: 1833 (1996); Efimov et al., Virus Genes 10: 173 (1995)) and T7 phage display system (Smith and Scott, Methods in Enzymology, 217, 228-257 (1993); U.S. Pat. No. 5,766,905).

To date, there are many improved and modified methods developed based on the basic phage display method. These modifications have improved the methods for screening peptide or protein libraries based on a property or ability such as the activity of binding to a selected target molecule. Recombination means for the phage display method are described in WO 98/14277. Phage display libraries have been used to analyze and control bimolecular interactions (WO 98/20169; WO 98/20159) and properties of constrained helical peptide (WO 98/20036). WO 97/35196 describes a method for isolating affinity ligands, in which bound ligands are selectively isolated by contacting a phage display library with a first solution that allows binding of the ligand to a target molecule and then with a second solution where affinity ligand does not bind to the target molecule. WO 97/46251 describes a method for isolating high affinity-binding phages in which a random phage display library is treated by biopanning using an affinity-purified antibody, followed by isolation of bound phages, and then by micropanning in the wells of microplates. There is also a report published on the use of *Staphylococcus aureus* protein A as an affinity tag (Li et al., Mol. Biotech., 9: 187 (1998)). WO 97/47314 describes the use of substrate subtraction library in identifying enzymatic specificity using a combinatorial library which may be a phage display library. WO 97/09446 describes a method for selecting enzymes that are suitable as a washing reagent to be used in phage display. Other methods for selecting proteins that bind in a specific manner are described in U.S. Pat. Nos. 5,498,538 and 5,432, 018, and WO 98/15833. Methods for constructing and screening peptide libraries are described in U.S. Pat. Nos. 5,723, 286, 5,432,018, 5,580,717, 5,427,908, 5,498,530, 5,770,434, 5,734,018, 5,698,426, 5,763,192, and 5,723,323.

Furthermore, there are known techniques for obtaining human antibodies by panning with a human antibody library. For example, using a phage display method, the variable regions of human antibodies can be expressed as single chain antibodies (scFvs) on the surface of phages to select phages that bind to an antigen. The DNA sequences encoding the variable regions of human antibodies that bind to the antigen can be determined by analyzing the genes of selected phages. When the DNA sequences of scFvs that bind to the antigen are identified, human antibodies can be prepared by constructing appropriate expression vectors carrying these sequences and expressing the antibodies in adequate hosts introduced with the expression vectors. Such methods are already known (see WO 92/01047, WO 92/20791, WO 93/06213, WO 93/11236, WO 93/19172, WO 95/01438, and WO 95/15388).

As an alternative method, the phage display technique (McCafferty et al., Nature 348: 552-553 (1990)) can be used to produce human antibodies and antibody fragments in vitro from the immunoglobulin variable (V) domain gene repertoire of a non-immunized donor. Using this technique, an antibody V domain gene is cloned in frame with a coat protein gene of filamentous bacteriophage, for example, M13 or fd, and then displayed as a functional antibody fragment on the surface of phage particles. Since filamentous particles contain a single-stranded DNA copy of the phage genome, screening based on the functional properties of antibody results in selection of genes encoding an antibody having the properties. Thus, such phages mimic some characteristics of B cells. Phage display can be carried out in various modes; see, for example, Johnson, Kevin S, and Chiswell, David J., Current Opinion in Structural Biology 3: 564-571 (1993). There are some sources of V gene segments available for phage display. Clackson et al. (Nature, 352: 624-628 (1991)) have isolated numerous various anti-oxazolone antibodies from a small random combinatorial library of V genes derived from spleens of immunized mice. The V gene repertoire of a non-immunized human donor can be constructed, and antibodies against numerous various antigens (including self antigens) can be isolated by using the technique described in either of the following documents without modification: Marks et al., J. Mol. Biol. 222: 581-597 (1991) or Griffith et al., EMBO J. 12: 725-734 (1993). See also U.S. Pat. Nos. 5,565,332 and 5,573,905.

The antibodies of the present invention also include functional antibody fragments such as Fab, Fab', $F(ab')_2$, Fv, scFv, dsFv, Diabodies, and $sc(Fv)_2$. Multimers (for example, dimers, trimers, tetramers, and polymers) of such a functional antibody fragment are also included in the antibodies of the present invention.

Fab is a fragment with a molecular weight of about 50,000 that consists of L-chain and H-chain variable regions, and an H chain fragment containing $C_H1$ domain and a portion of hinge region. Fab is obtained by digesting IgG with papain in the presence of cysteine. In the present invention, an antibody described above can be digested with papain to prepare such Fab. Alternatively, a DNA encoding a portion of H chain and the L chain of an antibody described above is inserted into an appropriate vector. Fab can be prepared from transformants obtained by transformation using the vector.

Fab' is a fragment with a molecular weight of about 50,000 obtained by cleaving the disulfide bond between the H chains of $F(ab')_2$ described below. In the present invention, such $F(ab')_2$ can be obtained by treating an above-described antibody by pepsin digestion, followed by cleavage of disulfide bond with a reducing agent. Alternatively, like Fab, Fab' can be prepared by genetic engineering using DNA encoding Fab'.

$F(ab')_2$ is a fragment with a molecular weight of about 100,000 obtained by digesting IgG with pepsin. $F(ab')_2$ is constituted by two (Fab') fragments linked together via disulfide bond, each of which consists of L-chain and H-chain variable regions, and an H chain fragment containing $C_H1$ domain and a portion of hinge region. In the present invention, $F(ab')_2$ can be prepared by digesting an above-described antibody with pepsin. Alternatively, like Fab, $F(ab')_2$ can be prepared by genetic engineering using $F(ab')_2$-encoding DNAs.

Fv can be prepared by digesting an antibody into antibody fragments with an enzyme, for example, papain or pepsin. Alternatively, genes encoding antibody fragments are constructed and inserted into an expression vector. Fv can be expressed in appropriate host cells using the vector (see, for example, Co, M. S. et al., J. Immunol. 152, 2968-2976 (1994); Better, M. and Horwitz, A. H. Methods in Enzymology 178, 476-496 (1989); Plueckthun, A. and Skerra, A. Methods in Enzymology 178, 476-496 (1989); Lamoyi, E., Methods in Enzymology 121, 652-663 (1989); Rousseaux, J. et al., Methods in Enzymology 121, 663-669 (1989); Bird, R. E. et al., TIBTECH 9, 132-137 (1991)).

scFv is a single-chain antibody fragment in which the C terminus of one Fv chain consisting of H-chain and L-chain variable regions is linked via an appropriate peptide linker to the N terminus of the other Fv chain. Such peptide linkers include, for example, flexible $(GGGGS)_3$. For example, a DNA encoding an scFv antibody is constructed using DNAs encoding the H-chain variable region and L-chain variable region of an above-described antibody and a DNA encoding a peptide linker, and then inserted into an appropriate vector. Transformants are obtained by transformation with the resulting vector. scFv can be prepared from the transformants.

dsFv is an Fv fragment whose H-chain and L-chain variable regions are stabilized with a disulfide bond formed by introducing Cys residues at appropriate positions in the H-chain and L-chain variable regions. In each chain, the position at which Cys residue is to be introduced is determined based on the conformation predicted by molecular modeling. In the present invention, for example, the conformation is predicted from the amino acid sequences of H-chain and L-chain variable regions of an above-described antibody. DNAs are constructed to encode H-chain and L-chain variable regions that have been introduced with mutations based on the prediction, and inserted into an appropriate vector. Transformants are obtained by transformation with the resulting vector. dsFv can be prepared from the transformants.

Furthermore, multimers of antibody fragments can be prepared by linking scFv antibodies, dsFv antibodies, and the like via appropriate linkers, or fusing them to streptavidin. Fusion antibodies or labeled antibodies can be prepared from the antibodies (including antibody fragments) of the present invention by fusing or linking the antibodies with low molecular weight compounds, proteins, labeling substance, or the like. Such labeling substances include radioactive substances such as $^{125}I$.

Diabody refers to a bivalent antibody fragment constructed by gene fusion (Holliger P et al., Proc. Natl. Acad. Sci. USA, 90: 6444-6448 (1993); EP 404,097; WO 93/11161). Diabodies are dimers consisting of two polypeptide chains, where each polypeptide chain has a VL and a VH linked via a linker short enough to prevent interaction of these two domains, for example, a linker of about five residues. The VL and VH linked together in a single polypeptide chain will form a dimer because the linker between them is too short to form a single-chain variable region fragment. As a result, the polypeptide chains form a dimer, and thus the diabody has two antigen binding sites. Diabodies can be prepared by treating an antibody with an enzyme, for example, papain or pepsin, to generate antibody fragments, or by constructing DNAs encoding those antibody fragments and introducing them into expression vectors, followed by expression in an appropriate host cell (see, for example, Co, M. S. et al., J. Immunol. 152, 2968-2976 (1994); Better, M. and Horwitz, A. H., Methods Enzymol. 178, 476-496 (1989); Pluckthun, A. and Skerra, A., Methods Enzymol. 178, 497-515 (1989); Lamoyi, E., Methods Enzymol. 121, 652-663 (1986); Rousseaux, J. et al., Methods Enzymol. 121, 663-669 (1986); Bird, R. E. and Walker, B. W., Trends Biotechnol. 9, 132-137 (1991)).

sc(Fv)2 is a single-chain minibody produced by linking two VHs and two VLs using linkers and such (Hudson et al., J. Immunol. Methods 231: 177-189 (1999)). sc(Fv)2 can be produced, for example, by linking scFvs via a linker.

The antibodies of the present invention also include fusion proteins in which an above-described antibody is fused with other peptides or proteins. The fusion protein can be prepared by linking a polynucleotide encoding an antibody of the present invention with a polynucleotide encoding a different peptide or polypeptide in frame, and introducing this into an expression vector and expressing it in a host. It is possible to use techniques known to those skilled in the art. Such a peptide or polypeptide to be fused with an antibody of the present invention include known peptides, for example, such as FLAG (Hopp, T. P. et al., BioTechnology 6, 1204-1210 (1988)), 6× His consisting of six His (histidine) residues, 10× His, influenza hemagglutinin (HA), human c-myc fragment, VSV-GP fragment, p18HIV fragment, T7-tag, HSV-tag, E-tag, SV40 T antigen fragment, lck tag, α-tubulin fragment, B-tag, and Protein C fragment. Furthermore, polypeptides to be fused with an antibody of the present invention include, for example, GST (glutathione-5-transferase), HA (influenza hemagglutinin), β-galactosidase, and MBP (maltose-binding protein).

The antibodies of the present invention also include antibodies linked to a labeling substance.

Such labeling substances include, but are not limited to, enzymatic luminescence (luciferase), luminescent low-molecular-weight substances, fluorescent proteins, fluorescent low-molecular-weight substances, and radionuclides. Such radionuclides include, but are not limited to, γ-ray emitting nuclides such as $^{51}Cr$, $^{59}Fe$, $^{57}Co$, $^{67}Ga$, $^{75}Se$, $^{81m}Kr$, $^{99m}Tc$, $^{111}In$, $^{125}I$, $^{131}I$, $^{133}Xe$, and $^{201}Tl$, and positron-emitting nuclides such as $^{11}C$, $^{13}N$, $^{15}O$, $^{18}F$, $^{35m}Cl$, $^{76}Br$, $^{45}Ti$, $^{48}V$, $^{60}Cu$, $^{61}Cu$, $^{62}Cu$, $^{66}Ga$, $^{89}Zr$, $^{94m}Tc$, and $^{124}I$. "m" represents nuclear isomer, which is apparent to those skilled in the art.

Fluorescent labels and luminescent labels include those using enzymatic luminescence (luciferase) and those using fluorescence (fluorescent proteins such as GFP, DsRed, and Kusabira Orange; and fluorescent low-molecular-weight substances such as FITC, Cy5.5, and Alexa Fluor 750).

When enzymatic luminescence (luciferase) is used, it is necessary to administer a substrate separately.

In particular, labels that have reduced influence from the animal's intrinsic fluorescence, and labels that emit a signal with high skin permeability are more preferred.

The present invention also provides DNAs encoding an antibody of the present invention, vectors inserted with the DNAs, and transformed cells introduced with the vectors. The vectors include, for example, M13 vectors, pUC vectors, pBR322, pBluescript, and pCR-Script. Alternatively, when the objective is to subclone and excise cDNAs, the vectors include pGEM-T, pDIRECT, and pT7, in addition to those described. DNAs encoding an antibody of the present invention, vectors inserted with the DNAs, and transformed cells introduced with the vectors are prepared by known methods.

DNAs encoding an antibody of the present invention that has reactivity towards calcified globules and activity to bind to arteriosclerotic plaques (in particular, calcified arteriosclerotic lesions) include the following DNAs:

(a) a DNA encoding a heavy chain having the nucleotide sequence of SEQ ID NO: 5;

(b) a DNA encoding a light chain having the nucleotide sequence of SEQ ID NO: 10;

(c) a DNA encoding a heavy chain having the nucleotide sequence of SEQ ID NO: 15;

(d) a DNA encoding a light chain having the nucleotide sequence of SEQ ID NO: 20;

(e) a DNA encoding a heavy chain having the nucleotide sequence of SEQ ID NO: 25;

(f) a DNA encoding a light chain having the nucleotide sequence of SEQ ID NO: 30;

(g) a DNA encoding a heavy chain having the nucleotide sequence of SEQ ID NO: 35;
(h) a DNA encoding a light chain having the nucleotide sequence of SEQ ID NO: 40;
(i) a DNA encoding a heavy chain having the nucleotide sequence of SEQ ID NO: 45; and
(j) a DNA encoding a light chain having the nucleotide sequence of SEQ ID NO: 50.

When an expression vector is used for expression in *E. coli*, for example, it should have the above-described characteristics which allow its amplification in *E. coli*. Additionally, when the host is *E. coli* such as JM109, DH5α, HB101, or XL1-Blue, the vector must have a promoter that allows efficient expression in *E. coli*, for example, lacZ promoter (Ward et al. Nature 341: 544-546 (1989); FASEB J. 6: 2422-2427 (1992)), araB promoter (Better et al. Science 240:1041-1043 (1988)), or T7 promoter. The vector also includes pGEX-5X-1 (Pharmacia), "QIAexpress system" (QIAGEN), pEGFP, and pET (for this vector, BL21, a strain expressing T7 RNA polymerase, is preferably used as the host), in addition to the above-described vectors.

Furthermore, the vector may comprise a signal sequence for polypeptide secretion. When producing proteins into the periplasm of *E. coli*, the pelB signal sequence (Lei, S. P. et al. J. Bacteriol. 169: 4379 (1987)) may be used as a signal sequence for protein secretion. The vector can be introduced into host cell, for example, by the calcium chloride method or electroporation.

In addition to *E. coli* expression vectors, the vector includes, for example, expression vectors derived from mammals (for example, pcDNA3 (Invitrogen), pEGF-BOS (Nucleic Acids Res. 18(17): 5322 (1990)), pEF, and pCDM8), insect cells (for example, "Bac-to-BAC baculovirus expression system" (GIBCO-BRL), pBacPAK8), plants (for example, pMH1 and pMH2), animal viruses (for example, pHSV, pMV, and pAdexLcw), retroviruses (for example, pZIPneo), yeasts (for example, "*Pichia* Expression Kit" (Invitrogen), pNV11, and SP-Q01), and *Bacillus subtilis* (for example, pPL608 and pKTH50).

In order to express proteins in animal cells, such as CHO, COS, and NIH3T3 cells, the vector must have a promoter necessary for expression in such cells, for example, SV40 promoter (Mulligan et al. Nature 277:108 (1979)), MMTV-LTR promoter, EF1α promoter (Mizushima et al. Nucleic Acids Res. 18: 5322 (1990)), CMV promoter, etc). It is even more preferable that the vector carries a gene for selecting transformants (for example, a drug-resistance gene that enables discrimination by a drug (such as neomycin and G418)). Vectors having such characteristics include, for example, pMAM, pDR2, pBK-RSV, pBK-CMV, pOPRSV, and pOP13.

In addition, the following method can be used for stable gene expression and gene amplification in cells: CHO cells deficient in a nucleic acid synthesis pathway are introduced with a vector (for example, pCHOI) that carries a DHFR gene which compensates for the deficiency, and the gene is amplified using methotrexate (MTX). Alternatively, the following method can be used for transient gene expression: COS cells whose chromosome contains a gene for expression of SV40 T antigen are transformed with a vector (such pcD) having an SV40 origin of replication. It is also possible to use replication origins derived from polyoma virus, adenovirus, bovine papilloma virus (BPV), or such. To increase gene copy number in host cells, the expression vectors may further contain selection markers such as aminoglycoside transferase (APH) gene, thymidine kinase (TK) gene, *E. coli* xanthine-guanine phosphoribosyltransferase (Ecogpt) gene, and dihydrofolate reductase (dhfr) gene.

Host cells to be introduced with the vectors are not particularly limited, and include, for example, *E. coli* and various types of animal cells. The host cells can be used, for example, as production systems for expressing and producing the antibodies of the present invention. The polypeptide production systems include in vitro and in vivo production systems. The in vitro production systems include production systems using eukaryotic or prokaryotic cells.

When eukaryotic cells are used, for example, animal cells, plant cells, and fungal cells can be used as the host. Such animal cells include mammalian cells (for example, CHO (J. Exp. Med. 108, 945 (1995)), COS, 3T3, myeloma, baby hamster kidney (BHK), HeLa, and Vero), amphibian cells (for example, *Xenopus* oocyte (Valle, et al., Nature 291, 338-340 (1981))), and insect cells (for example, Sf9, Sf21, and Tn5). In the present invention, CHO-DG44, CHO-DXB11, COST cells, and BHK cells are preferably used. CHO cells are particularly preferred for large-scale expression in animal cells. The vectors can be introduced into host cells, for example, by calcium phosphate methods, DEAE-dextran methods, methods using cationic liposome DOTAP (Boehringer-Mannheim), electroporation, and lipofection.

The plant cells include, for example, *Nicotiana tabacum*-derived cells, which are known as a protein production system and can be cultured as a callus. The fungal cells include yeasts, for example, the genus *Saccharomyces* such as *Saccharomyces cerevisiae* and *Saccharomyces pombe*; and filamentous bacteria, for example, the genus *Aspergillus* such as *Aspergillus niger*.

When prokaryotic cells are used, production systems using bacterial cells are available. Such bacterial cells include *E. coli*, for example, JM109, DH5α, and HB101, and *Bacillus subtilis*. The antibodies of the present invention can be prepared in vitro by culturing cells transformed with a DNA of the present invention and purifying the antibodies by conventional methods that are routinely used by those skilled in the art.

The present invention also provides host organisms that harbor a vector carrying a nucleic acid encoding an antibody of the present invention. The host organisms of the present invention are useful in producing recombinant antibodies. The host organisms of the present invention include goats. For example, transgenic goats of the present invention can be created by the method described below. Specifically, a fusion gene is constructed by inserting an antibody gene in frame within a gene encoding a protein (goat βcasein or such) intrinsically produced in milk. DNA fragments comprising the fusion gene which contains the inserted antibody gene are injected into goat embryos, and the resulting embryos are introduced into female goats. The antibodies of the present invention can be prepared from milk produced by transgenic animals born by the goats that received the embryos, or produced from progenies of these animals. Hormones can be given to the transgenic goats to increase the amount of milk containing the antibodies of the present invention produced by the goats (Ebert, K. M. et al., Bio/Technology 12, 699-702 (1994)).

The present invention provides imaging agents for visualizing calcified arteriosclerotic lesions, which contain an antibody that has reactivity towards calcified globules and activity to bind to arteriosclerotic plaques (in particular, calcified arteriosclerotic lesions). The present invention also provides imaging methods for visualizing calcified arteriosclerotic lesions, which contain an antibody of the present invention that has reactivity towards calcified globules and activity to bind to arteriosclerotic plaques (in particular, calcified arteriosclerotic lesions). The imaging agents of the present invention are administered to mammals to visualize calcified arteriosclerotic lesions. Such mammals include humans and nonhuman mammals (for example, mice, rats, and monkeys). The imaging agents of the present invention are useful in diagnosing arteriosclerosis. The imaging agents of the present invention can be used both in vivo and in vitro.

In an imaging agent of the present invention, an imaging label or probe that enables direct or indirect monitoring is linked to an antibody of the present invention which has reactivity towards calcified globules and activity to bind to arteriosclerotic plaques (in particular, calcified arteriosclerotic lesions).

After in vivo administration (for example, intravenous administration) of an above-described probe, the distribution or amount accumulated can be assessed using an imagining device such as PET, SPECT, or CCD camera.

Furthermore, in recent years, computer-aided tomography (computed tomography; "CT" also refers to computed tomography) has been applied in a clinical setting such as for disease diagnosis. Computer-aided tomography is a technology for generating an image of the interior of an object by scanning the object using a source of penetrating radiation, and processing the data in a computer.

The CT technology is a technique for obtaining two-dimensional cross sectional patterns of objects (cross sections, etc.) by recording sectional images with positron emission tomography (PET), single photon emission computed tomography (SPECT), magnetic resonance imaging (MRI), or the like. These examination techniques are often used not only for obtaining sectional images, but also for presenting three dimensional graphic images by integrating the two-dimensional images using the advanced computer-assisted image processing technology. Thus, the examination techniques are powerful tools for specifying the three-dimensional location of lesions, diagnosis, decision of operative strategy, and so on.

For example, simple CT is used to obtain images by irradiating X ray or the like without using any contrast agent. Tissue edema, morphological abnormalities of bone, morphologies, and the like can be observed without using any contrast agent. Meanwhile, enhanced CT refers to CT in which images are taken after a contrast agent or the like having high X-ray absorption is injected into a blood vessel. Enhanced CT can be used to observe morphologies of blood vessels and tissues rich in blood flow. Furthermore, the so-called next-generation CT has been developed, and it can be used alone or in combination to detect the imaging agents of the present invention. Such next-generation CT is not particularly limited, and includes, for example, helical CT in which the irradiation source moves in a spiral manner, and multi-detector computed tomography (MDCT) (also referred to as multi-slice CT (MSCT)) in which detectors are arranged in multiple rows in the direction of body axis.

When the labeled imaging probe (an imaging agent of the present invention) is a radionuclide with high X-ray absorption, CT can be used alone as a detector.

Such labeling substances include, but are not limited to, enzymatic luminescence (luciferase), luminescent low-molecular-weight substances, fluorescent proteins, fluorescent low-molecular-weight substances, and radionuclides. Such radionuclides include, but are not limited to, γ-ray emitting nuclides such as $^{51}Cr$, $^{59}Fe$, $^{57}Co$, $^{67}Ga$, $^{75}Se$, $^{81m}Kr$, $^{99m}Tc$, $^{111}In$, $^{125}I$, $^{131}I$, $^{133}Xe$, and $^{201}Tl$, and positron-emitting nuclides such as $^{11}C$, $^{13}N$, $^{15}O$, $^{18}F$, $^{35m}Cl$, $^{76}Br$, $^{45}Ti$, $^{48}V$, $^{60}Cu$, $^{61}Cu$, $^{62}Cu$, $^{66}Ga$, $^{89}Zr$, $^{94m}Tc$, and $^{124}I$. "m" represents nuclear isomer, which is apparent to those skilled in the art. In particular, indium-111, technetium-99m, and iodine-131 can be particularly preferably used in two-dimensional scanning or single photon emission computed tomography (SPECT). Positron-emitting nuclide labels, for example, fluoride-19 can be particularly preferably used in positron emission tomography. Paramagnetic ions, for example, gadolinium (III) and manganese (II) can be particularly preferably used in magnetic resonance imaging (MRI).

Such labeling substances include fluorescent labels, those using enzymatic luminescence (luciferase), and those using fluorescence (fluorescent proteins such as GFP, DsRed, and Kusabira Orange; and fluorescent low-molecular-weight substances such as, FITC, Cy5.5, and Alexa Fluor 750).

When enzymatic luminescence (luciferase) is used, it is necessary to administer a substrate separately.

In particular, labels that have reduced influence from the animal's intrinsic fluorescence are preferred, and labels that emit a signal with high skin permeability are more preferred.

Magnetic resonance imaging (MRI), PET, and SPECT are used as an imaging detector. In particular, when fluorescent probes are used, CCD camera is preferably used as the monitoring device in terms of low invasiveness.

For this reason, labels that emit light at a wavelength detectable by CCD camera, for example, about 350 to 900 nm, are preferred. Furthermore, devices that can be used to determine the intensity of light source inside the body based on values obtained by monitoring the body surface of a test animal with a CCD camera are preferred. When fluorescent labels are used, the image may be a reflection fluorescence image or transmission fluorescence image; however, it is preferable to capture both images. Furthermore, the fluorescence images can be observed three-dimensionally by superimposing multi-directionally recorded fluorescence images (regardless of reflection or transmission) and integrating information of the radiation source into the superimposed images. This processing is preferred because it enables reproduction of accurate three-dimensional locations and distribution. The three-dimensional images obtained by this method can also be further superimposed with CT images. With the superimposed three-dimensional CT data, the location of a label can be monitored multi-directionally as an animation in a virtual three-dimensional space.

When the labeled imaging probe is linked to a radionuclide with high X-ray absorption, CT can be used alone as the imaging detector (for example, PET or SPECT) as described above, and can also be used to determine the site, accumulated amount, and distribution of arteriosclerotic plaques.

Alternatively, following in vivo administration (for example, intravenous administration) of the above described labeled imaging probe, the labeled probe may be observed by CT alone or in combination with CCD. When CT is used in combination with CCD, for example, a CCD image of fluorescently labeled probe is superimposed with an image of simple CT (and/or an image of enhanced CT). Specifically, CT images resulting from simple-CT image extraction of organs such as bones and lungs (and/or enhanced-CT image extraction of blood vessels and tissues) are integrated with fluorescent probe images of major arterial lesions such as in the heart. This enables more accurate understanding of the site, accumulated amount, and distribution of arteriosclerotic plaques, three-dimensional positional relationships relative to tissues and blood vessels, and accurate three-dimensional images (localization) of arteriosclerotic plaques.

The imaging agents of the present invention can be formulated, in addition to the antibodies, with pharmaceutically acceptable carriers by known methods. For example, the agents can be used parenterally, when the antibodies are formulated in a sterile solution or suspension for injection using water or any other pharmaceutically acceptable liquid. For example, the agents can be formulated by appropriately combining the antibodies of the present invention with pharmaceutically acceptable carriers or media, specifically, sterile water or physiological saline, vegetable oils, emulsifiers, suspending agents, surfactants, stabilizers, flavoring agents, excipients, vehicles, preservatives, binding agents, and such, by mixing them at a unit dose and form required by generally accepted pharmaceutical practices. The content of active ingredient in such a formulation is adjusted so as to contain an appropriate dose within the specified range.

Sterile compositions for injection can be formulated using vehicles such as distilled water for injection, according to standard formulation protocols.

Aqueous solutions to be used for injection include, for example, physiological saline and isotonic solutions containing glucose or other adjuvants such as D-sorbitol, D-mannose, D-mannitol, and sodium chloride. They may be used in combination with suitable solubilizers such as alcohol, specifically ethanol, polyalcohols such as propylene glycol and polyethylene glycol, and non-ionic surfactants such as Polysorbate 80™ and HCO-50.

Oils include sesame oils and soybean oils, and can be combined with solubilizers such as benzyl benzoate or benzyl alcohol. They may also be formulated with buffers, for example, phosphate buffer or sodium acetate buffer; analgesics, for example, procaine hydrochloride; stabilizers, for example, benzyl alcohol or phenol; or antioxidants. The prepared injections are typically aliquoted into appropriate ampules.

The administration is preferably parenteral, and specifically includes injection, intranasal administration, intrapulmonary administration, and percutaneous administration. For example, injections can be administered systemically or locally by intravenous injection, intramuscular injection, intraperitoneal injection, or subcutaneous injection.

Furthermore, the method of administration can be appropriately selected depending on the patient's age and symptoms. The dosage of the imaging agents of the present invention can be selected, for example, from the range of 0.0001 to 1,000 mg per kg of body weight for each administration. Alternatively, the dosage may be, for example, in the range of 0.001 to 100,000 mg/person. However, the dosage is not limited to these values. The dose and method of administration vary depending on the subject's body weight, age, and symptoms, and can be appropriately selected by those skilled in the art.

The present invention also provides imaging kits for visualizing calcified arteriosclerotic lesions, which contain an antibody of the present invention which has reactivity towards calcified globules and activity to bind to arteriosclerotic plaques (in particular, calcified arteriosclerotic lesions). The kits of the present invention visualize calcified arteriosclerotic plaques when administered to subjects. The kits contain in addition to an antibody of the present invention, for example, injectors (apparatuses for drip infusion), adjuvants for suppressing non-specific adsorption (for example, albumin), and so on, without limitation thereto.

The kits may also contain items generally contained in kits, such as instruction manuals, appropriate containers, and control reagents used in imaging.

The present invention also provides methods for producing antibodies that have reactivity towards calcified globules and activity to bind to arteriosclerotic plaques (in particular, calcified arteriosclerotic lesions). More specifically, the present invention provides methods for producing antibodies that have reactivity towards calcified globules and activity to bind to arteriosclerotic plaques (in particular, calcified arteriosclerotic lesions), which comprise the steps of:

(a) immunizing a nonhuman animal with calcified globules or arteriosclerotic plaques; and (b) isolating antibodies from the nonhuman animal.

The methods may further comprise, after the step of (b), the step of:

(c) selecting and isolating antibodies that specifically bind to calcified globules by screening with calcified globules (NLO).

Alternatively, the methods may further comprise, after the step of (c), the steps of: (d) continuing culture after adding the antibody to a culture medium of calcified globule; and (e) selecting and isolating an antibody that inhibits the growth of calcified globule as compared to that of a control.

Each step is performed using known techniques or techniques described above.

When calcified globules (NLO) are used as immunogen, the animal species is not particularly limited as long as the calcified globules (NLO) are derived from renal/urinary calculi; however, the preferred animal species includes human. When a homogenate of arteriosclerotic plaques is used as immunogen, the site and animal species are not particularly limited, and it is possible to use human abdominal aorta or the like. Regardless of the immunogen used, antibody clones are preferably selected using the reactivity to calcified globules (NLO) as an indicator.

Furthermore, the antibodies of the present invention can be used to inhibit the progression of calcification. Thus, the present invention provides agents for inhibiting calcification progression, which comprise the antibodies of the present invention and antibodies produced by the above-described antibody-producing methods. Particularly preferred agents of the present invention for inhibiting calcification progression are agents for inhibiting the growth of calcified globules, which comprise an antibody that comprises the heavy chain of either: an antibody comprising a heavy chain that comprises CDR1 having the amino acid sequence of SEQ ID NO: 21, CDR2 having the amino acid sequence of SEQ ID NO: 22, and CDR3 having the amino acid sequence of SEQ ID NO: 23, or an antibody comprising a heavy chain that comprises a heavy-chain variable region having the amino acid sequence of SEQ ID NO: 24; and the light chain of either: an antibody comprising a light chain that comprises CDR1 having the amino acid sequence of SEQ ID NO: 26, CDR2 having the amino acid sequence of SEQ ID NO: 27, and CDR3 having the amino acid sequence of SEQ ID NO: 28 or an antibody comprising a light chain which comprises a light-chain variable region having the amino acid sequence of SEQ ID NO: 29.

Antibodies that inhibit the growth of calcified globules can be prepared as follows.

As described above, antibodies reactive to calcified globules are selected from animals immunized with calcified globules. Then, the antibodies are added to the culture medium of calcified globules. After further culturing, the growth of calcified globules is assessed, and then antibodies that inhibit the growth of calcified globules more strongly than the control (the same experiment without addition of antibody, the same experiment with addition of an antibody that does not bind to calcified globules, or an experiment in which a control antibody that binds to calcified globules but has been confirmed to produce no growth inhibitory effect is added) are selected and isolated.

The growth of calcified globules is reflected by an increase in the turbidity of culture medium, an increase in the particle size of lamellar structure observed by phase contrast microscopy, and/or an increase in the number of lamellar structures. Thus, antibodies that inhibit the growth can be assessed and selected using as an indicator whether the turbidity and/or the size of lamellar structure increases more slowly than a control, and/or the number of lamellar structures is smaller than a control, in which the control is the same experiment without addition of antibody, the same experiment with addition of an antibody that does not bind to calcified globules, or an experiment in which a control antibody that binds to calcified globules but has been confirmed to produce no growth inhibitory effect is added. Various pathological conditions are known to be accompanied by calcification progression. Thus, the antibodies of the present invention can be used effectively to inhibit their growth.

Furthermore, the present invention provides therapeutic agents for arteriosclerosis, which comprise the antibodies of the present invention and antibodies produced by the antibody-producing methods described above. For example, the progression of the disease state of a kidney disease (urinary calculi), arteriosclerosis (calcified lesions), or such can be retarded or halted by the action of an antibody of the present invention at the origin of growth of calcification.

Methods for administrating the agents, and dosage forms of the agents, and the like are described above.

The present invention further provides methods of screening for candidate compounds as therapeutic agent for arteriosclerosis, which comprise the steps of:

(a) administering an antibody of the present invention that has reactivity towards calcified globules (NLO) and activity to bind to arteriosclerotic plaques (in particular, calcified arteriosclerotic lesions), and a candidate compound to a nonhuman animal model of arteriosclerosis, for example, administering a candidate compound to a nonhuman animal model of arteriosclerosis administered with an antibody of the present invention that has reactivity towards calcified globules (NLO) and activity to bind to arteriosclerotic plaques (in particular, calcified arteriosclerotic lesions);

(b) visualizing arteriosclerotic plaques in a nonhuman animal model of arteriosclerosis administered with the antibody and candidate compound, and in a nonhuman animal model of arteriosclerosis administered with the antibody but not with the candidate compound;

(c) comparing arteriosclerotic plaques (for example, the size or site of arteriosclerotic plaques) between a nonhuman animal model of arteriosclerosis administered with the antibody and candidate compound and a nonhuman animal model of arteriosclerosis administered with the antibody but not with the candidate compound; and (d) selecting a candidate compound that reduces or eliminates arteriosclerotic plaques in a nonhuman animal model of arteriosclerosis administered with the antibody and candidate compound as compared to a nonhuman animal model of arteriosclerosis administered with the antibody but not with the candidate compound.

Each step is performed using known techniques or techniques described above.

Candidate compounds that can be used in the screening methods of the present invention include, but are not limited to, purified proteins (including antibodies), expression products of gene libraries, synthetic peptide libraries, DNA and RNA libraries (including functional nucleic acids such as aptamers and siRNAs), cell extracts, cell culture supernatants, and synthetic low-molecular-weight compound libraries.

Nonhuman animal models of disease that can be used in the screening methods of the present invention include, but are not limited to, mice, hamsters, rats, rabbits, pigs, and monkeys.

Arteriosclerosis model mice include, for example, transgenic mice in which a gene is overexpressed, and knockout mice that are deficient in a gene as a result of gene targeting. Arteriosclerosis models include, for example, apoE-deficient (apoE$^{-/-}$) model (apoE (apolipoprotein E) is a protein that forms LDL which is known as bad cholesterol), LDL receptor-deficient (LDLR$^{-/-}$) model, model introduced with human apoB, and model introduced with dominant apoE mutation. Such model mice also include type 2 diabetes model mice (KKAy), and arteriosclerosis model mice which are produced by feeding C57BL6 mice with a high cholesterol diet or such. The C57BL6 line is known to have the greatest tendency of developing arteriosclerosis among mice, and mice of this line sometimes show arteriosclerotic plaques by simply feeding on a high cholesterol diet.

Arteriosclerotic plaques are sometimes seen in rabbits fed a high cholesterol diet for about 2.5 months. Furthermore, LDL receptor-deficient arteriosclerosis model rabbits include WHHL rabbits.

A pig arteriosclerosis model is also known, which has a tendency to develop arteriosclerosis due to abnormality in the amino acid sequence of the LDL receptor-binding domain of apoB. Those skilled in the art can prepare arteriosclerosis model animals by referring to documents such as "Kessensho/Doumyakukoka Model Doubutu Sakuseihou (Methods for producing thrombosis/arteriosclerosis model animals), Ed., Koji Suzuki (Kinpodo)". The resulting model animals can be used in the present invention.

Compounds that reduce or eliminate arteriosclerotic plaques, which are selected by the screening methods of the present invention, are candidate compounds of therapeutic agents for arteriosclerosis. Thus, the present invention provides therapeutic agents for arteriosclerosis, which comprise as an active ingredient a substance selected by the screening methods of the present invention. The present invention also relates to the use of compounds selected by the screening methods of the present invention in manufacturing therapeutic agents for arteriosclerosis. When substances isolated by the screening methods of the present invention are used as a therapeutic agent, they can be used after they are formulated using known pharmaceutical production methods. For example, such substances are administered to patients in combination with pharmaceutically acceptable carriers or media (physiological saline, vegetable oils, emulsifiers, detergents, stabilizers, etc.). The substance is administered transdermally, nasally, transbronchially, intramuscularly, intravenously, or orally according to its properties. The dosage depends on the patient's age, weight, and symptoms, and the method of administration. However, those skilled in the art can select an appropriate dose.

The present invention relates to immunological methods that comprise the steps of:

(a) contacting an isolated arteriosclerotic plaque with an antibody that has reactivity towards calcified globules (NLO) and activity to bind to arteriosclerotic plaques (in particular, calcified arteriosclerotic lesions); and (b) detecting a calcification site and an arteriosclerosis site in the arteriosclerotic plaque.

Such immunological methods include, for example, immunohistochemical staining, ELISA, radioimmunoassay, FACS, immunoprecipitation, and immunoblotting. Of these immunological methods, for example, immunohistochemical staining is generally carried out according to the procedure described below in (1) to (9) to detect calcification sites and arteriosclerosis sites in arteriosclerotic plaques.

The present invention relates to kits for immunologically detecting calcification sites and arteriosclerosis sites in arteriosclerotic plaques, which contain an antibody of the present invention and an antibody that binds to the complex of oxidatively modified LDL (oxidized LDL) and $\beta_2$-glycoprotein I (oxidized LDL/$\beta_2$GPI complex). Specifically, to produce such a kit, an antibody of the present invention can be combined with substrates required for label detection, positive and negative controls, buffers used for diluting or washing samples, and so on.

The antibody that binds to the oxidized LDL/$\beta_2$GPI complex refers to an antibody that binds to the complex formed between oxidized LDL and plasma glycoprotein $\beta_2$GPI in arteriosclerotic plaques. Specifically, such antibodies include, but are not limited to:

(a) an antibody comprising a heavy chain that comprises CDR1 having the amino acid sequence of SEQ ID NO: 54, CDR2 having the amino acid sequence of SEQ ID NO: 55, and CDR3 having the amino acid sequence of SEQ ID NO: 56;

(b) an antibody comprising a heavy chain that comprises a heavy-chain variable region having the amino acid sequence of SEQ ID NO: 53;

(c) an antibody comprising a light chain that comprises CDR1 having the amino acid sequence of SEQ ID NO: 59, CDR2 having the amino acid sequence of SEQ ID NO: 60, and CDR3 having the amino acid sequence of SEQ ID NO: 61;

(d) an antibody comprising a light chain that comprises a light-chain variable region having the amino acid sequence of SEQ ID NO: 58; and (e) an antibody comprising a pair of the heavy chain of (a) or (b) above and the light chain of (c) or (d) above.

DNAs encoding an antibody that binds to the oxidized LDL/$\beta_2$GPI complex include, but are not limited to:

(a) a heavy chain-encoding DNA that comprises the nucleotide sequence of SEQ ID NO: 57;

(b) a light chain-encoding DNA that comprises the nucleotide sequence of SEQ ID NO: 62;

(c) a DNA encoding a heavy chain that comprises CDR1 having the amino acid sequence of SEQ ID NO: 54, CDR2 having the amino acid sequence of SEQ ID NO: 55, and CDR3 having the amino acid sequence of SEQ ID NO: 56; and (d) a DNA encoding a light chain that comprises CDR1 having the amino acid sequence of SEQ ID NO: 59, CDR2 having the amino acid sequence of SEQ ID NO: 60, and CDR3 having the amino acid sequence of SEQ ID NO: 61.

In the immunological methods, calcification sites and arteriosclerosis sites in arteriosclerotic plaques are detected using as an indicator the binding activities (amounts of binding) of an antibody of the present invention and an antibody that binds to the oxidized LDL/$\beta_2$GPI complex. Such immunological methods enable rapid and sensitive detection. In addition, the procedures of the methods are simple.

In immunohistochemical staining, generally, the step of contacting test pathological tissues with an antibody of the present invention is carried out, and then the binding amounts of the antibody of the present invention and antibody that binds to the oxidized LDL/$\beta_2$GPI complex are determined. Specifically, the method of the present invention can be achieved according to the immunohistochemical staining method described below.

In general, biological tissues are immunohistochemically stained by the procedure described below in (1) to (9). Various documents and books are available on immunohistochemical staining of biological tissues (for example, "Kouso Koutai Hou (Enzyme labeled antibody method) Revised 3rd edition", eds., Keiichi Watanabe and Kazuo Nakane, Gakusai Kikaku).

(1) Fixation and Paraffin Embedding

Surgically collected biological tissues are fixed in formalin, paraformaldehyde, anhydrous ethyl alcohol, or such. Then, the tissues are embedded in paraffin. In general, after dehydration with alcohol, the tissues are treated with xylene, and finally embedded in paraffin. The paraffin-embedded samples are sliced into sections of a desired thickness (for example, 3 to 5 µm), and placed flat on glass slides. Sometimes, alcohol-fixed sample, dried and mounted samples, frozen samples, and the like are used instead of paraffin-embedded samples.

(2) Deparaffinization

In general, samples are treated in succession by xylene, alcohol, and purified water.

(3) Pre-Treatment (Unmasking of Antigen)

If needed, enzyme treatment, thermal treatment, pressure treatment, and/or the like are carried out to unmask antigens.

(4) Blocking of Endogenous Peroxidase

When peroxidase is used as a labeling substance in the staining, the endogenous peroxidase activity should be blocked in advance by the treatment with hydrogen peroxide solution.

(5) Blocking of Non-Specific Reaction

The sections are treated with a bovine serum albumin solution (for example, 1% solution) for about several minutes to several tens of minutes to inhibit non-specific reaction. However, this step may be omitted when the primary antibody reaction is carried out using an antibody solution containing bovine serum albumin.

(6) Primary Antibody Reaction

The antibody which has been diluted to an appropriate concentration is dripped onto the sections on glass slides. Then, the sections are incubated for several tens of minutes to several hours. After incubation, the sections are washed with an appropriate buffer such as phosphate buffer.

(7) Addition of Labeling Reagent

Peroxidase is commonly used as a labeling substance. A peroxidase-conjugated secondary antibody is dripped onto the sections on glass slides. Then, the sections are incubated for several tens of minutes to several hours. After incubation, the sections are washed with an appropriate buffer such as phosphate buffer.

(8) Chromogenic Reaction

DAB (3,3'-diaminobenzidine) is dissolved in Tris buffer, and then a hydrogen peroxide solution is added thereto. The resulting chromogenic solution is allowed to permeate into the sections for several minutes (for example, five minutes) to develop color. After color development, the sections are sufficiently washed with tap water to remove DAB.

(9) Nuclear Staining

Nuclear staining is carried out by reacting Mayer's Hematoxylin for several seconds to several tens of seconds. The sections are allowed to develop color when washed under running water (generally, several minutes).

(10) Dehydration, Clearing, and Mounting

After alcohol dehydration, clearing treatment is carried out using xylene. Finally, the sections are mounted with synthetic resins, glycerin, gum syrup, or such.

When a labeled antibody of the present invention and a labeled antibody that binds to the oxidized LDL/$\beta_2$GPI complex are used, the amount of bound antibodies can be directly determined using the amount of label as an indicator. Such method is simpler but has problems. The detection sensitivity of the method is generally lower, and it is necessary to prepare labeled antibodies of the present invention and labeled antibodies that bind to the oxidized LDL/$\beta_2$GPI complex. Thus, it is more preferable to use indirect detection methods which include methods using a secondary antibody linked to a labeling substance, and methods using a polymer linked to a secondary antibody and labeling substance. The secondary antibody refers to an antibody that has the activity of specifically binding to an antibody of the present invention and an antibody that binds to the oxidized LDL/$\beta_2$GPI complex. For example, an anti-rabbit IgG antibody can be used when the antibody of the present invention and antibody that binds to the oxidized LDL/$\beta_2$GPI complex are rabbit antibodies. Labeled secondary antibodies that can be used to detect antibodies of various animal species such as rabbit, goat, and mouse are available on the market (for example, Funakoshi and Cosmo Bio Co.). Thus, appropriate antibodies may be selected and used according to the antibody of the present invention and antibody that binds to the oxidized LDL/$\beta_2$GPI complex.

Any one selected from peroxidase, $\beta$-D-galactosidase, microperoxidase, horseradish peroxidase (HRP), fluorescein isothiocyanate (FITC), Rhodamine isothiocyanate (RITC), alkaline phosphatase, biotin, and radioactive substances is preferably used as a labeling substance. In particular, high sensitivity detection can be achieved by methods that react avidin peroxidase with biotin which is used as a labeling substance.

The present invention relates to methods for detecting the disease state of arteriosclerosis, which comprise the steps of:

(a) contacting an isolated arteriosclerotic plaque with an antibody that has reactivity toward calcified globules (NLO) and activity to bind to arteriosclerotic plaques (in particular, calcified arteriosclerotic lesions);

(b) detecting a calcification site and an atheroma or sites of early calcified lesion and early atheroma in the arteriosclerotic plaques; and (c) judging whether an arteriosclerotic plaque is detected by the antibody that has the activity of binding to arteriosclerotic plaques (in particular, calcified arteriosclerotic lesions) or by the antibody that binds to the oxidized LDL/$\beta_2$GPI complex.

Tissue sections can be double-strained using labels that allow identification of the antibody of the present invention and the antibody that binds to the oxidized LDL/$\beta_2$GPI complex (two types of labels that can be identified with different wavelengths, and their corresponding fluorescence filters, and such). As described below in the Examples, there are subtle differences in the sites and structures detected in such double staining. Since calcified lesions are present at the sites detected by the antibody of the present invention and abnormal lipid structures are present at the sites detected by the antibody that binds to the oxidized LDL/$\beta_2$GPI complex, these antibodies can be used to assess the presence of lesions. Thus, such detection is effective to judge and diagnose lesions.

All prior art documents cited in the specification are incorporated herein by reference.

EXAMPLES

Hereinbelow, the present invention will be specifically described with reference to the Examples, but is not to be construed as being limited to the illustrative embodiments described in the Examples.

Example 1

Preparation of Calcified Globules

First, stones derived from surgically excised human urinary calculi were dissolved with 1N HCl according to literature (Non-patent Document 1: Nanobacteria: an alternative mechanism for pathogenic intra- and extracellular calcification and stone formation, Proc. Natl. Acad. Sci. USA, 1998, Jul. 7; 95(14): 8274-9). After neutralization and filtration sterilization, the sample was incubated in DMEM containing 10% FCS for three weeks. The culture medium was centrifuged at 10,000 RPM for 30 minutes to collect the calcified globules (NLO).

Alternatively, according to the protocol by Dr. Ciftcioglu and Non-patent Document 1, the Nanobacterium (NNb) line, which was a gift from Dr. Neva Ciftcioglu (NASA, USA), was incubated under 5% $CO_2$ at 37° C. in DMEM containing 10% FBS irradiated with $\gamma$-ray. The line could be continuously subcultured for passage while under monitoring with a phase contrast microscope. NLO derived from NNb can be collected by 30 minutes of centrifugation at 9,000 rpm and 20° C.

Furthermore, the Pst19 line was obtained from a massive urinary calculus surgically excised from a male of age 50 in Paraguay. A portion of the calculus was crushed in a mortar and then a small volume of 1N HCl was added thereto. After the resulting emulsion was centrifuged at a low speed (3,000 rpm for five minutes), the supernatant obtained was neutralized with 1 N NaOH and filtered through a filter with 0.45 µm pores. A 1-ml aliquot was added to 5 ml of DMEM containing 10% FBS irradiated with $\gamma$-ray, and the mixture was incubated according to Non-patent Document 1. Small particles similar to those observed in the case of NNb were seen under a phase contrast microscope three weeks after the start of incubation. Thus, the Pst19 line could be passaged by subculture. As in the case of NNb, NLO derived from Pst19 can be collected by 30 minutes of centrifugation at 9,000 rpm and 20° C.

Alternatively, calcified globules (Gibco Hap) can be obtained by the method described below. 200 ml of thermally inactivated FBS (Gibco), which had been used in culturing cells of an established cell line, was centrifuged at 10,000 rpm and 4° C. for 60 minutes. The small amount of precipitate obtained was collected with 5 ml of DMEM containing 10% FBS irradiated with $\gamma$-ray, and treated by sonication for 30 seconds to disperse the precipitate. The resulting sample was incubated under 5% $CO_2$ at 37° C. Small particles were seen under a phase contrast microscope after six months and 14 days. Thus, calcified globules could be passaged by subculture. NLO was collected by centrifugation in the same manner as for NNb and Pst19.

Example 2

Antibody Preparation

Preparation of Monoclonal Antibody

Using Freund's adjuvant, BALB/c mice were subcutaneously immunized several times with calcified globules (NLO) or homogenate of arteriosclerotic plaques from human abdominal aorta. The spleen cells obtained were fused with cells of the P3U1 myeloma line by the polyethylene glycol method. The fused cells were screened by ELISA using anti-calcified globule IgM antibody and ELISA using anti-oxidized LDL IgM antibody, in which the antibody titer of culture supernatant was used as an indicator. Hybridomas that produce the specific antibody were cloned by the limiting dilution method.

ELISA Using Anti-Calcified Globule IgM Antibody

Figure 1:
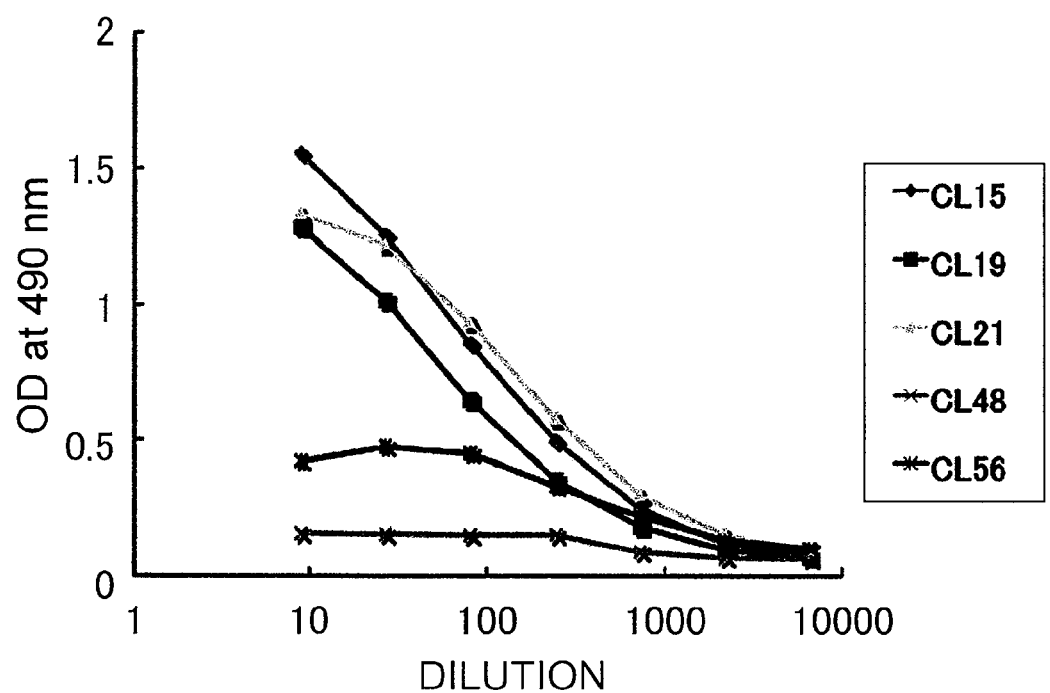
FIG. 1 is a graph showing the reactivity of antibodies in hybridoma culture supernatants to calcified globules. Immediately after establishment of hybridomas, culture supernatants were assayed by ELISA to assess the anti-calcified globule IgM antibody during the screening process. The vertical axis indicates the absorbance (490 nm), and the horizontal axis indicates the dilution fold of culture supernatants.

NLO was amplified at 37° C. under 5% $CO_2$ in Dulbecco's modified MEM (DMEM) containing 10% FCS irradiated. The resulting NLO was washed with DMEM. 80 µl of NLO of 0.2 OD (650 nm) was added to each well of 96-well culture plates (Greiner). After one day of incubation at 37° C., the NLO was further incubated in 0.4% paraformaldehyde (PFA; in PBS) overnight. After washing three times with PBS, the plates were blocked with PBS containing 0.5% BSA (at room temperature for one hour). Test samples (culture supernatants appropriately diluted with PBS containing 0.1% BSA) were incubated in the plates at room temperature for one hour. After the plates were washed three times with PBS containing 0.05% Tween 20 (PBS-Tween), an HRP-labeled anti-mouse IgM antibody was incubated in the plates at room temperature for one hour. After the plates were washed three times with PBS-Tween, 0.03% $H_2O_2$ and 0.1 M citrate buffer (pH 3.0) containing 0.4 mg/ml orthophenylenediamine (OPD) were added to the plates. After ten minutes of incubation, the reaction was stopped by adding an equal volume of 2N $H_2SO_4$. Absorbance was measured at 490 nm (FIG. 1). The data shown in FIG. 1 were obtained by assaying the culture supernatants immediately after establishment of hybridoma, and thus do not reflect the actual antibody affinity.

Example 3

Analysis of Antibody Properties

ELISA Using Anti-Oxidized LDL Antibody

Figure 2:
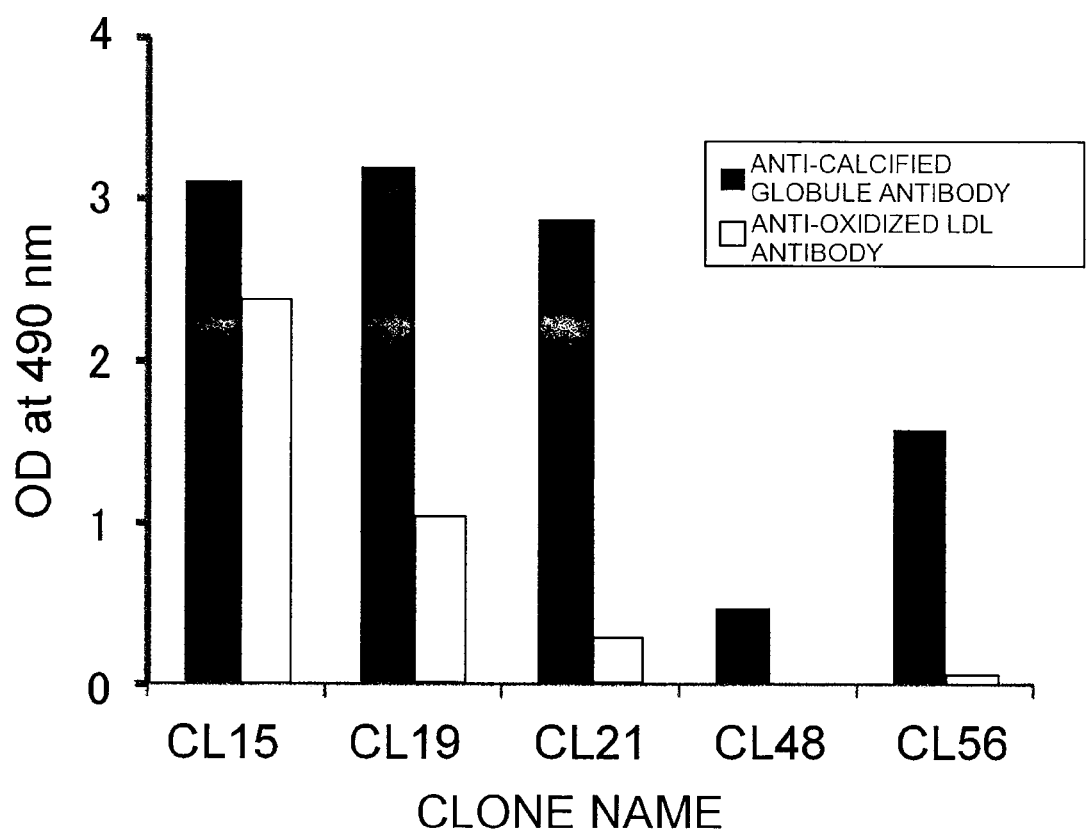
FIG. 2 is a graph showing the reactivity of anti-calcified globule monoclonal antibody to oxidized LDL. The graph shows the reactivities of monoclonal antibodies (produced by established five hybridoma clones) to calcified globules (NLO) and oxidized LDL.

50 µl of 4 µg/nl human LDL oxidatively modified by copper sulfate was added to each well of 96-well microtiter plates (Immulon-2), and incubated at 4° C. overnight. After washing with PBS-Tween, the plates were blocked with 0.5% BSA-PBS. Test samples (culture supernatants appropriately diluted with PBS containing 0.1% BSA) were incubated in the plates at room temperature for one hour. After the plates were washed three times with PBS-Tween, an HRP-labeled anti-mouse IgM antibody was incubated in the plates at room temperature for one hour. After the plates were washed three times with PBS-Tween, 0.03% $H_2O_2$ and 0.1 M citrate buffer (pH 0.0) containing 0.4 mg/ml orthophenylenediamine (OPD) were added to the plates. After ten minutes of incubation, the reaction was stopped by adding an equal volume of 2N $H_2SO_4$. Absorbance was measured at 490 nm (FIG. 2). FIG. 2 is a graph showing the reactivities of monoclonal antibodies to NLO and oxidized LDL. The monoclonal antibodies were produced by hybridomas of the established five clones.

ELISA Using Anti-Lipid Antibody

Figure 3:
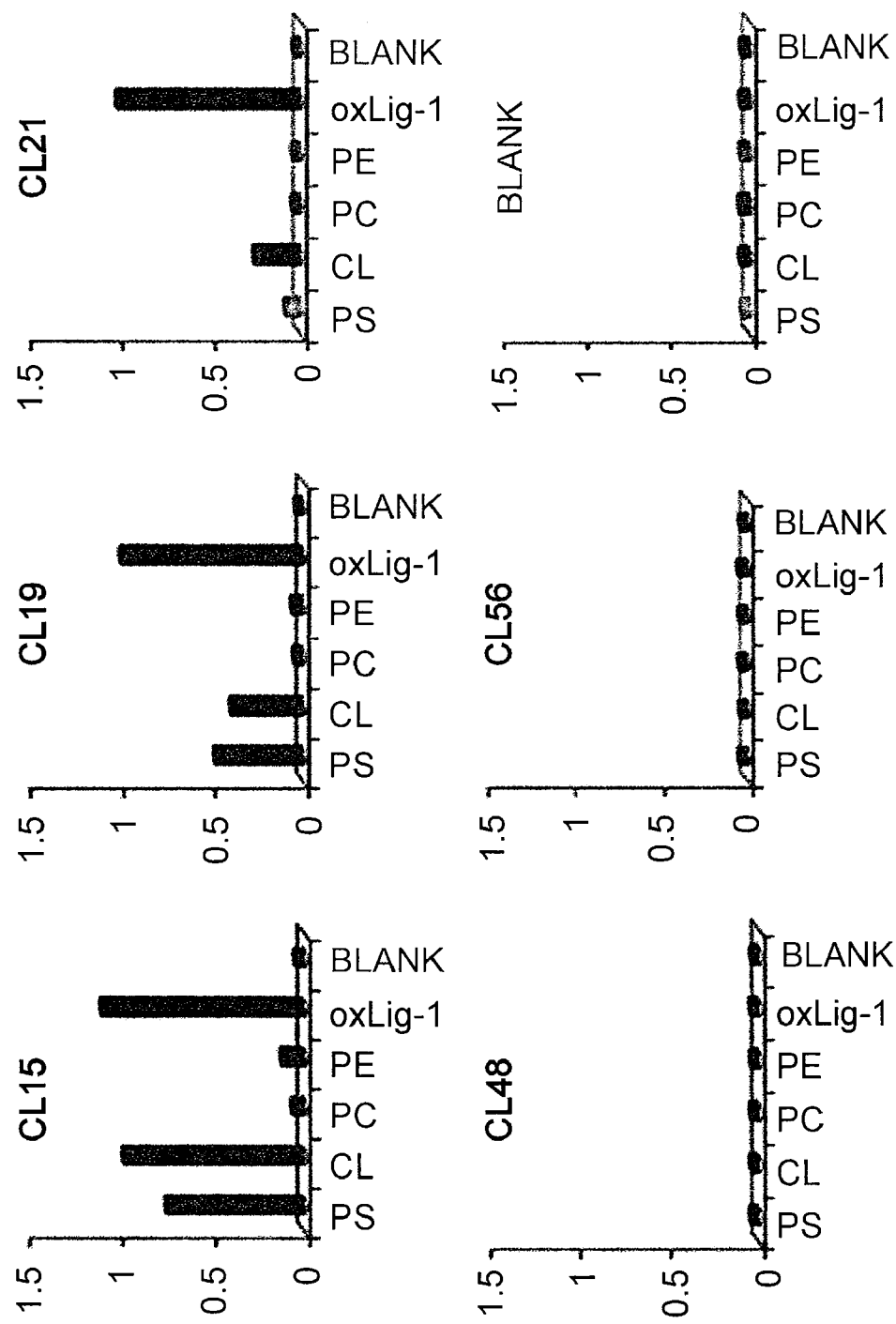
FIG. 3 is graphs showing the reactivities of monoclonal antibodies to various lipids in ELISA. The vertical axis indicates the absorbance (490 nm), and the horizontal axis indicates clone name. The graphs show the reactivities of five monoclonal antibodies to various lipids. ELISA demonstrated that CL15 and CL19 were reactive to PS, CL, and oxLig-1. The features of recognition by CL21 are as follows: CL21 was reactive to CL and oxLig-1; CL21 was also reactive to PS, although its binding activity was smaller than those of CL15 and CL19. CL48 and CL56 were reactive to calcified globules (NLO); however, they were non-reactive to all of the lipids used in the present invention.
Figure 4:
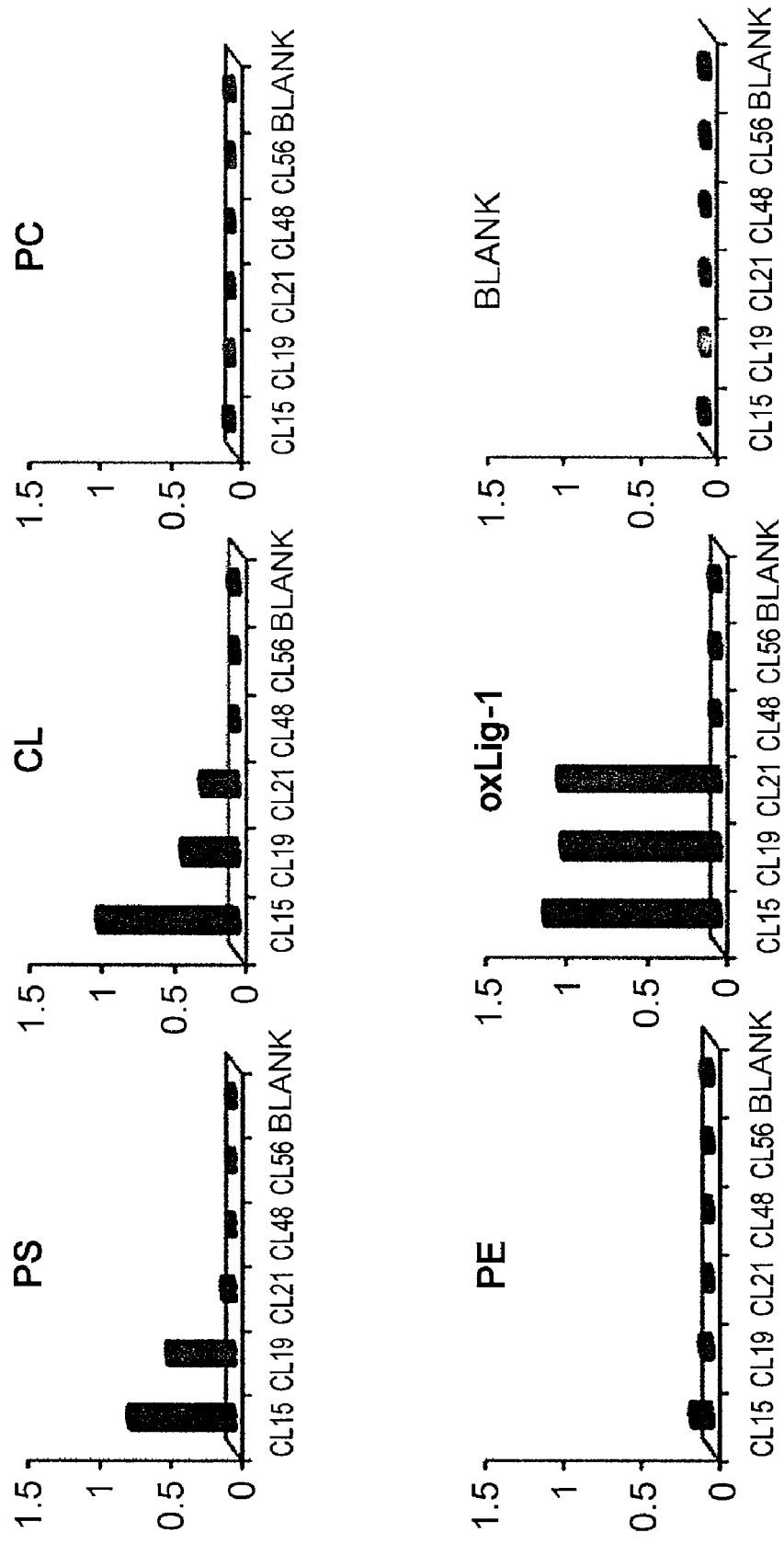
FIG. 4 is graphs showing the reactivities of monoclonal antibodies to various lipids in ELISA. The vertical axis indicates the absorbance (490 nm), and the horizontal axis indicates clone name. The graphs show the reactivities of five monoclonal antibodies to various lipids. Antibodies that strongly bind to PS are CL15 and CL19. CL21 is also expected to bind to PS, although its reactivity is smaller than those of CL15 and CL19. Antibodies reactive to CL were CL15, CL19, and CL21. Antibodies reactive to oxLig-1 were CL15, CL19, and CL21.

Phosphatidylserine (PS; derived from bovine brain), cardiolipin (CL; derived from bovine heart), dioleoylphosphatidylcholine (PC), dioleoylphosphatidylethanolamine (PE), dioleoyl phosphatidylserine (PS), and 7-ketocholesteryl-9-carboxynonanoate (oxLig-1) were diluted to 50 µg/ml with ethanol, and aliquoted (50 µl) to 96-well microtiter plates (Immulon-1). After air-drying, the plates were blocked with 0.5% BSA-PBS. Test samples (culture supernatants appropriately diluted with PBS containing 0.1% BSA) were incubated in the plates at room temperature for one hour. After the plates were washed three times with PBS containing 0.05% Tween 20 (PBS-Tween), an HRP-labeled anti-mouse IgM antibody was incubated in the plates at room temperature for one hour. After the plates were washed three times with PBS-Tween, 0.03% $H_2O_2$ and 0.1 M citrate buffer (pH 0.0) containing 0.4 mg/ml orthophenylenediamine (OPD) were added to the plates. After ten minutes of incubation, the reaction was stopped by adding an equal volume of 2N $H_2SO_4$. Absorbance was measured at 490 nm (FIGS. 3 and 4). ELISA showed that CL15 and CL19 were reactive to PS, CL, and oxLig-1. The recognition properties of CL21 are reactive to CL and oxLig-1; and reactive to PS although its binding activity was smaller than those of CL15 and CL19. CL48 and CL56 were reactive to calcified globules; however, they exhibited no reactivity towards any of the lipids used in the present invention (FIG. 3).

Antibodies that strongly bind to PS were CL15 and CL19. CL21 is also expected to bind to PS, although its reactivity was smaller than those of CL15 and CL19. Meanwhile, antibodies reactive to CL were CL15, CL19, and CL21. Antibodies reactive to oxLig-1 were CL15, CL19, and CL21 (FIG. 4).

As described in the Examples below, these antibodies were shown to bind to both calcified globules and arteriosclerotic lesions.

Example 4

Antibody Staining of Tissues

Immunostaining

Antibodies were assessed by immunohistochemical staining of arteriosclerotic plaques.

ApoE$^{-/-}$ mice and LDLR$^{-/-}$ mice (obtained from Jackson Lab, and maintained in the animal experiment facility at Okayama University) were fed a common diet (Oriental Yeast NMF) up to eight weeks old, and then fed a high fat diet (common diet additionally containing 1% cholesterol, 1% cholic acid, and 15% salt-free butter) for four to six months. As a result, arteriosclerotic plaques developed, and thus thickening and atheroma were observed in the thoracic or abdominal aortae. Then, these eight-month-old mice were sacrificed, and cryosections of the thoracic aorta, and aortic root and valves were prepared from the mice and observed as samples.

The prepared cryosections were fixed with paraformaldehyde and then used in the experiment of fluorescent antibody immunostaining.

Labeling of Monoclonal Antibody with Cy5.5

Various monoclonal antibodies (1 mg/ml) were dialyzed against 0.1 M carbonate buffer (pH 9.3) at 4° C. overnight, and each was transferred into Fluorolink Cy5.5 monofunctional dye (1 tube). After 30 minutes of incubation at room temperature, the antibodies were treated with a SephadexG-25 column to yield Cy5.5-labeled antibody.

Fluorescent Immunostaining of Cryosections

Sections were fixed with 1% paraformaldehyde for five minutes, and then incubated with various monoclonal antibodies at 4° C. overnight. After washing, the sections were incubated with an FITC-labeled anti-mouse IgG or IgM antibody (secondary antibody) at room temperature for one hour. Staining with DAPI and Rhodamine Phalloidin was carried out by addition with the secondary antibody at the time of incubation. Then, the sections were observed and photographed under a fluorescent microscope.

Figure 5:
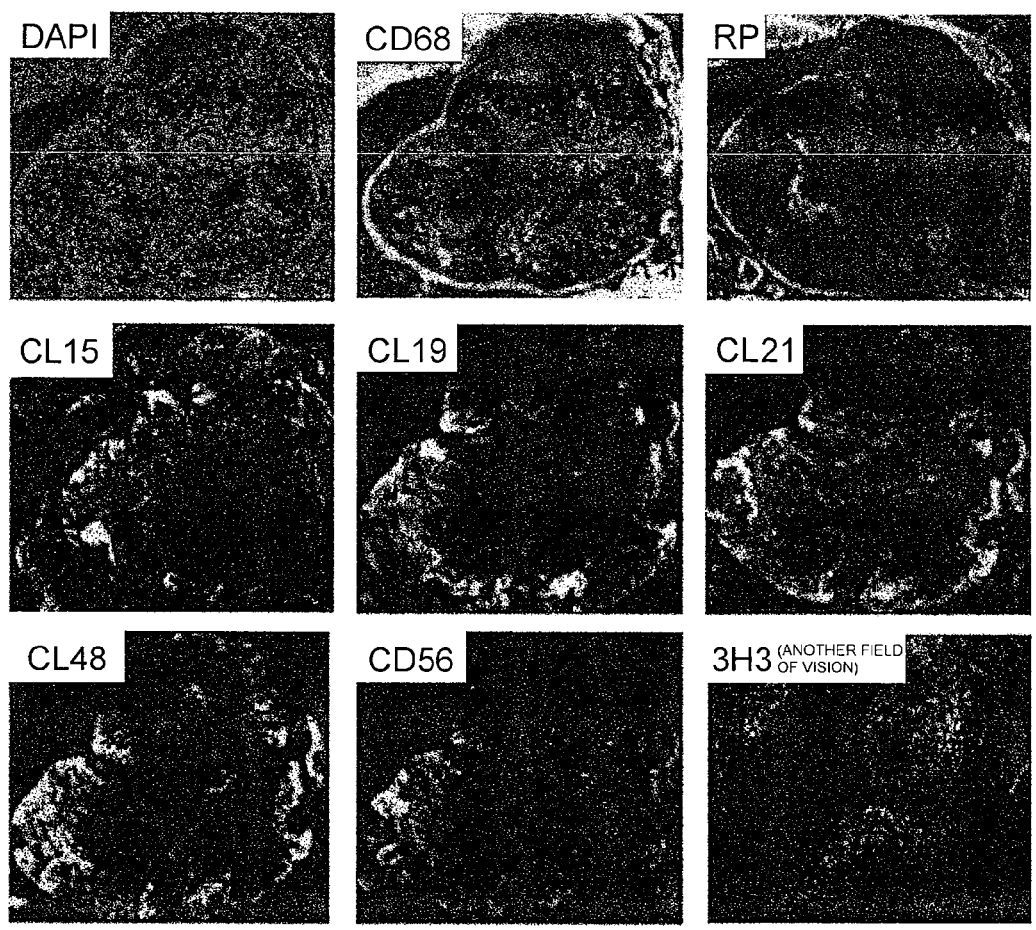
FIG. 5 is photographs showing immunostaining of aortic valves using calcified globule-specific monoclonal antibodies. Unlike 3H3, these antibodies strongly stain the peripheral area rather than atheroma itself. The selection pattern is subtly different from antibody to antibody.

As shown in FIG. 5, when antibodies CL15 to CL56 were used, they specifically stained the region adjacent to the aortic valve (area near the muscle layer). The region was different from the antibody 3H3-stainable location of atheroma clustered with macrophages. However, there were subtle differences in the staining pattern depending on the type of anti-calcified globule antibody.

Example 5

Immunoelectron Microscopy Using Antibodies

Figure 6:
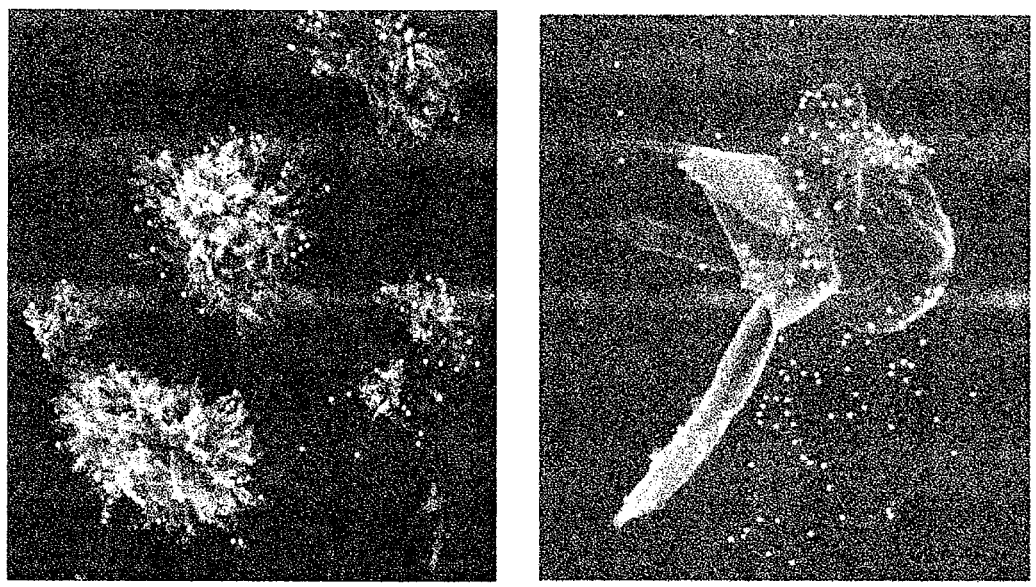
FIG. 6 is photographs showing immunoelectron microscopic images observed using monoclonal antibody CL21 against calcified globules (the target sample was cultured calcified globules). Scanning electron microscope, Hitachi S900. The backscattered electron image is superimposed onto the secondary electron image, and then colloidal gold was marked as a yellow dot.

FIG. 6 shows photographs of immunoelectron microscopic images obtained using a monoclonal antibody against calcified globules (the target sample was cultured calcified globules). A scanning electron microscope, Hitachi 5900, was used. The backscattered electron image is superimposed onto the secondary electron image, and then colloidal gold was marked as a yellow dot (FIG. 6).

FIG. 6 shows that antibodies CL15 and CL21 were reactive to calcified globules (NLO). Specifically, CL21 binds to the lipid membrane-like structure (lamella) coexistent with calcified globules.

Example 6

The Inhibitory Activity of Antibody CL21 on Calcification Progression

Figure 15:
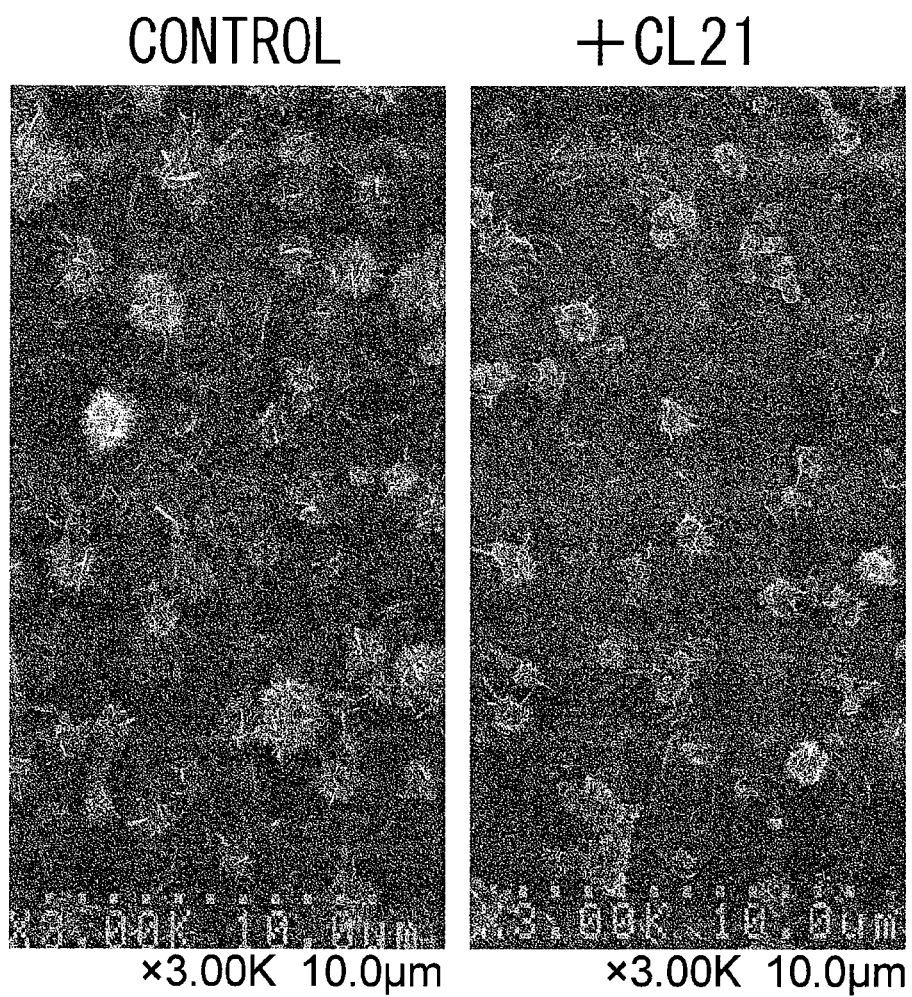
FIG. 15 is photographs showing a (phase-contrast electron microscopic) observation on inhibition of the growth of calcified globules. When added during in vitro amplification of calcified globules, antibody CL21 markedly inhibited the formation of lamellar structure associated with the generation of calcified globules, thereby suppressed the formation of globules (the white line shape corresponds to the lamellar structure).

Previously conducted preliminary experiments have revealed that when incubated in PBS (—Mg) (phosphate buffer saline containing calcium but without magnesium) containing 10% DMEM irradiated with γ-ray, both NNb and Pst19 efficiently form lamella (lipid membrane-like structure). Based on this result, the effect of antibody CL21 on lamellar formation in the medium was assessed using a high-resolution scanning electron microscope (SEM), after adding a final concentration of 250 μg/ml of antibody CL21 to 10% DMEM (without FBS) irradiated with γ-ray (CL21 was added at 50 μg/ml for the first week, and then at 200 μg/ml; and after incubation, culture was continued for one week under 5% $CO_2$ at 37° C.). The result showed that CL21 markedly inhibited (or retarded) the lamellar formation (FIG. 15).

To assess the effect of γ-ray irradiation of FBS on calcified globules, defatted Pst19 (after long period of incubation, Pst19 was defatted by the Folch method) was incubated in DMEM containing 10% FBS of an identical lot after or without γ-ray irradiation. The resulting two OD650 values were compared to each other, and at the same time SEM samples were prepared at the time of OD650 measurement. The result showed that the OD value with γ ray-irradiated FBS was markedly increased as compared to non-irradiated FBS.

Example 7

Ligand Blotting

Thin Layer Chromatography Using Silica Gel Plate

Various lipids (PS, CL, etc.) were spotted onto a thin layer silica gel plate, and fractionated using a developing solvent of chloroform/methanol/ammonia/water. After drying, the plates were blocked with PBS containing BSA and polyvinylpyrrolidine. Following wash, monoclonal antibody and HRP-labeled anti-mouse IgM antibody were reacted in succession, and then hydrogen peroxide solution and 4-methoxy-1-naphtol were added for chromogenic reaction. The result showed that CL15 and CL19 were highly reactive to phosphatidylserine (derived from bovine brain) (data not shown).

The present inventors immunized BALB/c mice with urinary calculus-derived calcified globules (NLO) or carotid artery-derived arteriosclerotic plaques, and then carried out cell fusion to establish cell lines producing monoclonal antibodies that specifically react to calcified globules. Table 1 shows monoclonal antibodies that are specific to calcified globules.

TABLE 1

MONOCLONAL ANTIBODIES SPECIFIC TO CALCIFIED GLOBULES

| CLONE NAME | IMMUNOGEN ELISA | SUBCLASS LIGAND | SPECIFICITY | | | | | |
|---|---|---|---|---|---|---|---|---|
| | | | CALCIFIED GLOBULE | OXIDIZED LDL | PS | CL | oxLig-1 | BLOT |
| CL15 | CALCIFIED GLOBULE | μ, κ | +++ | +++ | ++ | ++ | +++ | PS |
| CL19 | CALCIFIED GLOBULE | μ, κ | +++ | + | ++ | + | +++ | PS |
| CL21 | CALCIFIED GLOBULE | μ, κ | +++ | +/− | + | + | +++ | |
| CL48 | PLAQUE | μ, κ | + | − | − | − | − | |
| CL56 | PLAQUE | μ, κ | + | − | − | − | − | |

CL15, CL19, and CL21 are monoclonal antibodies established from mice immunized with calcified globules NLO, while CL48 and CL56 are monoclonal antibodies established from mice immunized with a homogenate of arteriosclerotic plaques from human abdominal aorta. All of these antibodies are specific to calcified globules (NLO). These five antibodies are all IgM, and their reactivities to various lipids are shown in Table 1. PS, phosphatidylserine; CL, cardiolipin; oxLig-1, 7-ketocholesteryl-9-carboxynonaoate. Furthermore, ligand blotting (specifically, a method for testing antibody reactivity in which various lipids are fractionated by thin layer chromatography using silica gel plate and then the plate is subjected to ELISA) was used to demonstrate that CL15 and CL19 are reactive to PS.

Example 8

Nucleotide Sequence Analysis of Anti-Calcified Globule Antibody

The H chain and L chain V regions of anti-calcified globule antibodies were analyzed by nucleotide sequencing.

Five clones of hybridomas were analyzed and they were CL15-203 (abbreviated as CL15), CL19-107 (abbreviated as CL19), CL21-35 (abbreviated as CL21), CL48-139 (abbreviated as CL48), and CL56-369 (abbreviated as CL56). Antibodies secreted from the hybridomas were tested immunologically, and the result showed that all antibodies were of the IgM/κ class. Thus, the sequences of H chain CH4 region (secretory form) and κ chain C region of mouse IgM were searched against the Kabat database (Sequences of proteins of immunological interest, 5th edition, 1991), and primers were designed to be homologous to each terminal portion. The primers are shown below.

```
(1) Mouse IgM HC priR:
                                        (SEQ ID NO: 51)
    5'-TCAATAGCAGGTGCCGCCTGTGTCAGAC-3'

(2) Mouse Ig KC priR:
                                        (SEQ ID NO: 52)
    5'-TCAACACTCATTCCTGTTGAAGCTCTTGACAATGGGTG-3'
```

Complementary DNAs of antibody genes of interest were amplified from total RNA of each hybridoma by RT-PCR using GeneRacer Kit (Invitrogen). The H chain was amplified using GeneRacer 5' primer included in the kit and the primer of (1), while the L chain was amplified using GeneRacer 5' primer and the primer of (2).

The procedure is as follows: an RNA oligo having a sequence that serves as a template for GeneRacer 5' primer is ligated selectively to the full-length mRNA in the total RNA using the above-described kit. Then, using GeneRacer 5' primer, and the primer of (1) or (2), RT-PCR is carried out to amplify the gene in the region located between the two primers.

The resulting PCR products contain unrelated DNAs in addition to DNAs encoding the antibody genes of interest. Thus, the DNAs were fractionated by agarose gel electrophoresis, and bands corresponding to the sizes of the antibody genes were excised from the gel. The DNAs were extracted and cloned using Zero Blunt TOPO PCR Cloning Kit (Invitrogen), and then sequenced. Specifically, 24 H-chain clones and 24 L-chain clones were selected from many clones obtained from each hybridoma, and sequenced with CEQ8800 (BECKMAN COULTER). The determined sequences were confirmed to be mouse antibody sequences using the function of IgBLAST provided on the NCBI site.

The sequence of V region was analyzed by sequencing, and mouse V regions having a homologous sequence were searched using NCBI IgBLAST. As a result, of the 24 clones in each group obtained by cloning, four or more clones were revealed to have an identical mouse antibody sequence.

When there are multiple clones with completely the same nucleotide sequence for an antibody, it is assumed to be the antibody sequence of interest. However, there is a possibility that the detected sequence is the antibody sequence derived from P3U1 cell which is the fusion partner of the hybridoma. The parental line of P3U1 is MOPC-21, and P3U1 is known to produce the same κ chain as that of MOPC-21 (not produce H chain). Thus, the L chain V region of the obtained mouse antibody sequence was compared to the κ chain V region of MOPC-21 for homology. This test showed that the two variable regions were different. Finally, the H chain and L chain were confirmed to be IgM and κ, respectively, by sequencing the C region.

Next, some clones were excluded because they have mutations or their V regions were only partially analyzed due to interruptions in the sequence peak profile. Thus, the clones were narrowed down to 3 to 8 by selecting those sharing a 100% identical V region sequence. Furthermore, the L-chain V region was compared to that of MOPC-21 to assess their homology. The result demonstrated that the homology was about 60% to 70%, and thus the L chain was not derived from MOPC-21.

The clones described above were also analyzed for their constant regions, in addition to the V regions. The result demonstrated that the H chain and L chain were IgM and κ, respectively. The SEQ IDs of amino acid (FIG. 8) and nucleotide sequences of each clone are listed below.

Then, CDRs were identified from the antibody sequences. The SEQ IDs of CDR sequences of each clone are listed below.

The nucleotide and amino acid sequences of each clone are shown in the Sequence Listing according to the SEQ IDs shown below.

<CL15>
SEQ ID NO: 1, the amino acid sequence of heavy chain CDR1
SEQ ID NO: 2, the amino acid sequence of heavy chain CDR2
SEQ ID NO: 3, the amino acid sequence of heavy chain CDR3
SEQ ID NO: 4, the amino acid sequence of heavy-chain variable region
SEQ ID NO: 5, the nucleotide sequence of heavy-chain variable region
SEQ ID NO: 6, the amino acid sequence of light chain CDR1
SEQ ID NO: 7, the amino acid sequence of light chain CDR2
SEQ ID NO: 8, the amino acid sequence of light chain CDR3
SEQ ID NO: 9, the amino acid sequence of light-chain variable region
SEQ ID NO: 10, the nucleotide sequence of light-chain variable region <CL19>
SEQ ID NO: 11, the amino acid sequence of heavy chain CDR1
SEQ ID NO: 12, the amino acid sequence of heavy chain CDR2
SEQ ID NO: 13, the amino acid sequence of heavy chain CDR3
SEQ ID NO: 14, the amino acid sequence of heavy-chain variable region
SEQ ID NO: 15, the nucleotide sequence of heavy-chain variable region
SEQ ID NO: 16, the amino acid sequence of light chain CDR1
SEQ ID NO: 17, the amino acid sequence of light chain CDR2
SEQ ID NO: 18, the amino acid sequence of light chain CDR3
SEQ ID NO: 19, the amino acid sequence of light-chain variable region
SEQ ID NO: 20, the nucleotide sequence of light-chain variable region <CL21>
SEQ ID NO: 21, the amino acid sequence of heavy chain CDR1
SEQ ID NO: 22, the amino acid sequence of heavy chain CDR2
SEQ ID NO: 23, the amino acid sequence of heavy chain CDR3
SEQ ID NO: 24, the amino acid sequence of heavy-chain variable region
SEQ ID NO: 25, the nucleotide sequence of heavy-chain variable region SEQ ID NO: 26, the amino acid sequence of light chain CDR1

SEQ ID NO: 27, the amino acid sequence of light chain CDR2

SEQ ID NO: 28; the amino acid sequence of light chain CDR3

SEQ ID NO: 29, the amino acid sequence of light-chain variable region

SEQ ID NO: 30, the nucleotide sequence of light-chain variable region

<CL48>

SEQ ID NO: 31, the amino acid sequence of heavy chain CDR1

SEQ ID NO: 32, the amino acid sequence of heavy chain CDR2

SEQ ID NO: 33, the amino acid sequence of heavy chain CDR3

SEQ ID NO: 34, the amino acid sequence of heavy-chain variable region

SEQ ID NO: 35, the nucleotide sequence of heavy-chain variable region

SEQ ID NO: 36; the amino acid sequence of light chain CDR1

SEQ ID NO: 37, the amino acid sequence of light chain CDR2

SEQ ID NO: 38; the amino acid sequence of light chain CDR3

SEQ ID NO: 39; the amino acid sequence of light-chain variable region

SEQ ID NO: 40; the nucleotide sequence of light-chain variable region

<CL56>

SEQ ID NO: 41, the amino acid sequence of heavy chain CDR1

SEQ ID NO: 42, the amino acid sequence of heavy chain CDR2

SEQ ID NO: 43, the amino acid sequence of heavy chain CDR3

SEQ ID NO: 44, the amino acid sequence of heavy-chain variable region

SEQ ID NO: 45, the nucleotide sequence of heavy-chain variable region

SEQ ID NO: 46, the amino acid sequence of light chain CDR1

SEQ ID NO: 47, the amino acid sequence of light chain CDR2

SEQ ID NO: 48, the amino acid sequence of light chain CDR3

SEQ ID NO: 49, the amino acid sequence of light-chain variable region

SEQ ID NO: 50, the nucleotide sequence of light-chain variable region

Example 9

Figure 8:
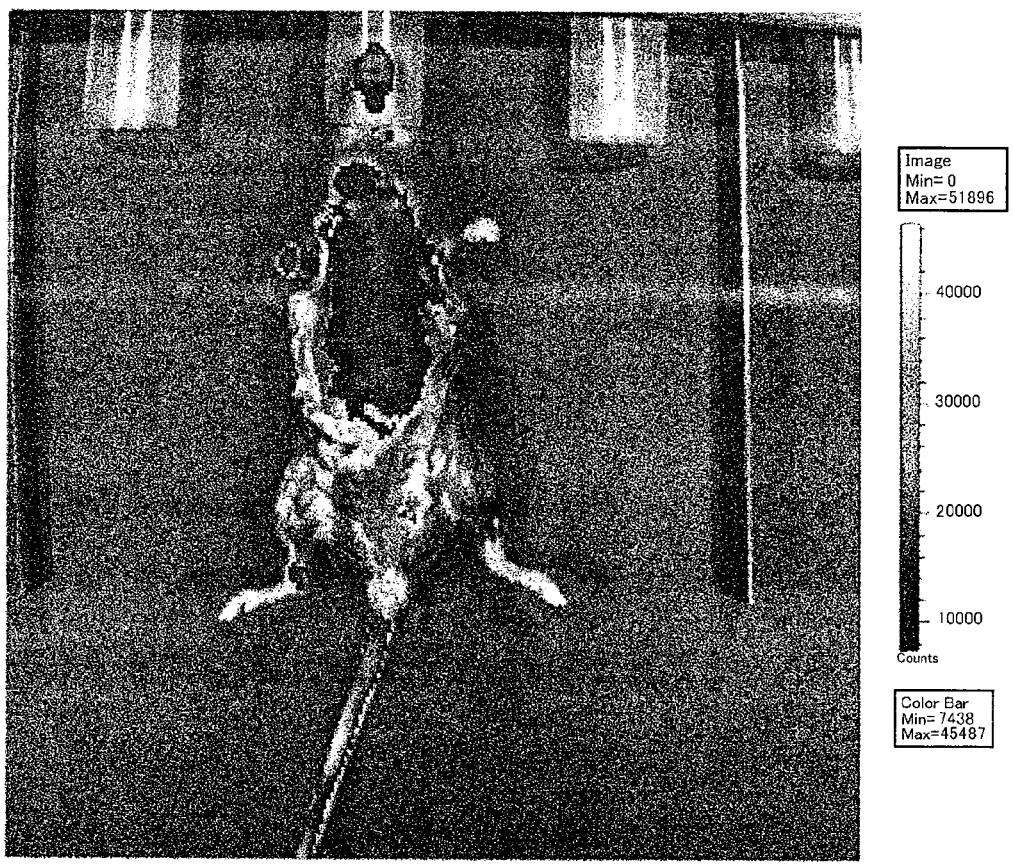
FIG. 8 is a photograph showing an angiographic image using AngioSense. This image is shown for comparison.

Immediately after AngioSense, an angiographic contrast agent, was administered at the caudal vein to apoE$^{-/-}$ mice fed a high fat diet, an angiographic image was observed and photographed using IVIS™ Imaging System, IVIS 200, from Xenogen (FIG. 8).

Example 10

In Vivo Imaging

Imaging was performed using IVIS™ Imaging System, IVIS 200, from Xenogen (excitation, 640 nm; emission, 720 nm).

0.25 mg/ml Cy5.5-labeled antibody CL15 (IgM) was administered at 0.15 ml/head via the caudal vein to apoE$^{-/-}$ mice fed a high fat diet. Twenty hours after administration, the mice were observed and photographed using IVIS 200 (FIG. 9).

When antibody CL15 was administered via the vein, fluorescence was detected around the aortic root and in the thoracic aorta.

Figure 10:
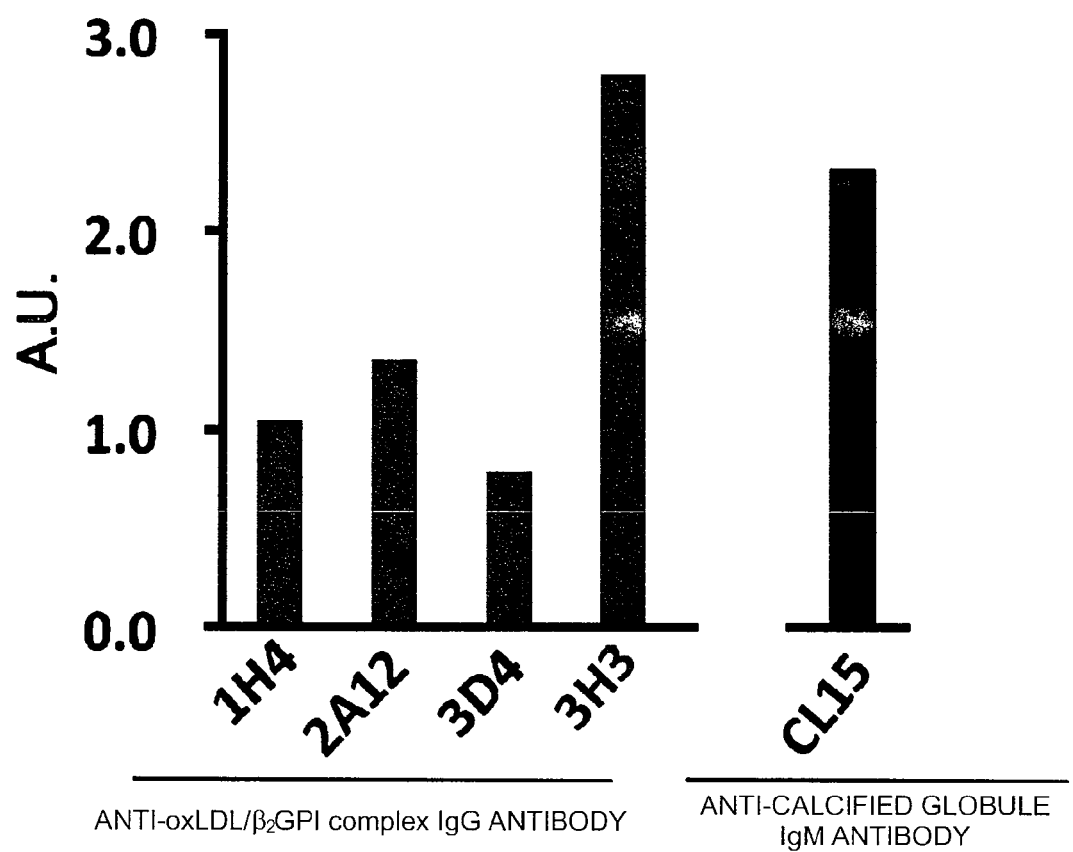
FIG. 10 is a graph showing fluorescence intensity around the aortic root after administration of various Cy5.5-labeled monoclonal antibodies. The fluorescence intensity at the aortic root of a control mouse is taken as 1. Antibodies 3H3 and CL15 can be used for in vivo imaging.

FIG. 10 shows the fluorescence intensity per unit area around the aortic root, which was obtained by digitalization (quantification) based on the data obtained by imaging with IVIS 200. The graph suggests that the imaging can be achieved not only by using antibody 3H3 but also by using other anti-calcified globule antibodies (for example, antibody CL15).

Example 11

Figure 16:
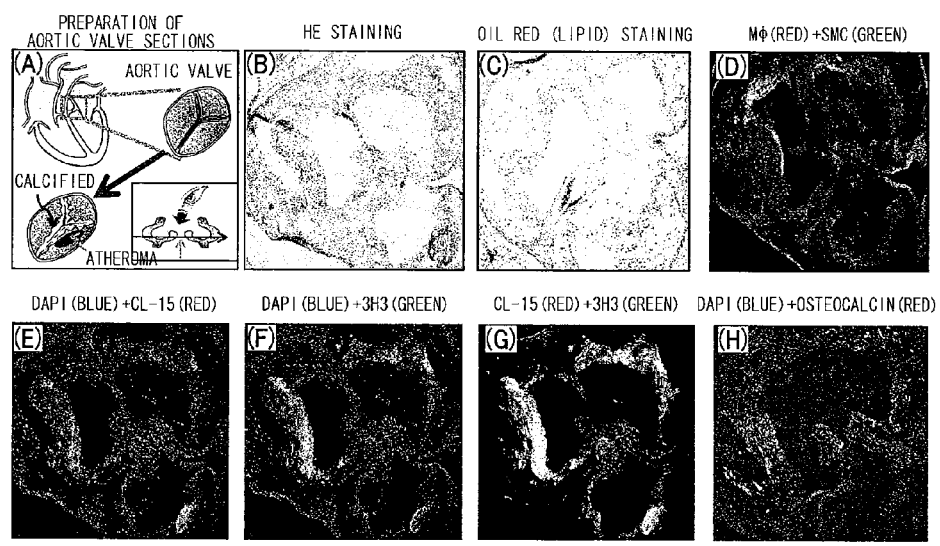
FIG. 16 is a diagram and photographs showing arteriosclerotic plaques (unstable plaques) and early calcified lesions in the aortic valve of apoE$^{-/-}$ mice.

Double Staining with Antibody of the Present Invention and Antibody that Binds to the Oxidized LDL/$\beta_2$GPI Complex Double staining was performed using an antibody of the present invention and an antibody that binds to the oxidized LDL/$\beta_2$GPI complex. The explanation of each photograph is described below (FIG. 16).

FIG. 16(A): Diagram Showing the Procedure for Preparing Mouse Aortic Valve Cryosections ApoE$^{-/-}$ mice fed a high fat diet for three months or more were euthanized, and immediately laparotomized and thoracotomized to expose the heart and aorta. After an incision was made in the right auricular appendage, a needle was inserted into the left ventricle and 10 ml of cold PBS was slowly injected to remove the blood. Then, the heart was excised and cut into upper and lower halves. The aorta-side half was embedded in an embedding medium (Sakura; OCT compound) and rapidly frozen. Using a cryostat, the sample was sliced into thin sections of 7-μm thickness and placed onto glass slides. The sections were air-dried at room temperature. In the staining described below, unless otherwise specified, fixation was carried out using 1% paraformaldehyde and 50% PBS, followed by two washes with PBS for five minutes. For immunohistochemical staining, antibody 3H3 and anti-calcified globule antibodies were labeled with a fluorescent dye: Cy5.5, Alexa Fluor 488 or 555, or FITC. The fluorescent dye was combined with 1 ml of antibody (1 mg/ml) dialyzed against 0.1 M carbonate buffer at pH 8.8 (Alexa) or pH 9.3 (Cy5.5), and the combined solution was mixed at room temperature for 30 to 60 minutes. Then, non-reacted fluorescent dye was removed from labeled antibody using a Sephadex G-25 column. When Cy5.5 was used, the labeling efficiency was 3.0 to 3.8 dye molecules per one molecule of antibody 3H3.

FIG. 16(B): Hematoxylin-Eosin Staining of Mouse Aortic Valve

After fixation and washing, the tissue sections were soaked in purified water for 30 seconds, and then treated with Carrazzi's Hematoxylin solution (Muto Pure Chemicals Co.) for six minutes. After washing with water, the sections were treated with 1% Eosin Y solution (Muto Pure Chemicals Co.) for one minute. After washing with water, the sections were mounted in glycerin and photographed under a microscope.

FIG. 16(C): Oil Red Staining of Mouse Aortic Valve

Dried cryosections were fixed with 10% formalin for 30 minutes by vapor fixation, followed by treatment with purified water for 30 seconds. Then, the sections were soaked in 60% isopropyl alcohol for one minute, and treated with oil red staining solution (Sigma; saturated solution of isopropyl alcohol) at 37° C. for 15 minutes. After washing with water, the sections were treated with Carrazzi's Hematoxylin solution for five minutes. After washing with water, the sections were mounted in glycerin and photographed under a microscope.

FIG. 16(D) to (H): Fluorescent Immunostaining of Mouse Aortic Valve

Blocking solution (DakoCytomation; Protein Block Serum Free solution) was placed onto tissues encircled by pap pen. The tissues were incubated at room temperature for ten minutes. Then, the primary antibody (30 μl/sample) diluted with an antibody dilution solution (Dako) was placed onto the tissues. After 24 hours of incubation at 4° C., the tissues were washed twice with PBS for five minutes. After placing a mixed solution of fluorescently labeled secondary antibody (30 μl) and DAPI (Dojindo; 4,000 times dilution) for nuclear staining, the tissues were incubated at room temperature for one hour. Then, the tissues were washed three times with PBS for five minutes, and 20 μl of an aqueous mounting medium (Vector; Vectashield mounting medium) was placed onto the tissues. After mounting with cover glasses, their edges were sealed with manicure solution. The tissues were observed and photographed under Olympus IX71 fluorescence microscope. Fluorescence was observed using the following filters: U-MNIBA2 filter for FITC fluorescence, U-MWIG2 filter for Rhodamine fluorescence, UU-DM-CY5-2 filter for Cy5.5 fluorescence, and U-MNU2 filter DAPI fluorescence.

The specific names of the antibodies used as described in FIG. 16 are summarized below.

In FIG. 16(D), the primary antibodies used are rat anti-mouse monocyte/macrophage antibody MOMA-2 (BMA BIOMEDICALS; 1 μg/ml) and rabbit anti-alpha smooth muscle actin antibody (Abeam; 6 μg/ml); and the secondary antibodies used are Rhodamine-labeled goat anti-rat IgG antibody (Santa Cruz; 20 μg/ml) and FITC-labeled pig anti-rabbit IgG antibody (Dako; 1:20 dilution). An image obtained using U-MNIBA2 filter for FITC fluorescence was superimposed with an image obtained using U-MWIG2 filter for Rhodamine fluorescence.

In FIGS. 16(E), (F), and (G), Cy5.5-labeled antibody CL15 (100 μg/ml) and Alexa Fluor 488-labeled antibody 3H3 (25 μg/ml) were placed onto the sections. After 24 hours of incubation at 4° C., the sections were incubated with DAPI for one hour.

In FIG. 16(E), an image obtained using U-MNU2 filter for DAPI was superimposed with an image obtained using U-MWIG2 filter for Rhodamine.

In FIG. 16(F), an image obtained using U-MNU2 filter for DAPI was superimposed with an image obtained using U-MNIBA2 filter for FITC.

In FIG. 16(G), an image obtained using U-MNIBA2 filter for FITC was superimposed with an image obtained using U-MWIG2 filter for Rhodamine.

In FIG. 16(H), tissues were treated using, in combination with DAPI, a rabbit anti-osteocalcin antibody (Santa Cruz; 4 μg/ml) as the primary antibody and a Rhodamine-labeled donkey anti-rabbit IgG antibody (Santa Cruz; 4 μg/ml) as the secondary antibody. An image obtained using U-MNU2 filter for DAPI was superimposed with an image obtained using U-MWIG2 filter for Rhodamine.

As seen in FIG. 16(G), the experimental result showed that when antibody CL15 and antibody 3H3 of the present invention which recognize calcified globules were contacted to an identical pathohistological section, each of the fluorescent labels recognized different sites on the tissues. Thus, the two antibodies can be used to specify different pathological lesions on tissue sections. On the other hand, Cy5.5-labeled antibody CL15 stained sites of lipid accumulation (sites of atheroma) in the aortic valve, and Alexa Fluor 488-labeled antibody 3H3 also stained the same areas. Thus, there was some overlap in the areas stained by these two antibodies.

Furthermore, early calcified lesions detected using as an indicator the localization of osteocalcin, a bone formation related protein, were found to roughly overlap the areas recognized by the antibodies (FIG. 16(H)).

Example 12

Result of Immunoelectron Microscopic Observation of Heart after Perfusion 0.15 ml each of 250 μg/ml Cy5.5-labeled antibody 3H3 and 250 μg/ml Cy5.5-labeled antibody CL-15 were administered at the caudal vein to six-month-old apoE$^{-/-}$ mice fed a high fat diet for four months. After 24 hours, the mice were observed by in vitro near-infrared fluorescence using IVIS 200. Then, the mice were euthanized, and immediately laparotomized and thoracotomized to make an incision in the right auricular appendage. A needle was inserted into the left ventricle and 10 ml of cold PBS was slowly injected to remove blood. Then, the heart and aorta (up to the position where the aorta bifurcates into common iliac arteries) were excised, and observed for in vitro near-infrared fluorescence using IVIS 200. Following observation, the heart was embedded in an embedding medium (OCT compound) and frozen, and then the aortic valve was sliced into sections of 7-μm thickness using a cryostat. The resulting fluorescence of Cy5.5 was observed and photographed under Olympus IX71 fluorescence microscope with UU-DM-CY5-2 filter (FIGS. 17B and D). The same sections were stained with hematoxylin/eosin (FIGS. 17A and B).

As a result, fluorescence of Cy5.5-labeled antibody CL-15 was detected at the accumulative sites of foamy cells containing accumulated lipid derived from macrophages in the thickened aortic valve. The fluorescence of Cy5.5-labeled antibody 3H3 was also detected in the lipid accumulation sites in the thickened aortic valve. The observation result suggests that the labeled antibodies administered intravenously to mice for in vivo imaging indeed reached the lipid accumulation sites in the aortic valve. This supports the in vivo imaging result.

Example 13

Specificity Analysis of Anti-Calcified Globule Monoclonal Antibodies

The anti-calcified globule antibodies that are expected to be effective for visualizing arteriosclerosis in in vivo imaging were analyzed for their specificity by enzyme-linked immunosorbent assay (ELISA), and "ligand blotting" which is a combination of thin layer chromatography (TLC) and ELISA.

Antibody Purification:

Hybridomas producing IgM antibodies (CL15, CL19, and CL21) against calcified globules were grown as ascites by administering them into the peritoneal cavities of mice. The IgM antibodies were purified from the collected ascites using Mannan Binding Protein affinity column (Pierce).

ELISA:

Ethanol solutions of various lipids were aliquoted into microplates. After air-drying and blocking with BSA, the plates were treated with the anti-calcified globule antibodies.

Then, the plates were treated with an HRP-labeled anti-mouse IgM antibody. o-Phenylenediamine and hydrogen peroxide were used in the chromogenic reaction.

Ligand Blotting:

Various lipids were spotted onto a silica gel thin layer plate (Marchery-Nagel), and fractionated using a mixed solution of chloroform/methanol/28% ammonia/water (24/16/2/1). The dried plate was blocked with PBS containing 1% BSA and 1% polyvinylpyrrolidone. The plate was treated with 10 μg/ml anti-calcified globule antibody for 60 minutes and then with an HRP-labeled anti-mouse IgM antibody for 60 minutes. 4-Methoxynaphthalene and hydrogen peroxide were used in the chromogenic reaction. After each treatment, the plate was washed with TBS.

Figure 19:
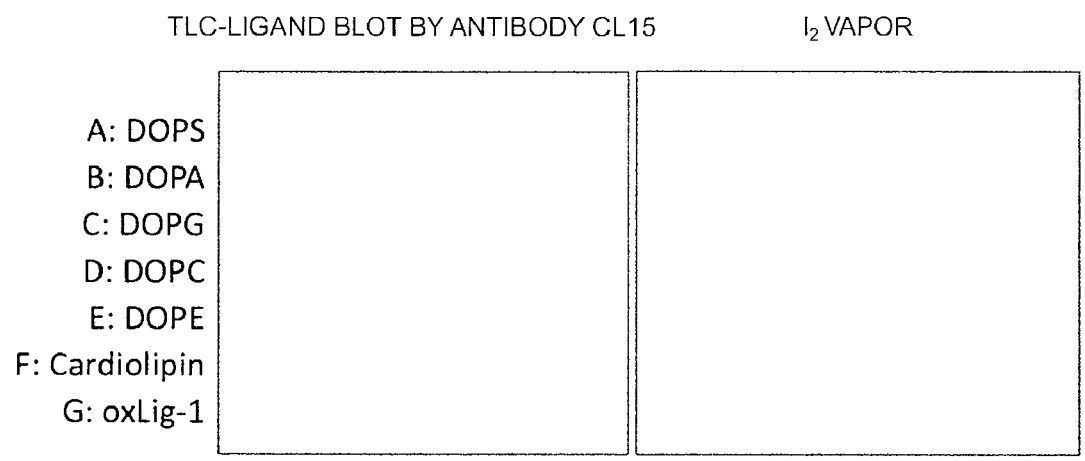

To further characterize the specificity, established monoclonal antibodies specific to calcified globules were tested for their reactivities to various lipids using ELISA and TLC-ligand blotting. Part of the result is shown in FIGS. 18 and 19. Table 2 summarizes the result. The result showed that both anti-calcified globule antibodies CL15 and CL21 bound to Ceramide-1P and had the property of binding to negatively charged phospholipids such as phosphatidylserine (PS), phosphatidic acid (PA), and cardiolipin (CL), and oxidized lipids having carboxyl group (oxLig-1).

TABLE 2

|  | CL15 | CL21 |
|---|---|---|
| DOPS | + (+) | + (+) |
| DOPA | + (+) | + (+) |
| DOPC | − (−) | − (−) |
| DOPE | − (−) | − (−) |
| CL | + (+) | + (+) |
| SM | − (−) | − (−) |
| Ceramide | − (−) | − (−) |
| Ceramide-1P | + (+) | + (+) |
| Lionleic acid | − (−) | − (−) |
| Cholesterol (Chol) | − (−) | − (−) |
| Chol-linoleate | − (−) | − (−) |
| oxLig-1 | + (+) | + (+) |

(IN PARENTHESES: ELISA RESULTS)

The formal names corresponding to the abbreviations in Table 2 are listed below.
DOPS (BBPS): 3,4-threo-dihydroxyphenylserine (phosphatidylserine)
DOPA: 3,4-dihydroxyphenylalanine (phosphatidic acid)
DOPC: 1,2-dioleoyl-sn-glycero-3-phosphatidylcholine
CL: cardiolipin
SM: sphingomyelin
Ceramide: ceramide
Ceramide-1P: ceramide-1-phosphate
Lionleic acid: linoleic acid
Chol-linoleate: cholesteryl linoleate
oxLig-1: 7-ketocholesteryl-9-carboxynonanoate [also referred to as 9-oxo-9-(7-ketochoest-5-en-3β-yloxy) nonanoic acid]

Reference Example 1

Preparation of Oxidized LDL/β$_2$GPI Complex

600 μg of human LDL (Organon Teknika Corp., Durham, N.C.) was oxidized in 2 ml of PBS containing 5 μM $CuSO_4$ at 37° C. for 12 hours. The oxidization was terminated by adding 1 mM EDTA.

0.2 mg/ml oxidized LDL described above was incubated at a final concentration of 0.2 mg/ml with human β$_2$GPI (purchased from Affinity Biologicals) at 37° C. for 16 hours to form the oxidized LDL/β$_2$GPI complex.

Reference Example 2

Immunization with Antigen

Purified protein of human oxidized LDL/β$_2$GPI complex was mixed with the same amount of complete adjuvant (SIGMA; F5881). BALB/c mice (female) were immunized through footpads with the resulting emulsion at 5 to 50 μg/head every three to seven days several times. Three to five days after the final immunization, inguinal lymph nodes were excised from the mice, and fused with cells of mouse myeloma P3U1 (P3-X63Ag8U1).

Reference Example 3

Cell Fusion, and Selection and Isolation of Monoclonal Antibody-Producing Cells

Cell fusion was carried out based on the conventional method described below. For every medium, fetal bovine serum (FBS) was used after inactivation by incubation at 56° C. for 30 minutes. P3U1 was prepared by culturing in RPMI1640-10% FBS (containing penicillin and streptomycin).

Cells from excised mouse inguinal lymph nodes were combined with P3U1 at a ratio of 10:1 to 2:1. The mixed cells were centrifuged. As a fusion enhancing agent, 50% polyethylene glycol 4000 (Merck; gas chromatography grade PEG4000, Catalog No. 9727) was added little by little to the precipitated cells while gently mixing to achieve cell fusion. Then, RPMI1640 was added little by little to the mixture with gentle mixing. The resulting mixture was centrifuged. The precipitated fused cells were appropriately diluted with HAT medium containing 15% FCS(RPMI1640, HAT-supplement (Invitrogen; 11067-030), penicillin, and streptomycin), and plated at 200 μl/well in 96-well microplates.

The fused cells were cultured in a $CO_2$ incubator (5% $CO_2$, 37° C.). When the cells were sufficiently grown as colonies, screening was carried out by sampling the culture supernatants.

In the screening, positive clones were selected by ELISA (described in Example 4) using 96-well plates coated with the human oxidized LDL/β$_2$GPI complex, which was the same as that used as the immunizing antigen. The clones were expanded using HT medium (RPMI1640, HT-supplement (Invitrogen; 21060-017), penicillin, and streptomycin) containing 15% FCS, and then cloned into single clones by the limiting dilution method. This screening which used the anti-human oxidized LDL/β$_2$GPI complex antibody as an immunogen yielded seven types of hybridoma clones including clone 3H3.

Reference Example 4

Reactivity to Human Oxidized LDL/β$_2$GPI Complex and β$_2$GPI (ELISA)

Figure 11:
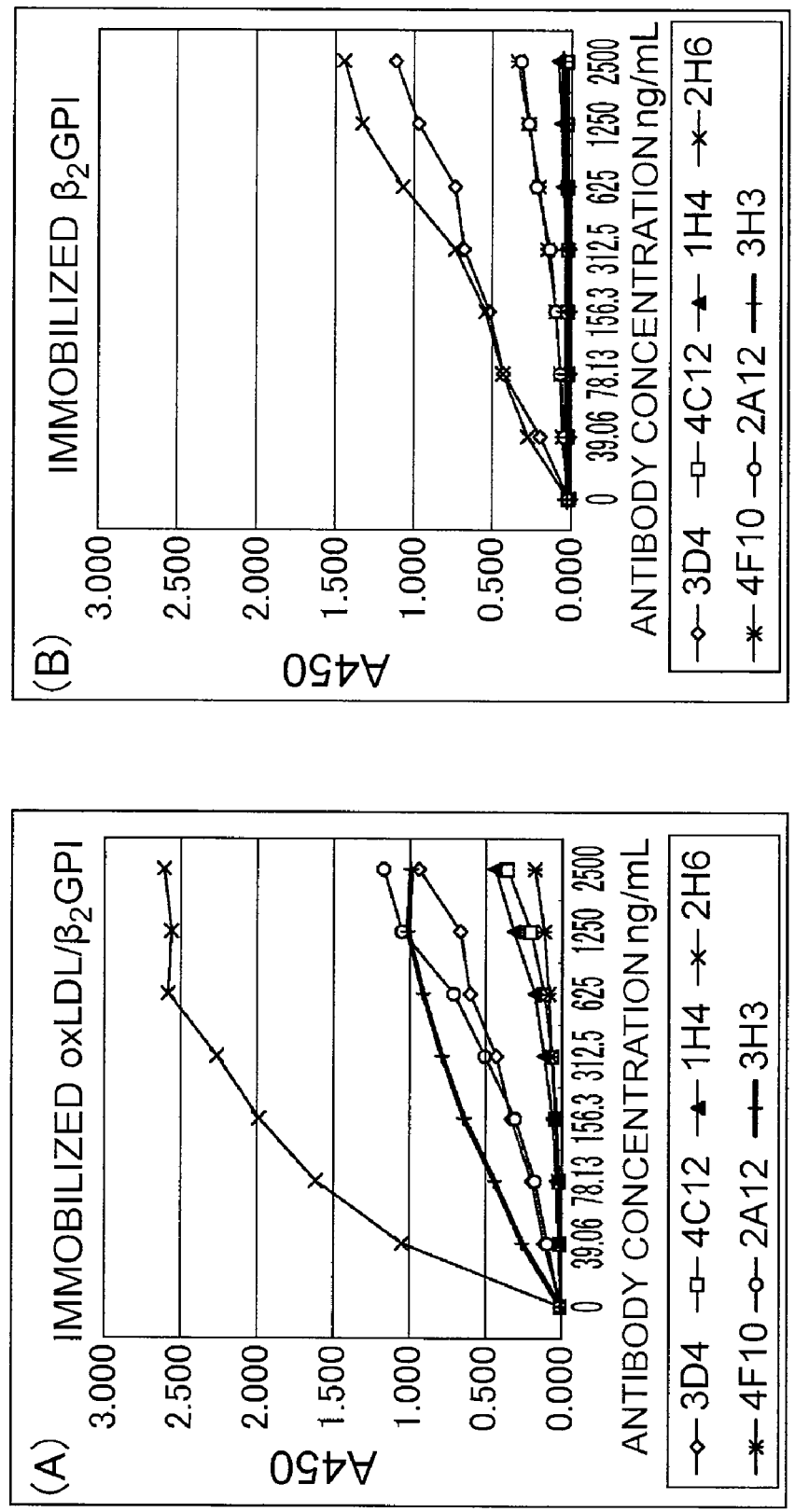
FIGS. 11A and B are diagrams showing antibody reactivites to immobolized antigen. The antibodies were monoclonal antibodies obtained by immunizing BALB/c mice with the oxidized LDL/$\beta_2$GPI complex as an antigen. The horizontal axis indicates antibody concentration, and the vertical axis indicates the absorbance.

The ELISA for detecting an anti-human oxidized LDL/β$_2$GPI complex antibody was carried out by the method described below. Specifically, 50 μl of 1 μg/ml oxidized LDL/β$_2$GPI was added to each well of microplates (Nunc; Maxisorp). The plates were incubated at 4° C. overnight to adsorb the complex, and then blocked with 1% BSA. Antibody samples were diluted using an assay buffer (1% BSA, 0.15 M NaCl/20 mM HEPES (pH 7.4)) to the antibody concentrations indicated on the horizontal axis. 50 μl of each sample was added to the wells, and the wells were incubated for 30 minutes. The solutions were discarded, and the wells were washed with 0.1% Tween 20/PBS. Then, 50 μl of 2,000-times diluted HRP-labeled anti-mouse IgG (MBL code 330) was added to each well of the plates, and incubated for 30 minutes. The solutions were discarded, and the wells were washed with 0.1% Tween 20/PBS. Then, 50 μl of substrate TMB (MOSS; TMBZ) was added, and the plates were incubated at room temperature for three minutes. After the reaction was terminated by adding 50 μl of 0.18 M sulfuric acid, detection was carried out using absorbance at 450 nm (FIG. 11).

To detect the reactivity to $β_2$GPI, ELISA was carried out by the method described below. Specifically, 50 μl of 1 μg/ml $β_2$GPI was added to each well of microplates (Nunc; Maxisorp). The plates were incubated at 4° C. overnight to adsorb $β_2$GPI, and then blocked with 1% BSA. Antibody samples were diluted using the assay buffer (1% BSA, 0.15 M NaCl/20 mM HEPES (pH 7.4)) to the antibody concentrations indicated on the horizontal axis. 50 μl of each sample was added to the wells, and incubated for 30 minutes. The solutions were discarded, and the wells were washed with 0.1% Tween 20/PBS. Then, 50 μl of 2,000-times diluted HRP-labeled anti-mouse IgG (MBL code 330) was added to each well of the plates, and incubated for 30 minutes. The solutions were discarded, and the wells were washed with 0.1% Tween 20/PBS. Then, 50 μl of substrate TMB (MOSS; TMBZ) was added, and the plates were incubated at room temperature for three minutes. After the reaction was terminated by adding 50 μl of 0.18 M sulfuric acid, detection was carried out using absorbance at 450 nm (FIG. 11).

Furthermore, various concentrations of $β_2$GPI (up to 50 μg/ml) were prepared and added at 50 μl/well to microplates (Nunc; Maxisorp). The plates were incubated at 4° C. overnight to adsorb $β_2$GPI. Then, the antibody reactivity was tested in the same manner (data not shown).

The result showed that the reactivity towards the immobilized oxidized LDL/$β_2$GPI complex was: 2H6>3H3, 2A12, 3D4>4C12, 1H4. Alternatively, the reactivity towards the immobilized $β_2$GPI was: 2H6, 3D4>2A12, 4F10. 3H3 and 4C12 were not reactive to the immobilized $β_2$GPI (FIG. 11).

However, when the coating concentration in microtiter plates was increased, 3H3 also exhibited reactivity (data not shown).

Next, as a method for assessing antibody reactivity, inhibition test using a free antigen was carried out to evaluate the specificity of each antibody.

Reference Example 5

Competitive Reactivity to Free $β_2$GPI or Oxidized LDL/$β_2$GPI Complex in Solution (ELISA)

In the reactivity assay (ELISA) for immobilized human oxidized LDL/$β_2$GPI complex and $β_2$GPI, an inhibitory reaction to immobilized antigen was carried out by having oxidized LDL/$β_2$GPI complex or $β_2$GPI together when the antibodies were added in the reaction.

Specifically, 50 μl of 1 μg/ml $β_2$GPI was added to each well of microplates (Nunc; Maxisorp). The plates were incubated at 4° C. overnight to adsorb $β_2$GPI, and then blocked with 1% BSA. Antibody samples were diluted to appropriate concentrations using the assay buffer (1% BSA, 0.15 M NaCl/20 mM HEPES (pH 7.4)), and samples of oxidized LDL/$β_2$GPI complex or $β_2$GPI, which serves as a competitive antigen, were diluted to the antigen concentrations indicated on the horizontal axis. 25 μl each of the diluted antibody sample and antigen sample were added to the wells, and the wells were incubated for 30 minutes. The solutions were discarded, and the wells were washed with 0.1% Tween 20/PBS. Then, 50 of 2,000-times diluted HRP-labeled anti-mouse IgG (MBL code 330) was added to each well of the plates, and the plates were incubated for 30 minutes. The solutions were discarded, and the wells were washed with 0.1% Tween 20/PBS. Then, 50 μl of substrate TMB (MOSS; TMBZ) was added, and the plates were incubated at room temperature for three minutes. After the reaction was terminated by adding 50 μl of 0.18 M sulfuric acid, detection was carried out using absorbance at 450 nm.

Figure 12:
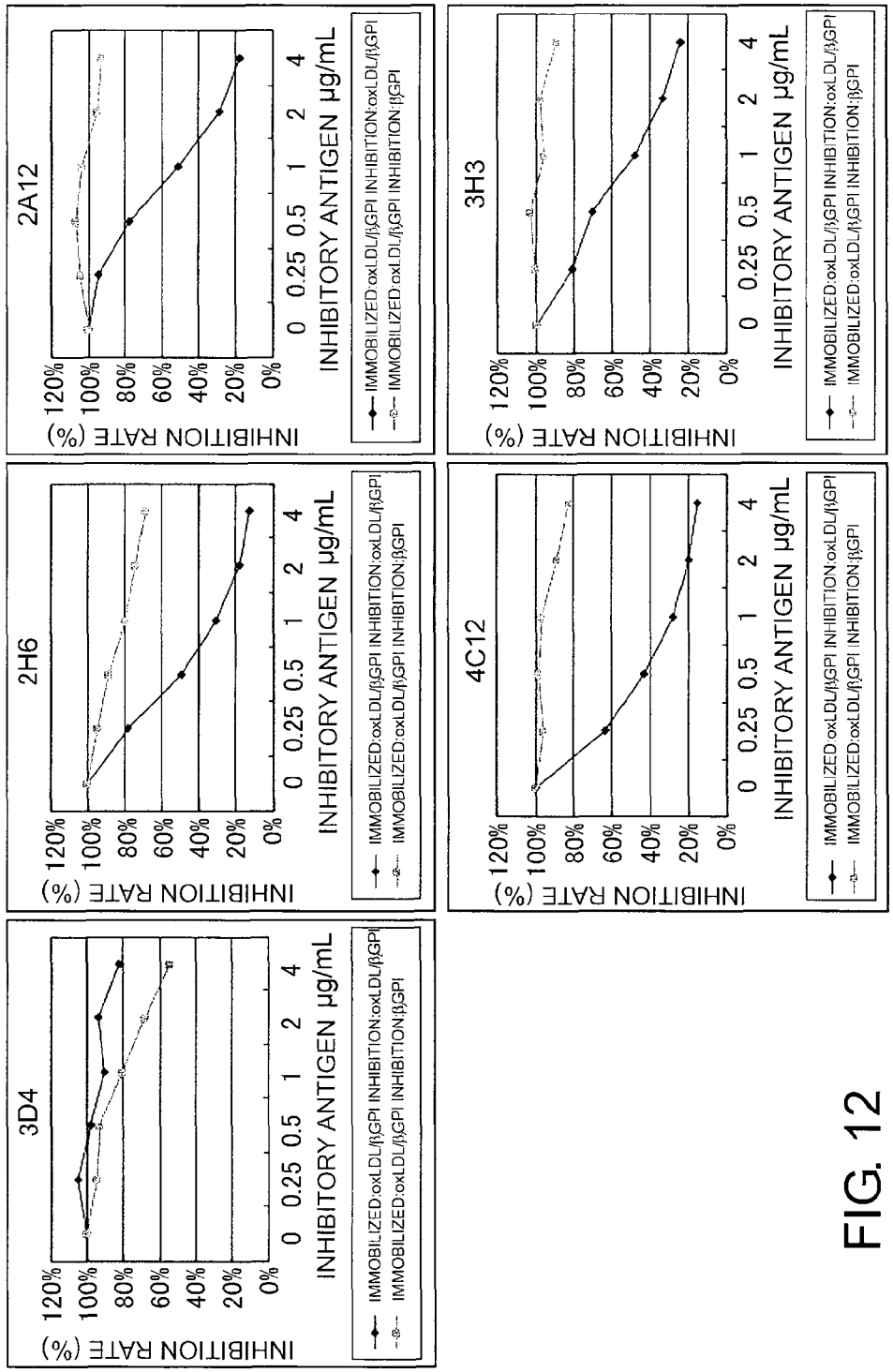
FIG. 12 is graphs showing a test of competitive inhibition by antigen. The horizontal axis indicates antigen concentration in a liquid, and the vertical axis indicates the percent inhibition (%) determined when taking the absorbance in the absence of inhibitory antigen as 100%. 3H3 and 4C12 are antibodies that recognize $\beta_2$GPI bound to oxidized LDL. These antibodies do not recognize free $\beta_2$GPI. 2H6, 3D4, and 2A12 are antibodies reactive to free $\beta_2$GPI.

The result showed that when the coexisting oxidized LDL/$β_2$GPI complex was the free antigen in ELISA, the binding of 3H3, 4C12, and 2A12 to immobilized oxidized LDL/$β_2$GPI was markedly inhibited, while $β_2$GPI did not inhibit the binding. On the other hand, the binding of 2H6 was inhibited when the free antigen was the oxidized LDL/$β_2$GPI complex, and the mixing with $β_2$GPI also inhibited the binding to some extent. As for 3D4, stronger inhibition was observed with $β_2$GPI than with oxidized LDL/$β_2$GPI complex as free antigen (FIG. 12).

Reference Example 6

Immunohistochemical Staining of Arteriosclerotic Plaques with Antibodies

ApoE$^{-/-}$ mice and LDLR$^{-/-}$ mice (obtained from Jackson Lab, and maintained in the animal experiment facility at Okayama University) were fed a common diet (Oriental Yeast NMF) up to eight weeks old, and then fed a high fat diet (common diet additionally containing 1% cholesterol, 1% cholic acid, and 15% salt-free butter) for four to six months. As a result, arteriosclerotic plaques developed, and thus thickening and atheroma were observed in the thoracic or abdominal aorta. Then, these eight-month-old mice were sacrificed. Cryosections of the thoracic aorta, and aortic root and valves were prepared from the mice, and observed as samples.

The prepared cryosections were fixed with paraformaldehyde and then used in the experiment of fluorescent antibody immunostaining.

Immunohistochemical Staining

Figure 13:
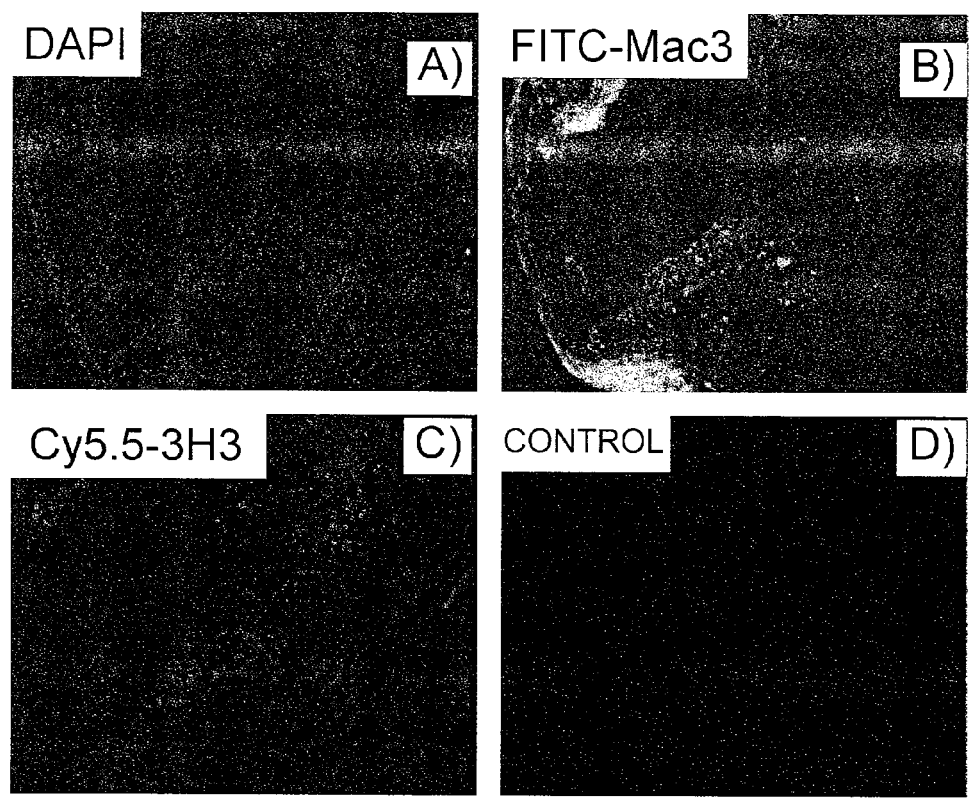
FIG. 13 is photographs showing fluorescent immunostaining of the aortic valve in arteriosclerosis-prone model mice (apoE$^{-/-}$ fed a high fat diet). (A) DAPI, nuclear stain; (B) Mac3, macrophage-specific antibody; (C), antibody 3H3; (D), control. When used in fluorescent immunostaining of C57BL6 mice fed a normal diet, Mac3 stained atheroma formed via accumulation of foamy macrophages. 3H3 stained the same areas.

The result showed that when used in fluorescent immunostaining of C57BL6 mice fed a normal diet, both antibodies 3H3 and Mac3 stained atheroma resulting from accumulation of foamy macrophages. 3H3 stained the same areas (FIG. 13).

Figure 14:
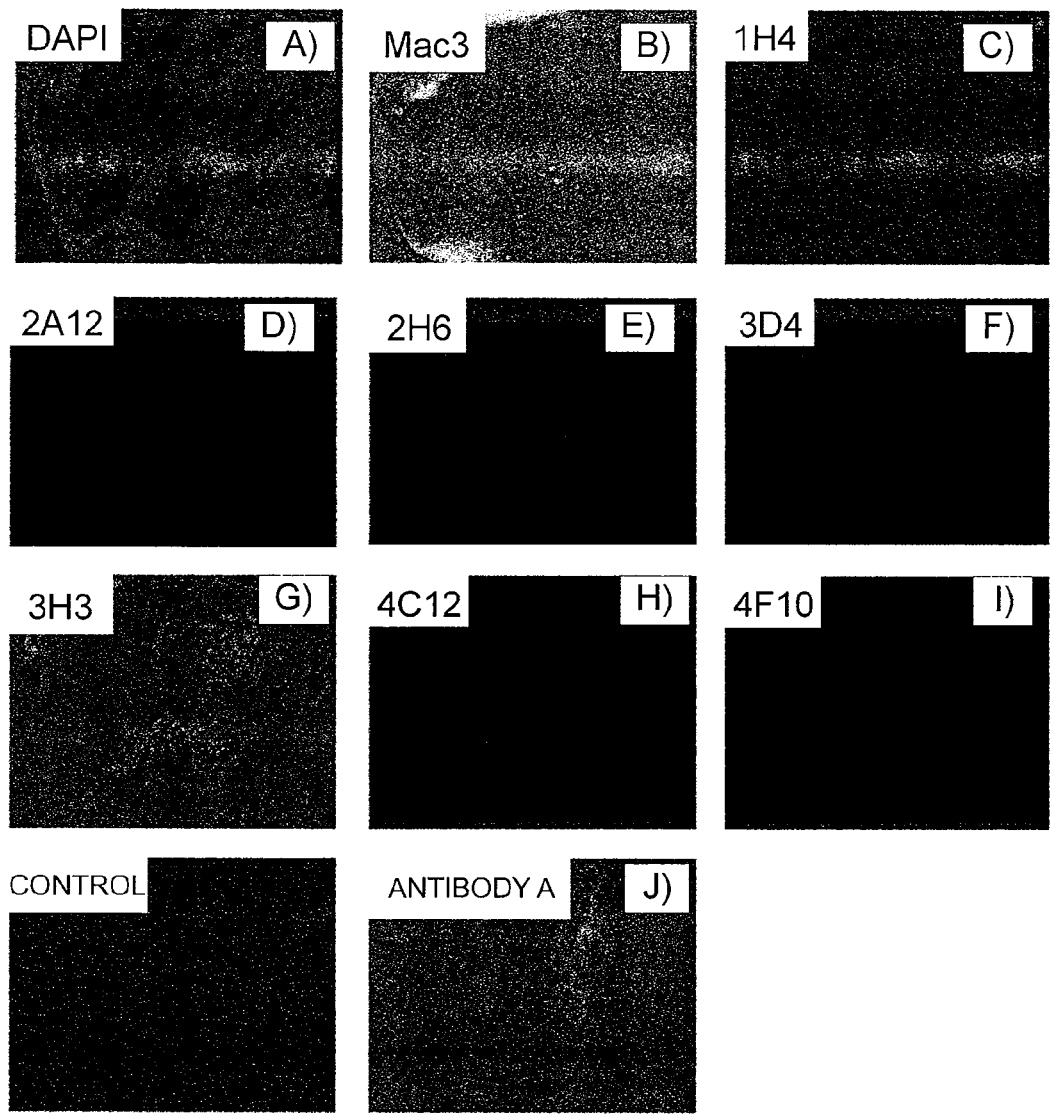
FIG. 14A to J are photographs showing fluorescent immunostaining of the aortic valve in arteriosclerosis-prone mice (apoE$^{-/-}$ fed a high fat diet). The photographs show results of fluorescent immunostaining using other antibodies against the oxidized LDL/$\beta_2$GPI complex. Antibodies positive for atheroma in the staining were only antibodies 3H3 and A.

Fluorescent immunostaining of the aortic valve in arteriosclerosis-prone model mice (apoE$^{-/-}$ fed a high fat diet) was compared to the result obtained using different antibodies that recognize the oxidized LDL/$β_2$GPI complex. Antibodies positive for atheroma in the staining were only antibodies 3H3 and A (FIG. 14).

Thus, the present invention enables arteriosclerotic plaque-specific immunostaining using various atheroma-specific monoclonal antibodies labeled with Cy5.5, Alexa, or the like.

Reference Example 7

Imaging

In Vivo Imaging:

Imaging was performed using IVIS™ Imaging System, IVIS 200, from Xenogen (excitation, 640 nm; emission, 720 nm).

Experiment 1: Cy5.5-labeled monoclonal antibody (0.25 mg/ml) was administered at 0.15 ml/head via the caudal vein to apoE$^{-/-}$ mice fed a high fat diet, which were prepared by the same method as described in Example 6. The following three were administered: physiological saline (PBS; control), Cy5.5-labeled antibody A, and Cy5.5-labeled antibody 3H3. Twenty four hours after administration, the mice were photographed alive for the full-body image after removing their thoracic skin (FIG. 21).

Experiment 2: Then, the heart intact with thoracic aorta was excised and photographed (FIG. 21). The aortic root was intensely stained by 3H3 administration. Antibody A also stained to some extent; however, the fluorescence intensity was weaker as compared to 3H3. There was no stain with 2A12.

The fluorescence intensity was determined per unit area of the aortic root. The fluorescence of PBS-administered control mouse was taken as 1.0. When 3H3 was administered, fluorescence was three times stronger than the control. There was no significant change in the fluorescence intensity when other antibodies were administered (FIG. 24).

The specificity assessment of the antibodies described above is summarized in Table 3.

TABLE 3

ANTIBODIES SPECIFIC TO OXDIZED LDL/β2GPI COMPLEX

| | BINDING TO IMMOBILIZED ANTIGEN | | COMPETITIVE INHIBITION (IMMOBILIZED OXIDIZED LDL/(β2GPI) | | |
|---|---|---|---|---|---|
| | β2GPI | OXIDIZED LDL/β2GPI | OXIDIZED β2GPI | OXIDIZED LDL/β2GPI | IMMUNO-STAINING |
| 1H4 | − | + | ND | ND | − |
| 2A12 | + | ++ | − | ++ | − |
| 2H6 | ++ | +++ | ++ | ++ | − |
| 3D4 | ++ | ++ | ++ | − | − |
| 3H3 | − | ++ | − | ++ | +++ |
| 4C12 | − | + | − | ++ | − |
| 4F10 | + | − | ND | ND | − |

β$_2$GPI was added as an inhibitory, competitive antigen to the immobilized oxidized LDL/β$_2$GPI complex or immobilized β$_2$GPI, and the resulting inhibition was assessed by ELISA. The result is as follows: in the case of immobilized oxidized LDL/β$_2$GPI complex, 3D4>2H6>4C12>3H3; and in the case of immobilized β$_2$GPI, 2H6>3D4 (4C12 and 3H3 bound only weakly to immobilized β$_2$GPI). 3H3 was highly specific to the free (non-denatured) form of oxidized LDL/β$_2$GPI complex in a solution.

Reference Example 8

Analysis of Variable Region Gene of Mouse Monoclonal Antibodies that Recognize Oxidized LDL/β$_2$GPI Complex Four monoclonal antibody clones analyzed were: 3H3, 4C12, 2H6, and 3D4.

The antibody subclasses of the four clones are as follows: 3H3 and 4C12 are IgG2b; and 2H6 and 3D4 are IgG1.

Analysis of L-Chain Variable Region Gene

Hybridomas which produce four types of monoclonal antibodies (3H3, 4C12, 2116, and 3D4) were each cultured in RPMI1640 supplemented with 10% FCS. mRNAs were obtained from the hybridomas using the QuickPrep micro mRNA purification kit (Amersham Biosciences; code 27-9255-01). The mRNAs were converted into cDNAs using the First-Strand cDNA Synthesis kit (Amersham Biosciences; code 27-9261-01). Gene amplification was achieved by PCR using the cDNAs as a template. PCR was carried out using the 11 types of primer combinations listed below. The sequences of primers MKV1 to MKV11 were designed by analyzing the signal sequences of numerous various monoclonal antibodies. Thus, the 11 types of primer sequences can cover the L chain signal of almost every monoclonal antibody. An L-chain variable region of interest is amplified by using at least a single PCR pattern selected from 11 PCR patterns using combinations of the 11 types of MKV primers with primer MKC which corresponds to the sequence of a mouse L-chain constant region.

The PCR conditions are shown below.

| | |
|---|---|
| cDNA derived from mouse hybridoma | 4 μl |
| 2.5 mM dNTPs | 4 μl |
| one of the 11 types of primers MKV1 to MKV11 (20 μM) | 2.5 μl |
| MKC primer (20 μM) | 2.5 μl |
| DMSO | 2.5 μl |
| ×10 pfu polymerase buffer | 5 μl |
| pfu polymerase | 1 μl |
| sterile water | 28.5 μl |
| Total | 50 μl |

94° C. for 2 min
94° C. for 1 min, 55° C. for 2 min, 72° C. for 2 min (30 cycles)
72° C. for 4 min
4° C., no time restriction The DNA sequences of primers are shown below.

```
                                        (SEQ ID NO: 63)
MKV1 primer:    ATGAAGTTGCCTGTTAGGCTGTTGGTGCTG (SEQ ID NO: 64)
MKV2 primer:    ATGGAGWCAGACACACTCCTGYTATGGGTG (SEQ ID NO: 65)
MKV3 primer:    ATGAGTGTGCTCACTCAGGTCCTGGSGTTG (SEQ ID NO: 66)
MKV4 primer:    ATGAGGRCCCCTGCTCAGWTTYTTGGMWTCTTG (SEQ ID NO: 67)
MKV5 primer:    ATGGATTTWCAGGTGCAGATTWTCAGCTTC (SEQ ID NO: 68)
MKV6 primer:    ATGAGGTKCYYTGYTSAGYTYCTGRGG (SEQ ID NO: 69)
MKV7 primer:    ATGGGCWTCAAGATGGAGTCACAKWYYCWGG (SEQ ID NO: 70)
MKV8 primer:    ATGTGGGGAYCTKTTTYCMMTTTTTCAATTG (SEQ ID NO: 71)
MKV9 primer:    ATGGTRTCCWCASCTCAGTTCCTTG (SEQ ID NO: 72)
MKV10 primer:   ATGTATATATGTTTGTTGTCTATTTCT (SEQ ID NO: 73)
MKV11 primer:   ATGGAAGCCCCAGCTCAGCTTCTCTTCC (SEQ ID NO: 74)
MKC primer:     ACTGGATGGTGGGAAGATGG
(M = A or C;  R = A or G;  W = A or T;
 S = C or G;  Y = C or T;  K = G or T)
```

Combinations of PCR primers responsible for the amplification of each L-chain variable region by PCR are as follows:

3H3: MKV7-MKC
4C12: MKV7-MKC
2H6: MKV5-MKC
3D4: MKV4-MKC

The L-chain variable region genes amplified by PCR were inserted into pCR2.1 vector (Invitrogen).

The DNA nucleotide sequence of PCR2.1 vector inserted with an L-chain variable region gene was determined using a DNA sequencer (Applied Biosystems; 3130 Genetic Analyzer).

Analysis of H-Chain Variable Region Gene

Hybridomas which produce four types of monoclonal antibodies (3H3, 4C12, 2H6, and 3D4) were each cultured in RPMI1640 supplemented with 10% FCS. mRNAs were obtained from the hybridomas using the QuickPrep micro mRNA purification kit (Amersham Biosciences; code 27-9255-01). The mRNAs were converted into cDNAs using the First-Strand cDNA Synthesis kit (Amersham Biosciences; code 27-9261-01). Amplification of H-chain variable region genes was achieved by PCR using the cDNAs as a template. PCR was carried out using the 12 types of primer combination listed below. The sequences of primers MHV1 to MHV12 were designed by analyzing the signal sequences of numerous various monoclonal antibodies. Thus, the 12 types of primer sequences can cover the H chain signal of almost every monoclonal antibody. An H-chain variable region of interest is amplified by using at least a single PCR pattern selected from 12 PCR patterns using combinations of the 12 types of MHV primers with primer MHCG2b or MHCG1 which corresponds to the sequence of a mouse H-chain constant region. Primer MHCG2b corresponds to the sequence of an H-chain constant region of mouse IgG2b, while primer MHCG1 corresponds to the sequence of an H-chain constant region of mouse IgG1. Thus, primer MHCG2b was used in the PCR amplification of clones 3H3 and 4C12, which are of the IgG2b subclass. Primer MHCG1 was used in the PCR amplification of clones 2H6 and 3D4, which are of the IgG1 subclass.

The PCR conditions are shown below.

| | |
|---|---|
| cDNA derived from mouse hybridoma | 4 μl |
| 2.5 mM dNTPs | 4 μl |
| one of the 12 types of primers MHV1 to MHV12 (20 μM) | 2.5 μl |
| MHCG2b or MHCG1 primer (20 μM) | 2.5 μl |
| DMSO | 2.5 μl |
| ×10 pfu polymerase buffer | 5 μl |
| pfu polymerase | 1 μl |
| sterile water | 28.5 μl |
| Total | 50 μl |

94° C. for 2 min
94° C. for 1 min, 55° C. for 2 min, and 72° C. for 2 min (30 cycles)
72° C. for 4 min
4° C., no time restriction The DNA sequences of primers are shown below.

```
                        (SEQ ID NO: 75)
MHV1 primer:   ATGAAATGCAGCTGGGGCATSTTCTTC (SEQ ID NO: 76)
MHV2 primer:   ATGGGATGGAGCTRTATCATSYTCTT (SEQ ID NO: 77)
MHV3 primer:   ATGAAGWTGTGGTTAAACTGGGTTTTT (SEQ ID NO: 78)
MHV4 primer:   ATGRACTTTGGGYTCAGCTTGRTTT (SEQ ID NO: 79)
MHV5 primer:   ATGGACTCCAGGCTCAATTTAGTTTTCCTT (SEQ ID NO: 80)
MHV6 primer:   ATGGCTGTCYTRGSGCTRCTCTTCTGC (SEQ ID NO: 81)
MHV7 primer:   ATGGRATGGAGCKGGRTCTTTMTCTT (SEQ ID NO: 82)
MHV8 primer:   ATGAGAGTGCTGATTCTTTTGTG (SEQ ID NO: 83)
MHV9 primer:   ATGGMTTGGGTGTGGAMCTTGCTATTCCTG (SEQ ID NO: 84)
MHV10 primer:  ATGGGCAGACTTACATTCTCATTCCTG (SEQ ID NO: 85)
MHV11 primer:  ATGGATTTTGGGCTGATTTTTTTATTG (SEQ ID NO: 86)
MHV12 primer:  ATGATGGTGTTAAGTCTTCTGTACCTG (SEQ ID NO: 87)
MHCG2b primer: CAGTGGATAGACTGATGGGGG (SEQ ID NO: 88)
MHCG1 primer:  CAGTGGATAGACAGATGGGGG
(M = A or C; R = A or G; W = A or T;
 S = C or G; Y = C or T; K = G or T)
```

Combinations of PCR primers responsible for the amplification of each H-chain variable region by PCR are as follows:
3H3: MHV4-MHCG2b
4C12: MKV4-MHCG2b
2H6: MHV4-MHCG1
3D4: MHV1-MHCG1

The H-chain variable region genes amplified by PCR were inserted into the pCR2.1 vector (Invitrogen).

The DNA nucleotide sequence of the PCR2.1 vector inserted with an H-chain variable region gene was determined using a DNA sequencer (Applied Biosystems; 3130 Genetic Analyzer).

Thus, the amino acid sequence of 3H3 and its CDRs were revealed, and can be used in the present invention (FIG. 25).

The amino acid and nucleotide sequences of antibody 3H3 are described below.

<Antibody 3H3>

SEQ ID NO: 53, the amino acid sequence of heavy-chain variable region

SEQ ID NO: 54, the amino acid sequence of heavy chain CDR1

SEQ ID NO: 55, the amino acid sequence of heavy chain CDR2

SEQ ID NO: 56, the amino acid sequence of heavy chain CDR3

SEQ ID NO: 57, the nucleotide sequence of heavy-chain variable region

SEQ ID NO: 58, the amino acid sequence of light-chain variable region

SEQ ID NO: 59, the amino acid sequence of light chain CDR1

SEQ ID NO: 60, the amino acid sequence of light chain CDR2

SEQ ID NO: 61, the amino acid sequence of light chain CDR3

SEQ ID NO: 62, the nucleotide sequence of light-chain variable region

Reference Example 9

Assessment of Image Analysis Using IVIS 200 and Three-Dimensional CT

Experiments were carried out to generate three-dimensional (localization) images of arteriosclerotic plaques by integrating computed tomography (CT) images.

In Vivo Fluorescence Imaging:

Fluorescence imaging was carried out using IVIS 200 Imaging System (Xenogen) (for Cy5.5, [excitation, 640 nm; emission, 720 nm]; for Alexa Fluor 750, [excitation, 745 nm; emission, 800 nm]). 0.25 mg/ml Cy5.5-labeled antibody 3H3 (IgG) or 1.0 to 1.5 mg/ml Alexa Fluor 750-labeled antibody 3H3 was administered at 0.15 ml/head via the caudal vein to ApoE$^{-/-}$ mice fed a high fat diet, and after two to 24 hours under inhalation anesthesia, in vivo fluorescence was observed and photographed using IVIS 200. The ApoE$^{-/-}$ mice were observed after shaving because their black hair absorbs fluorescence. First, the fluorescence was observed with reflected light, and then with transmitted light. Three-dimensional (3D) images of mice were generated and integrated with the light source information (FIG. 23A: a three-dimensional image by IVIS before integration). In the figure, red dots correspond to fluorescent signals from labels linked to 3H3. The denser red dots mean stronger fluorescence intensity, showing the localization of the imaging agent.

Ex Vivo Imaging:

After 3D CT analysis, the mice were euthanized, and the hearts were perfused with 10 ml of PBS. The hearts and aortae were excised and their reflection fluorescence images were obtained using IVIS 200.

CT Imaging:

CT imaging was performed using eXplore Locus CT System (GE Healthcare). Under inhalation anesthesia, the same mice used in the IVIS 200 imaging were irradiated with X ray to obtain CT images.

Integration of Fluorescence and CT Images:

Using general-purpose 3D visualization software (Amira; Mercury Computer Systems), fluorescent images detected by IVIS 200 were integrated with images obtained using CT (FIG. 23B: a three-dimensional CT image after integration).

The procedure is shown schematically (FIG. 22).

(A) IVIS 200 fluorescence imaging using a specific antibody (reflection).

(B) IVIS 200 fluorescence image obtained using a specific antibody (transmitted light; left) and CT image (middle) before integration, and integrated image (right). In the fluorescence image (transmitted light; left), as the red dots become denser, the fluorescence intensity becomes stronger, suggesting that the imaging agent is localized and accumulated at the position (site that exhibits stronger binding reactivity to 3H3).

(C) Image resulting from integration of IVIS fluorescent signal and three-dimensional CT image: the photograph shows a three-dimensional image generated as animation in a computer-generated virtual space (three-dimensional graphic animation). The sites labeled were observed from multiple angles.

The visible light is absorbed by the body while the light of near-infrared wavelengths is hardly absorbed by the body. Thus, near-infrared fluorescent labels are suitable for in vivo imaging. In this experiment, antibodies labeled with Cy5.5 or Alexa Fluor 750 were administered to mice via the caudal vein, and the resulting fluorescence was monitored with IVIS 200 to assess the measurement conditions for the reflection and transmission fluorescence. When ApoE$^{-/-}$ mice with arteriosclerosis were observed by in vivo reflection fluorescence imaging using a Cy5.5-labeled antibody, intense signals were found in the aortic valve and thoracic aorta. Furthermore, by ex vivo imaging and ex vivo fluorescence microscopy, the fluorescently labeled antibody administered into the vein was demonstrated to be localized in arteriosclerotic plaques. However, when a Cy5.5-labeled antibody was used, the signal of transmission fluorescence was weak and thus it was difficult to identify the site of fluorescence in the three-dimensional (3D) images. By contrast, when an Alexa Fluor 750-labeled antibody was used, specific intense signals were observed two hours after intravenous administration in both reflection and transmission fluorescence images. In the generated three-dimensional image, intense fluorescent signals were recognized in the chest (FIGS. 22A and B, left panels). Then, the same mice were photographed by CT. The image (FIG. 22B, middle panel) resulting from extraction of bones and lungs from CT image was integrated with an IVIS 200 fluorescent image by Amira. The resulting integrated 3D image (FIG. 22B, right panel) showed that the presence of fluorescent signals in and around the heart. In the figure, the denser red dots suggest stronger fluorescence intensity, showing the localization of the imaging agent. CT image (middle panel) and 3D-CT integrated image (FIG. 22B, right panel) are shown. A three-dimensional image was generated as animation in a computer-generated virtual space (three-dimensional graphic animation). The sites labeled were observed from multiple angles (FIG. 22C).

The experimental result described above showed that when ApoE$^{-/-}$ mice with arteriosclerosis were observed by in vivo reflection fluorescence imaging using fluorescently labeled antibody 3H3, intense signals were found in the aortic valve and thoracic aorta. Furthermore, by ex vivo imaging and ex vivo fluorescence microscopy, the fluorescently labeled antibody administered into the vein was demonstrated to be localized in arteriosclerotic plaques.

The experiment described above demonstrated not only that arteriosclerosis in mice could be visualized by using a near-infrared fluorescent substance (Cy5.5 or Alexa 750)-labeled antibody, but also that the images could be integrated with three-dimensional CT images. Furthermore, it has been demonstrated that such antibodies enable detection of human arteriosclerotic plaques. The experimental results described herein will lead to clinically applicable technologies for diagnostic imaging. In addition, the mouse imaging techniques are already practicable as a screening system for drug discovery.

INDUSTRIAL APPLICABILITY

The sites (locations) of arteriosclerosis cannot be identified by conventional tests for arteriosclerosis. In contrast, the present invention provides non-invasive diagnostic methods that allow visual identification of the site and size of arteriosclerotic plaques (in particular, calcified lesions).

A screening system for therapeutic agents to treat arteriosclerosis can be constructed by using arteriosclerosis-prone model mice (apoE-deficient mice which maintain high plasma cholesterol level and spontaneously develop an atherosclerosis-like condition) and antibodies for the imaging.

Furthermore, an imaging system for clinical diagnosis can be constructed by converting the antibodies into humanized antibodies. This allows monitoring of human arteriosclerosis (in particular, calcified lesions), which progresses insidiously, asymptomatically, and chronically. It has been reported that the coronary artery calcification occurs at early stages of arteriosclerosis, and the degree of calcification correlates with the degree of stenosis. In addition, the coronary artery calcification score reflects the severity of coronary lesion in diabetes patients. Thus, the present invention is expected to benefit strategies for preventing or treating lifestyle-related diseases.

The invention claimed is:
1. An isolated antibody which is reactive to a calcified globule (NLO) derived from renal or urinary calculi and has the activity of binding to an atherosclerotic plaque, which is the antibody of any one of (e), (j), or (o):
  (a) an antibody comprising a heavy chain that comprises CDR1 having the amino acid sequence of SEQ ID NO: 1, CDR2 having the amino acid sequence of SEQ ID NO: 2, and CDR3 having the amino acid sequence of SEQ ID NO: 3;
  (b) an antibody comprising a heavy chain that comprises a heavy-chain variable region having the amino acid sequence of SEQ ID NO: 4;
  (c) an antibody comprising a light chain that comprises CDR1 having the amino acid sequence of SEQ ID NO: 6, CDR2 having the amino acid sequence of SEQ ID NO: 7, and CDR3 having the amino acid sequence of SEQ ID NO: 8;
  (d) an antibody comprising a light chain that comprises a light-chain variable region having the amino acid sequence of SEQ ID NO: 9;
  (e) an antibody that comprises a pair of the heavy chain of (a) or (b) and the light chain of (c) or (d);
  (f) an antibody comprising a heavy chain that comprises CDR1 having the amino acid sequence of SEQ ID NO: 11, CDR2 having the amino acid sequence of SEQ ID NO: 12, and CDR3 having the amino acid sequence of SEQ ID NO: 13;
  (g) an antibody comprising a heavy chain that comprises a heavy-chain variable region having the amino acid sequence of SEQ ID NO: 14;
  (h) an antibody comprising a light chain that comprises CDR1 having the amino acid sequence of SEQ ID NO: 16, CDR2 having the amino acid sequence of SEQ ID NO: 17, and CDR3 having the amino acid sequence of SEQ ID NO: 18;
  (i) an antibody comprising a light chain that comprises a light-chain variable region having the amino acid sequence of SEQ ID NO: 19;
  (j) an antibody that comprises a pair of the heavy chain of (f) or (g) and the light chain of (h) or (i);
  (k) an antibody comprising a heavy chain that comprises CDR1 having the amino acid sequence of SEQ ID NO: 21, CDR2 having the amino acid sequence of SEQ ID NO: 22, and CDR3 having the amino acid sequence of SEQ ID NO: 23;
  (l) an antibody comprising a heavy chain that comprises a heavy-chain variable region having the amino acid sequence of SEQ ID NO: 24;
  (m) an antibody comprising a light chain that comprises CDR1 having the amino acid sequence of SEQ ID NO: 26, CDR2 having the amino acid sequence of SEQ ID NO: 27, and CDR3 having the amino acid sequence of SEQ ID NO: 28;
  (n) an antibody comprising a light chain that comprises a light-chain variable region having the amino acid sequence of SEQ ID NO: 29;
  (o) an antibody that comprises a pair of the heavy chain of (k) or (l) and the light chain of (m) or (n).
2. The isolated antibody of claim 1, which is a humanized or chimeric antibody.
3. An imaging agent for visualizing a calcified arteriosclerotic site, which comprises the isolated antibody of claim 1.
4. An imaging kit for visualizing a calcified arteriosclerotic site, which comprises the isolated antibody of claim 1.
5. An agent for inhibiting the growth of a calcified globule, which comprises an isolated antibody of claim 1.
6. A therapeutic agent for arteriosclerosis, which comprises an isolated antibody of claim 1.
7. A method of screening for a candidate compound for a therapeutic agent for arteriosclerosis, which comprises the steps of:
  (a) administering a candidate compound to an arteriosclerosis model nonhuman animal administered with the isolated antibody of claim 1;
  (b) carrying out imaging of an arteriosclerotic plaque in an arteriosclerosis model nonhuman animal administered with the candidate compound and in an arteriosclerosis model nonhuman animal not administered with the candidate compound;
  (c) comparing the size or location of an arteriosclerotic plaque between the arteriosclerosis model nonhuman animal administered with the candidate compound and the arteriosclerosis model nonhuman animal not administered with the candidate compound; and
  (d) selecting a candidate compound that reduces or eliminates an arteriosclerotic plaque in the arteriosclerosis model nonhuman animal administered with the candidate compound as compared to the arteriosclerosis model nonhuman animal not administered with the candidate compound.
8. A kit for immunologically detecting a calcification site and an arteriosclerosis site in an atherosclerotic plaque, which comprises the isolated antibody of claim 1 and an antibody that binds to a complex of oxidized LDL and $\beta_2$-glycoprotein I (oxidized LDL/$\beta_2$GPI complex).
9. An immunological method, which comprises the steps of:
  (a) contacting an isolated arteriosclerotic plaque with the isolated antibody of claim 1 and an antibody that binds to an oxidized LDL/$\beta_2$GPI complex; and
  (b) detecting a calcification site and an arteriosclerosis site in the arteriosclerotic plaque.
10. A method for detecting a pathological condition due to arteriosclerosis, which comprises the steps of:
  (a) contacting an arteriosclerotic plaque with the isolated antibody of claim 1 or 2 and an antibody that binds to an oxidized LDL/$\beta_2$GPI complex;
  (b) detecting a calcification site and an atheroma of arteriosclerosis, or early lesion thereof in the arteriosclerotic plaque; and
  (c) assessing whether an arteriosclerotic plaque is detected by the isolated antibody of claim 1 or 2 or an antibody that binds to an oxidized LDL/$\beta_2$GPI complex.
11. An imaging method for visualizing an arteriosclerotic calcification site comprising contacting an arteriosclerotic calcification site with the isolated antibody of claim 1 and detecting an arteriosclerosis calcification site.
12. The isolated antibody of claim 1, which additionally has the activity of binding to at least one selected from the group consisting of LDL oxidatively modified by copper sulfate (oxidized LDL), phosphatidylserine, cardiolipin, and 7-ketocholesteryl-9-carboxynonanoate (9-oxo-9-(7-ketochoest-5-en-3β-yloxy) nonanoic acid).
13. The isolated antibody of claim 1, which additionally has the activity of binding to oxidized LDL, phosphatidylserine, cardiolipin, and 7-ketocholesteryl-9-carboxynonanoate.
14. The isolated antibody of claim 1, which additionally has the activity of binding to cardiolipin and 7-ketocholesteryl-9-carboxynonanoate.
15. The isolated antibody of claim 1, which is reactive to a calcified globule in ELISA but is not reactive to at least one selected from the group consisting of LDL oxidatively modi- fied by copper sulfate (oxidized LDL), phosphatidylserine, cardiolipin, and 7-ketocholesteryl-9-carboxynonanoate.

16. An agent for inhibiting the growth of a calcified globule, which comprises an isolated antibody that comprises:
   a heavy chain of either an antibody comprising a heavy chain that comprises CDR1 having the amino acid sequence of SEQ ID NO: 21, CDR2 having the amino acid sequence of SEQ ID NO: 22, and CDR3 having the amino acid sequence of SEQ ID NO: 23; or an antibody comprising a heavy-chain variable region having the amino acid sequence of SEQ ID NO: 24; and
   a light chain of either an antibody comprising a light chain that comprises CDR1 having the amino acid sequence of SEQ ID NO: 26, CDR2 having the amino acid sequence of SEQ ID NO: 27, and CDR3 having the amino acid sequence of SEQ ID NO: 28; or an antibody comprising a light chain that comprises a light-chain variable region having the amino acid sequence of SEQ ID NO: 29.

* * * * *